(12) United States Patent
Fernandes et al.

(10) Patent No.: US 11,931,465 B2
(45) Date of Patent: Mar. 19, 2024

(54) FUNCTIONALIZED PRUSSIAN BLUE NANOPARTICLES, COMBINATION PRUSSIAN BLUE NANOPARTICLE-BASED NANO-IMMUNOTHERAPY AND APPLICATIONS THEREOF

(71) Applicant: Children's National Medical Center, Washington, DC (US)

(72) Inventors: Rohan Fernandes, Washington, DC (US); Raymond W. Sze, Washington, DC (US); Conrad Russell Y. Cruz, Washington, DC (US); Anthony D. Sandler, Washington, DC (US); Catherine M. Bollard, Washington, DC (US); Elizabeth E. Sweeney, Washington, DC (US); Juliana Cano-Mejia, Washington, DC (US); Rachel Burga, Washington, DC (US); Matthieu F. Dumont, Washington, DC (US)

(73) Assignee: Children's National Medical Center, Washington, DC (US)

( * ) Notice: Subject to any disclaimer, the term of this patent is extended or adjusted under 35 U.S.C. 154(b) by 1461 days.

(21) Appl. No.: 16/083,416

(22) PCT Filed: Mar. 8, 2017

(86) PCT No.: PCT/US2017/021396
§ 371 (c)(1),
(2) Date: Sep. 7, 2018

(87) PCT Pub. No.: WO2017/156148
PCT Pub. Date: Sep. 14, 2017

(65) Prior Publication Data
US 2020/0163899 A1 May 28, 2020

Related U.S. Application Data

(60) Provisional application No. 62/305,253, filed on Mar. 8, 2016.

(51) Int. Cl.
| | | |
|---|---|---|
| A61B 5/00 | (2006.01) |
| A61B 8/00 | (2006.01) |
| A61B 10/00 | (2006.01) |
| A61K 9/127 | (2006.01) |
| A61K 9/50 | (2006.01) |
| A61K 9/51 | (2006.01) |
| A61K 33/26 | (2006.01) |
| A61K 35/17 | (2015.01) |
| A61K 38/19 | (2006.01) |
| A61K 38/20 | (2006.01) |
| A61K 38/21 | (2006.01) |
| A61K 39/395 | (2006.01) |
| A61K 41/00 | (2020.01) |
| A61K 45/06 | (2006.01) |
| A61K 47/69 | (2017.01) |
| A61N 5/06 | (2006.01) |
| A61P 35/00 | (2006.01) |
| A61N 5/067 | (2006.01) |

(52) U.S. Cl.
CPC ............ *A61K 9/5146* (2013.01); *A61K 9/127* (2013.01); *A61K 9/5068* (2013.01); *A61K 9/5169* (2013.01); *A61K 33/26* (2013.01); *A61K 35/17* (2013.01); *A61K 38/193* (2013.01); *A61K 38/195* (2013.01); *A61K 38/20* (2013.01); *A61K 38/21* (2013.01); *A61K 39/39541* (2013.01); *A61K 41/0052* (2013.01); *A61K 45/06* (2013.01); *A61K 47/6901* (2017.08); *A61K 47/6935* (2017.08); *A61N 5/0616* (2013.01); *A61N 5/062* (2013.01); *A61N 5/0624* (2013.01); *A61N 5/0625* (2013.01); *A61P 35/00* (2018.01); *A61N 5/0601* (2013.01); *A61N 2005/0659* (2013.01); *A61N 2005/0663* (2013.01); *A61N 5/067* (2021.08)

(58) Field of Classification Search
CPC .... A61K 9/5146; A61K 9/127; A61K 9/5068; A61K 9/5169; A61K 33/26; A61K 35/17; A61K 38/193; A61K 38/195; A61K 38/20; A61K 38/21; A61K 39/39541; A61K 41/0052; A61K 45/06; A61K 47/6901; A61K 47/6935; A61N 5/0616
See application file for complete search history.

(56) References Cited

U.S. PATENT DOCUMENTS

| | | |
|---|---|---|
| 2011/0269170 A1 | 11/2011 | Kim et al. |
| 2013/0323305 A1 | 12/2013 | Paithankar et al. |
| 2014/0271487 A1 | 9/2014 | Fernandes et al. |

FOREIGN PATENT DOCUMENTS

| | | |
|---|---|---|
| CN | 103784979 A | 5/2014 |
| CN | 104474559 A | 4/2015 |
| CN | 106039311 A | 10/2016 |

OTHER PUBLICATIONS

Hoffman et al. (RSC Adv. 2014 4, 29729-29734).*
Dumont et al. (Int. J. Nanomed. 2014, 9, 2581-2595).*
Paholak, H.U.S. (2015) "Nanoparticle Design and Novel Approaches To Enhance Photothermal Cancer Therapy" Doctor of Philosophy (Pharmaceutical Sciences), University of Michigan.*

(Continued)

*Primary Examiner* — Michael G. Hartley
*Assistant Examiner* — Melissa J Perreira
(74) *Attorney, Agent, or Firm* — Oblon, McClelland, Maier & Neustadt, L.L.P.

(57) ABSTRACT

Combination treatment with Prussian blue nanoparticles and at least one immunotherapeutic treatment. Stable, functionalized Prussian blue nanoparticles, including those with enhanced stability under alkaline conditions, and methods of cancer, neoplasm, and tumor treatment using them, including photothermal treatment and combination immunotherapeutic treatments.

15 Claims, 24 Drawing Sheets

(56) References Cited

OTHER PUBLICATIONS

Wang et al. (Adv. Mater. 2014, 26, 8154-8162).*
Kennedy et al. (Nanoscale Res. Lett. 2011, 6, p. 2-11).*
European Office Action dated Aug. 3, 2020 in European Patent Application No. 17764011.7, 11 pages.
Cano-Majia, J., "Biodegradable Prussian blue nanoparticles for photothermal immunotherapy of advanced cancers", Retrieved from the internet: URL: https://drum.lib.umd.edu/handle/1903/17364 , 2015, 2 pages (submitting abstract).
International Search Report dated Jun. 28, 2017 in PCT/US2017/021396, 4 pages.
Hoffman, H.A., et al., "Prussian blue nanoparticles for laser-induced photothermal therapy of tumors", RSC Advances, vol. 4, 2014, pp. 29729-29734.
Galluzzi, L., et al., "Classification of current anticancer immunotherapies", Oncotarget, vol. 5, No. 24, Dec. 30, 2014, pp. 12472-12508.
Stephan, M.T., et al., "Synapse-directed delivery of immunomodulators using T-cell-conjugated nanoparticles", Biomaterials, vol. 33 No. 23, 2012, 25 pages.
Extended European Search Report dated Oct. 2, 2019, in Patent Application No. 17764011.7, 9 pages.
European Office Action dated Feb. 27, 2023 in European Patent Application No. 17 764 011.7, 11 pages.
Feng et al., "Glypican-3 antibodies: A new therapeutic target for liver cancer", FEBS Letters, vol. 588, Oct. 15, 2013, pp. 377-382, XP028669969.

* cited by examiner

Graphical Abstract

FUNCTIONALIZED PRUSSIAN BLUE NANOPARTICLES, COMBINATION PRUSSIAN BLUE NANOPARTICLE-BASED NANO-IMMUNOTHERAPY AND APPLICATIONS THEREOF

CROSS-REFERENCE TO RELATED APPLICATIONS

This application claims priority to U.S. Provisional Application No. 62/305,253, filed Mar. 8, 2016 which is incorporated by reference in its entirety.

This application is also related to U.S. application Ser. No. 14/213,380, filed Mar. 14, 2014, now U.S. 20140271487 A1, entitled PRUSSIAN BLUE-INSPIRED CONSTRUCTS FOR MULTIMODAL IMAGING AND THERAPY which is hereby incorporated by reference in its entirety. References cited herein are also incorporated by reference, especially for the subject matter referenced by the citation.

FIELD OF THE INVENTION

The present invention falls within the fields of immunotherapy and photothermal therapies that make use of Prussian blue nanoparticles. Examples of such combined therapies include the use of antigen-specific T cells conjugated to Prussian blue nanoparticles to target antigens of tumors and microbial pathogens, the use of inhibitors, such as MEK inhibitors or checkpoint inhibitors in combination with Prussian blue photothermal therapy for treatment of neuroblastoma or other types of cancers, tumors or malignancies. As shown herein, the combination of these therapies provide superior and surprising benefits in reducing the severity of diseases.

BACKGROUND OF THE INVENTION

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure. The background pertinent to various aspects and embodiments of the invention is provided in the sections and Examples which follow.

BRIEF SUMMARY OF THE INVENTION

The inventors show herein that Prussian blue nanoparticles can be stabilized and used in combination with an immunotherapy to treat neuroblastoma, other cancers, as well as other diseases, disorders or conditions amenable to treatment with immunotherapy. One component of the combination therapy is Prussian blue nanoparticles, which may be functionalized. The other component is one or more immunotherapies such as those involving immunomodulators, such as checkpoint inhibitors, antibodies, or T cells and other immunocytes. Specific aspects of the invention are directed to combination therapies consisting of multifunctional, theranostic Prussian blue nanoparticles combined with one or more immunotherapies, and their applications. These combination therapies, termed nano-immunotherapies, comprise two important components: 1) Prussian blue nanoparticles and 2) at least one immunotherapy. The two therapies can be administered simultaneously, sequentially (one before the other), or as a single entity where the two components are attached to each other (using conjugation techniques described herein).

Prussian blue nanoparticles according to some embodiments of the invention exhibit theranostic features. These features permit the nanoparticles to be simultaneously used for diagnosis and therapy. In some embodiments Prussian blue nanoparticles will have: (1) small sizes, such as average diameters ranging from 1-400 nm, (2) a high surface area to volume ratio that enable attachment of targeting ligands to the nanoparticles, (3) an ability to be imaged or visualized using techniques, e.g. by fluorescence imaging or MRI, (4) an ability to function as, carry or target therapeutic agents, e.g. their use as photothermal therapy agents, and/or (5) an ability to degrade in biological fluids such blood, plasma, tissue fluid, lymph, CSF, etc.

A second component of the combination therapy consists of one or more immunotherapies. These function to treat diseases by directly or indirectly modulating or affecting immune responses, such as by suppressing, stabilizing, inducing or enhancing particular cellular, humoral or other immune responses. Examples of immunotherapies include using an immunomodulator, e.g. chemokines, cytokines, oligodeoxynucleotides; antibodies, e.g. anti-CTLA-4, anti-GD2; or the administration of immune cells such as NK cells or antigen-specific T-cells.

The invention combines two discrete but synergistic therapies: a therapy, such as a photothermal therapy, using Prussian blue nanoparticles and at least one immunotherapy. The combination therapy provides treatment outcomes that are significantly superior to the individual therapies in the combination. These superior outcomes cannot be explained merely as the addition of the effects of the two individual therapies. For example, the combination therapy yields complete tumor regression and long-term survival in 55% of mice with an aggressive cancer compared with only 12.5% survival and 0% survival when using individual components of the combination therapy.

The various aspects of the invention involve methods using a combination of Prussian blue nanoparticles in combination with immunotherapies where the nanoparticles may be functionalized and stable once administered in vivo. These and other aspects of the invention are described in more detail in the following disclosure and claims.

BRIEF DESCRIPTION OF THE DRAWINGS

FIG. 1A) DLS was used to measure the sizes (hydrodynamic diameters) of the PB NPs in water. FIG. 1B) Vis-NIR spectroscopy was used to measure the absorbance of PB NPs between the wavelengths of 400-1100 nm. FIG. 1C) Four concentrations of PB NPs were irradiated with an 808 nm laser (1.25 W/cm$^2$) for 10 minutes and temperature was measured every minute. Black: 1.0 mg/mL, blue: 0.1 mg/mL, red: 0.01 mg/mL PB NPs. Solid gray line indicates water alone. Mean±standard deviation, n=3.

FIG. 2A) DLS was used to measure the hydrodynamic diameters of the PB NPs in PBS. FIG. 2B) Vis-NIR spectroscopy was used to measure the absorbance of PB NPs between the wavelengths of 400-1100 nm after contacting with PBS for 0, 2, 24, and 48 h. FIG. 2C) PB NPs in PBS were irradiated with an 808 nm laser (1.25 W/cm$^2$) for 10 minutes, and temperature was measured every minute. Black: 1.0 mg/mL, blue: 0.1 mg/mL, red: 0.01 mg/mL PB NPs. Dotted gray line indicates PBS alone. The arrows and values note the decrease in PTT capabilities of the PB NPs in PBS relative to their properties in water. Mean±standard deviation, n=3.

Figure 3:
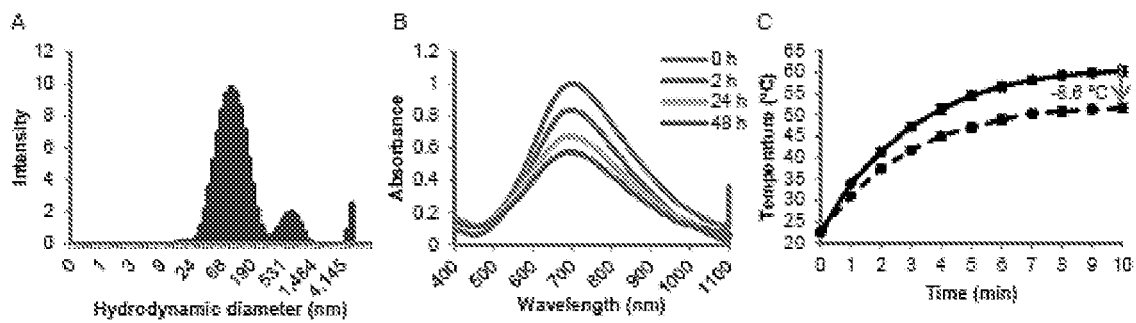

FIG. 3. The effect of albumin-coating on the stability, Vis-NIR, and PTT properties of PB NPs in PBS. FIG. 3A) DLS was used to measure the hydrodynamic diameters of albumin-coated PB NPs in PBS. FIG. 3B) Vis-NIR spectroscopy was used to measure the absorbance of albumin-coated PB NPs between the wavelengths of 400-1100 nm after contacting with PBS for 0, 2, 24, and 48 h. FIG. 3C) 1 mg/mL albumin-coated PB NPs in water (solid line) or PBS (dotted line) were irradiated with a NIR laser (1.25 W/cm$^2$) for 10 minutes, and temperature was measured every minute. The arrow and values note the decrease in PTT capabilities of the albumin-coated PB NPs in PBS relative to their properties in water. Mean±standard deviation, n=3.

Figure 4:
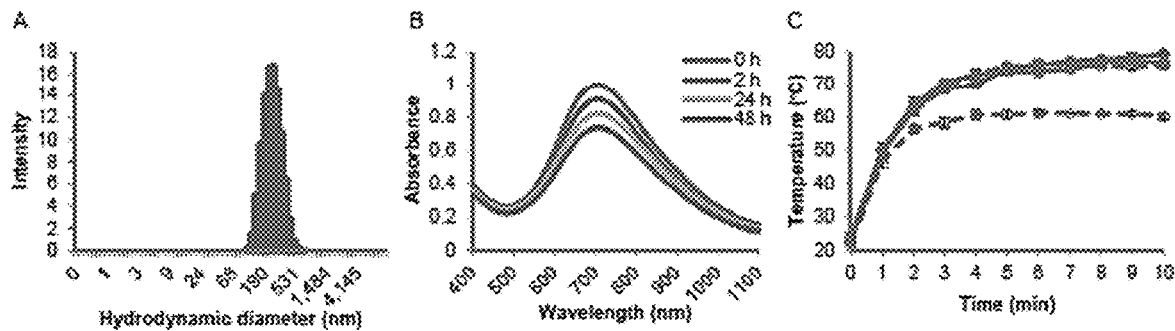

FIG. 4. The effect of LbL-coating on the stability, Vis-NIR, and PTT properties of PB NPs in PBS. FIG. 4A) DLS was used to measure the hydrodynamic diameters of the LbL-coated PB NPs in PBS. FIG. 4B) Vis-NIR spectroscopy was used to measure the absorbance of LbL-coated PB NPs between the wavelengths of 400-1100 nm after contacting with PBS for 0, 2, 24, and 48 h. FIG. 4C) 1 mg/mL LbL-coated PB NPs in water (solid blue) or PBS (dotted blue) were irradiated with a NIR laser (1.25 W/cm$^2$) for 10 minutes, and temperature was measured every minute. For comparison, uncoated PB NPs in water (solid red) and PBS (dotted red) were also included. Mean±standard deviation, n=3.

Figure 5:
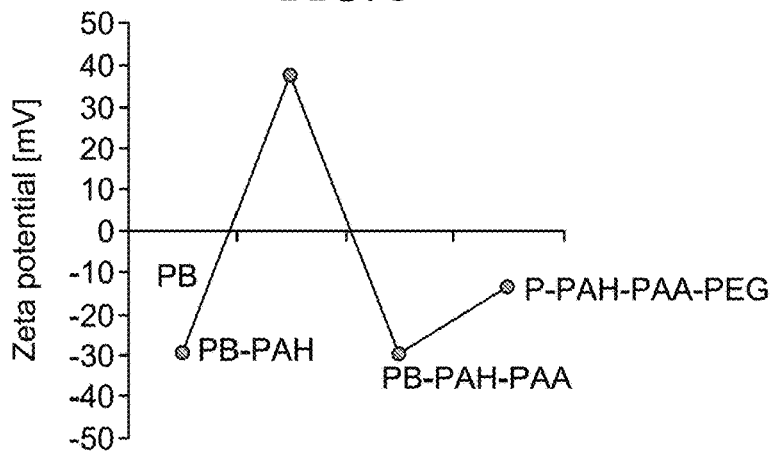

FIG. 5. Surface charges of LbL-coated PB NPs. Zeta potential of nanoparticles was measured after each layering step of the LbL-coating synthesis. Mean±standard deviation, n=3.

Figure 6:
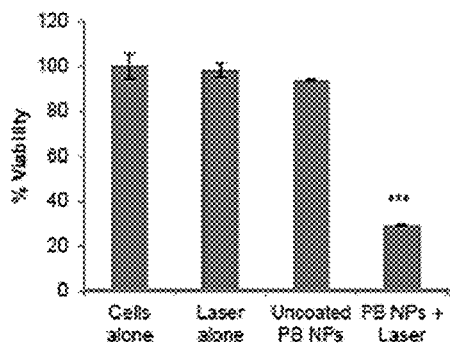

FIG. 6. The effect of PB NP-based PTT on neuroblastoma cells. Neuro2a neuroblastoma cells were treated with control media, the 808 nm laser alone (10 min, 1.25 W/cm$^2$), PB NPs (0.1 mg/mL, 24 h) alone, or PB NPs (0.1 mg/mL, 24 h)+808 nm laser (10 min, 1.25 W/cm$^2$). Cell viability (% viability) was read 2 h post XTT assay. *** p<0.0001 compared to all other groups. Mean±standard deviation, n=3.

Figure 7:
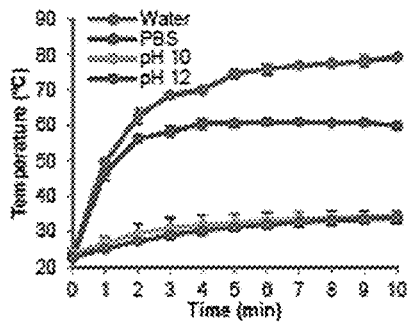

FIG. 7. The effect of pH on PTT properties of PB NPs. Uncoated PB NPs (1 mg/mL) were incubated in water, PBS, or solutions of pH 10 or 12 for 24 h and then transferred into a 96-well plate. PTT was performed on each well using the conditions described previously, and temperatures were measured. Mean±standard deviation, n=3.

Figure 8:
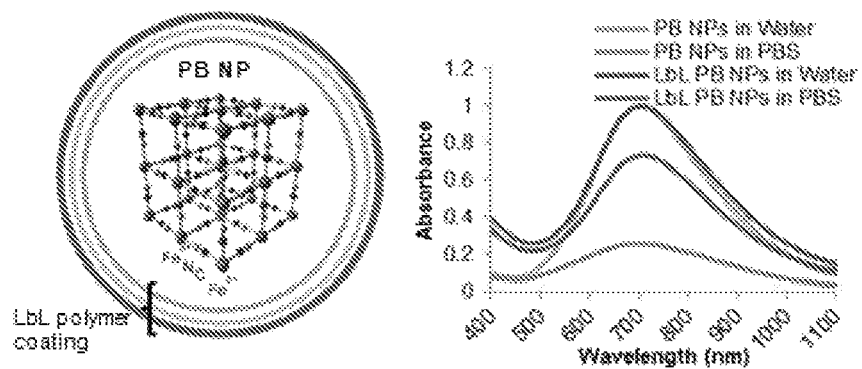

FIG. 8. Graphical Abstract depicting some embodiments of Prussian blue nanoparticles. As shown different Prussian blue compositions exhibit different absorbance properties.

Figure 9:
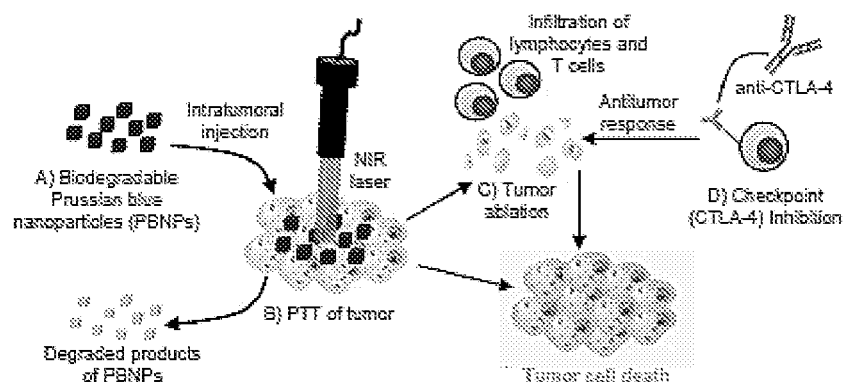

FIG. 9. Prussian blue nanoparticle-based photothermal therapy combined with checkpoint inhibition for photothermal immunotherapy of neuroblastoma. A) Prussian blue nanoparticles (PBNPs) that exhibit pH-dependent stability are i.t. (locally) injected into tumors. B) A low power, near infrared (NIR) laser irradiates PBNPs within the tumor effecting photothermal therapy (PTT) of the tumor, which results in tumor cell death. C) PTT also elicits an immune response resulting in the increased infiltration of lymphocytes and T cells to the tumor area. D) I.p. (systemically) administered anti-CTLA-4 reverses immunosuppression, unleashing the antitumor immune responses of endogenous immune cells, particularly T cells. The above processes combine to yield improved tumor responses and development of immunity against tumor rechallenge in a mouse model of neuroblastoma. (For interpretation of the references to color in this figure legend, the reader is referred to the web version of Cano-Mejia, et al., Nanomedicine: Nanotechnology, Biology, and Medicine 13 (2017) 771-781, which is incorporated by reference.)

Figure 10:
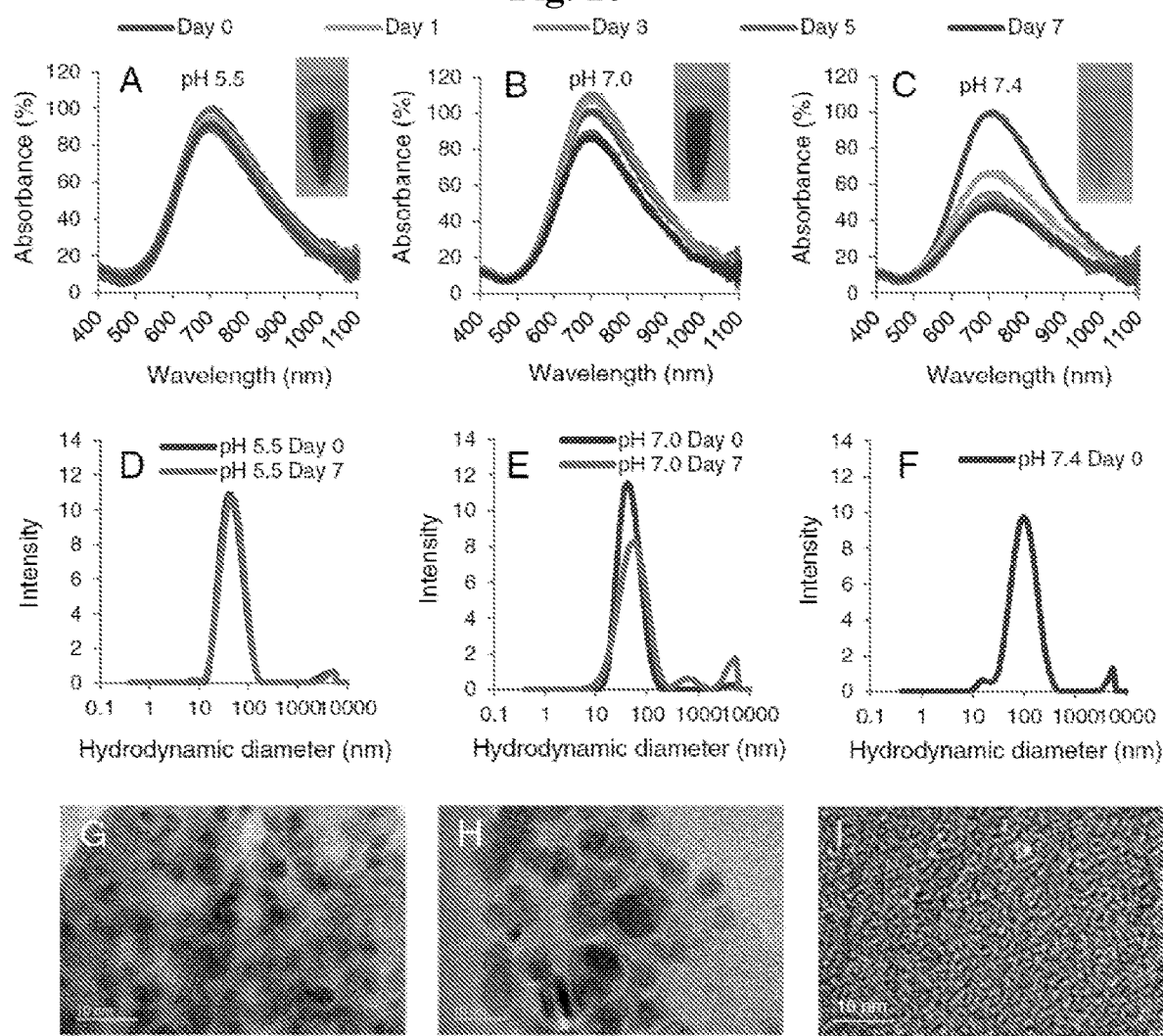

FIG. 10. pH-dependent properties of PBNPs. (FIG. 10A-10C) Visible-NIR spectra of PBNPs over 7 days at pH 5.5 (FIG. 10A), pH 7.0 (FIG. 10B), and pH 7.4 (FIG. 10C), exhibiting PBNP stability at mildly acidic (5.5) and neutral (7.0) pHs, and decreased PBNP stability at a mildly alkaline pH (7.4). Insets: PBNP photographs on Day 7 at a pH of 5.5, 7.0, and 7.4, respectively. (FIG. 10D-10F) Dynamic light scattering analysis of the PBNPs over 7 days (Day 0: blue, Day 7: red) at pH 5.5 (FIG. 10D), 7.0 (FIG. 10E), and pH 7.4 (FIG. 10F), illustrating detectable PBNP populations at mildly acidic (5.5) and neutral (7.0) pHs over 7 days, and undetectable PBNP populations at a mildly alkaline pH (7.4) on Day 7. (FIG. 10G-10I) TEM images of PBNPs on Day 7 at pH 5.5 (FIG. 10G), pH 7.0 (FIG. 10H), and pH 7.4 (FIG. 10I) showing detectable PBNPs at mildly acidic (5.5) and neutral (7.0) pHs, and undetectable PBNPs at a mildly alkaline pH (7.4). (For interpretation of the references to color in this figure legend, the reader is referred to the web version of Cano-Mejia, et al., Nanomedicine: Nanotechnology, Biology, and Medicine 13 (2017) 771-781, which is incorporated by reference.)

Figure 11:
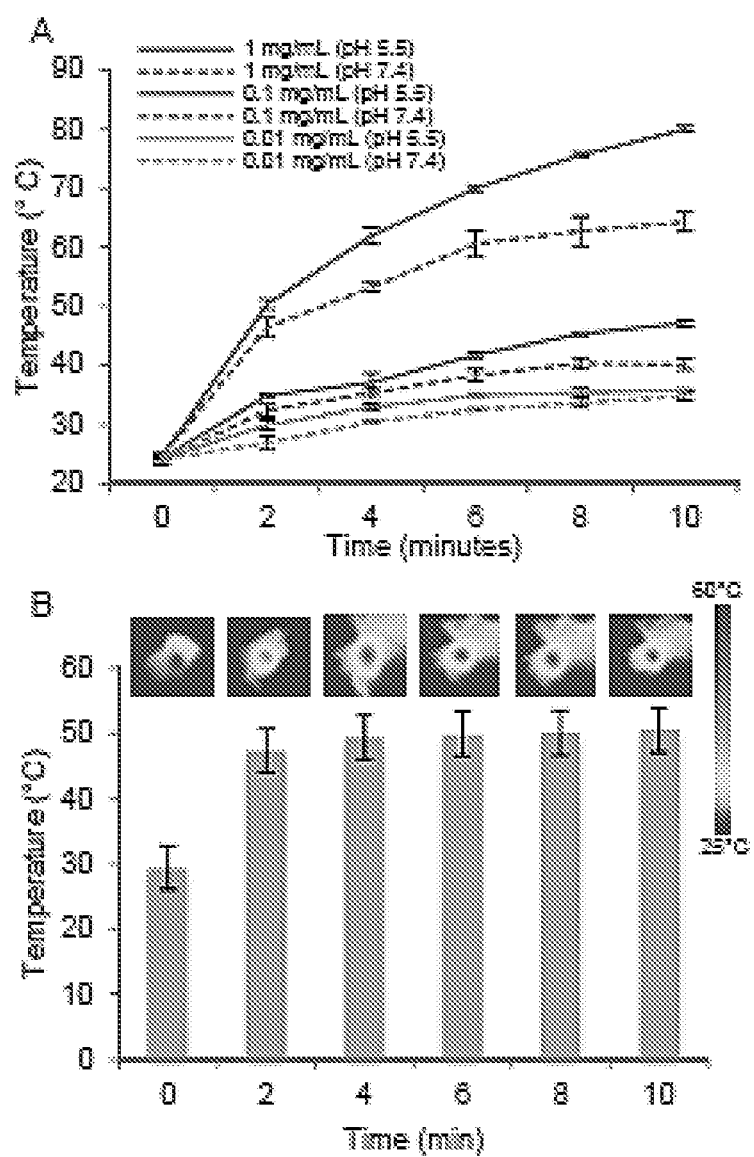

FIG. 11. In vitro and in vivo PTT capabilities of PBNPs. FIG. 11A shows in vitro PTT capabilities of varying concentrations of PBNPs at pH 5.5 and 7.4 showing decreased heating at higher pHs. FIG. 11B shows temperatures achieved by intratumorally injecting 50 microliters (1 mg/ml) PBNPs irradiated with a 808 nm NIR laser for 10 mins at 1.875 W/cm$^2$. Inset shows heat maps of increased temperatures about 50-55° C. achieved at the injection site that rapidly decreases to body temperature about 37° C. outside the tumor region.

Figure 12:
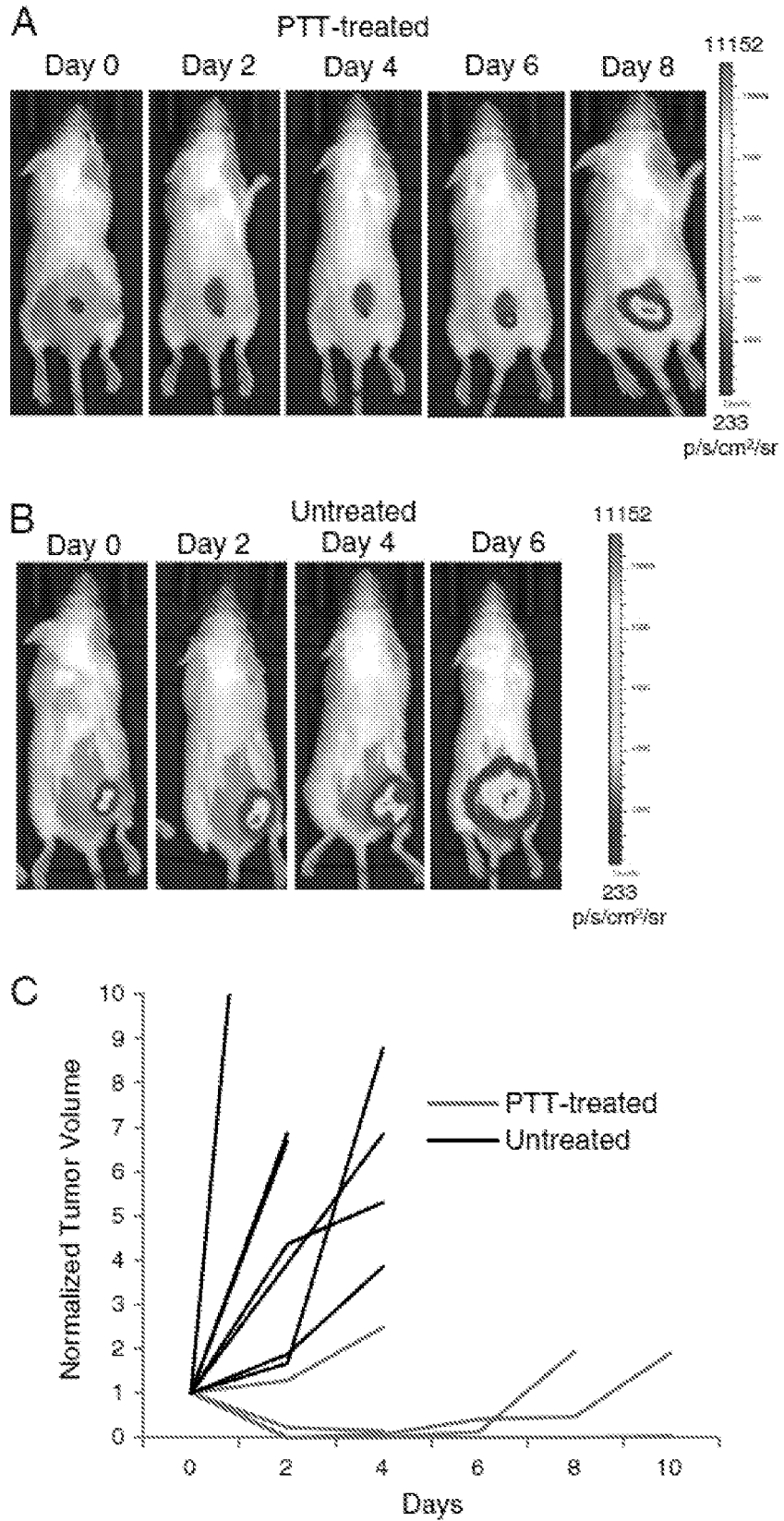

FIG. 12. Efficacy of PBNP-based PTT in vivo. (A-B) Representative images of a (FIG. 12A) PTT-treated, tumor-bearing mouse showing debulking of the tumor mass after PTT and an (FIG. 12B) Untreated tumor-bearing mouse showing tumor growth (scale bars=tumor bioluminescence intensity; p/s/cm$^2$/sr). (FIG. 12C) Normalized tumor growth curves for untreated (black) and PTT-treated (red) tumor-bearing mice showing slower tumor growth in PTT-treated mice relative to untreated controls (n≥5/group). Lower three traces (red); other upper traces (black). (For interpretation of the references to color in this figure legend, the reader is referred to the web version of Cano-Mejia, et al., Nanomedicine: Nanotechnology, Biology, and Medicine 13 (2017) 771-781, which is incorporated by reference.)

Figure 13:
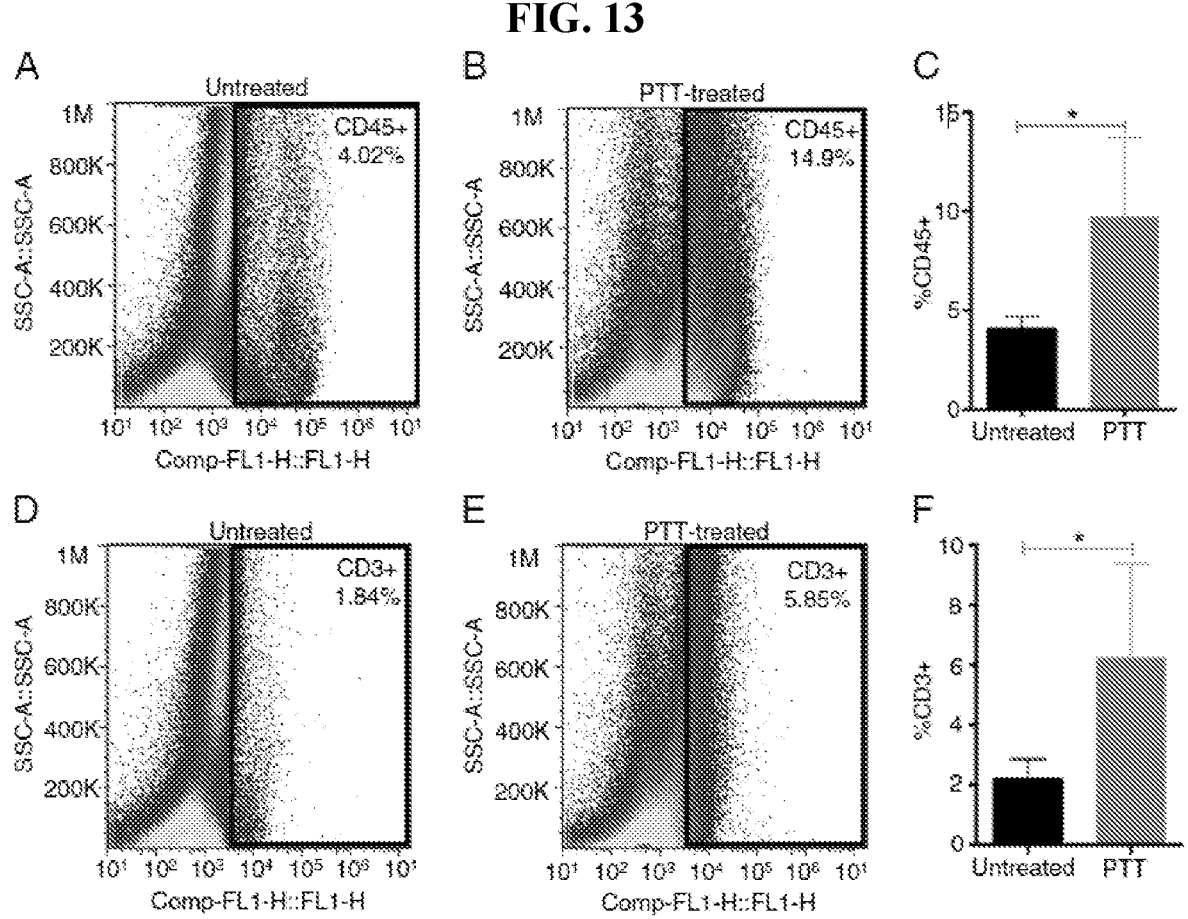

FIG. 13. Immunostimulatory effects of PBNP-based PIT. Representative scatter plots of CD45+ cells in tumors of: FIG. 13A) Untreated and FIG. 13B) PTT-treated mice. FIG. 13C) % CD45+ cells in the tumors of untreated and PTT-treated mice showing significantly higher percentage of CD45+ cells in tumors of PTT-treated vs. untreated mice (p=0.0294). Representative scatter plots of CD3+ cells in tumors of: FIG. 13D) Untreated and FIG. 13E) PTT-treated mice. FIG. 13F) % CD3+ cells in the tumors of untreated and PTT-treated mice showing significantly higher percentage of CD3+ cells in tumors of PTT-treated vs. untreated mice (p=0.0424); (n≥4/group for this study).

Figure 14:
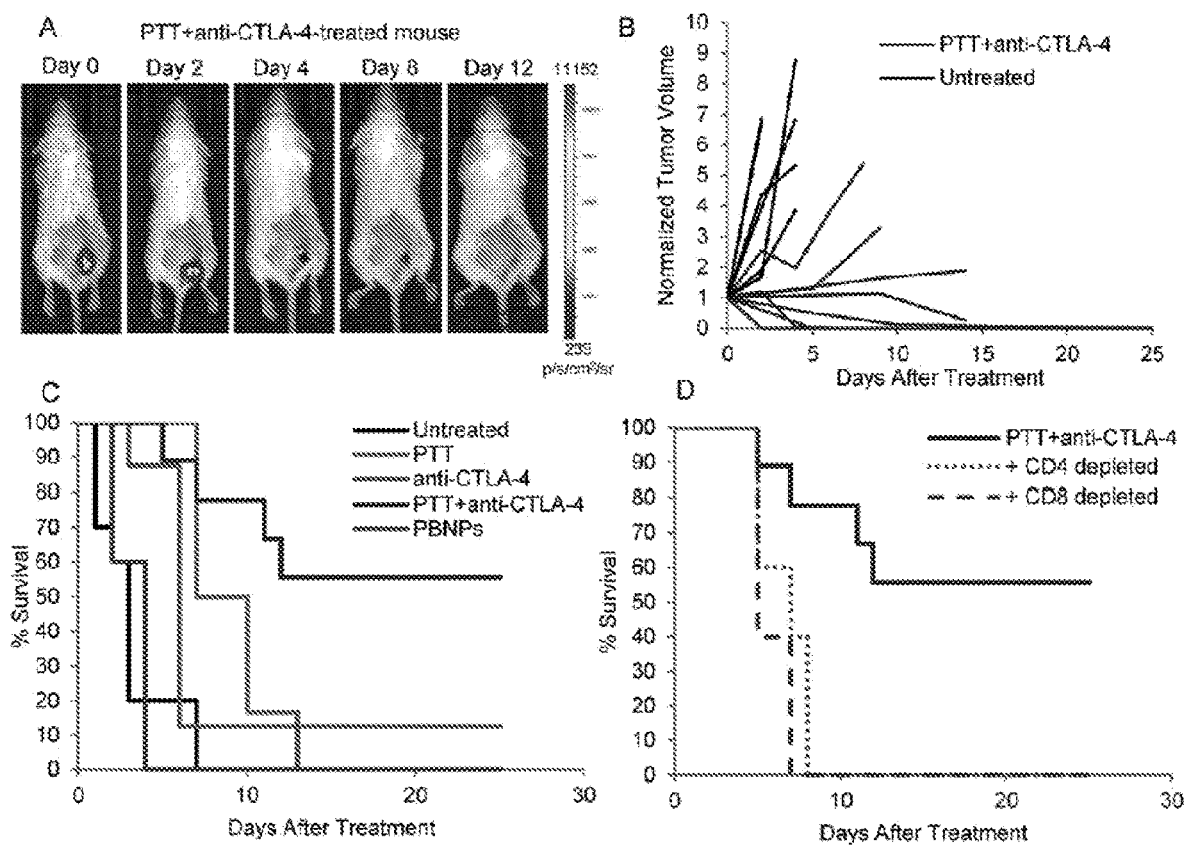

FIG. 14. Effect of photothermal immunotherapy (PTT+anti-CTLA-4 therapy) on tumor regression and long-term survival in the neuroblastoma mouse model. FIG. 14A) Representative image of a long-term surviving mouse treated with PTT+anti-CTLA-4 showing complete tumor regression (scale bar=tumor bioluminescence intensity; p/s/cm$^2$/sr). FIG. 14B) Normalized tumor growth curves for tumor-bearing mice treated with PTT+anti-CTLA-4 (violet) or left untreated (black). (FIG. 14C) Kaplan-Meier survival plots of neuroblastoma mice that were treated with PTT+anti-CTLA-4, PBNPs alone, anti-CLTA-4 alone, PTT alone, or untreated. Mice receiving photothermal immunotherapy showed significantly higher long-term survival (N100 days) compared with mice in the other groups (log-rank test; p b 0.05); (n≥5/group). (FIG. 14D) Kaplan-Meier survival plots of neuroblastoma-bearing mice depleted in CD4+ and CD8+ T cells. Depletion of CD4+ and CD8+ cells (n=5/group) effectively abrogated the therapeutic responses of the photothermal immunotherapy (log-rank test; p b 0.005). (For interpretation of the references to color in this figure legend, the reader is referred to the web version of Cano-Mejia, et al., Nanomedicine: Nanotechnology, Biology, and Medicine 13 (2017) 771-781, which is incorporated by reference.)

Figure 15:
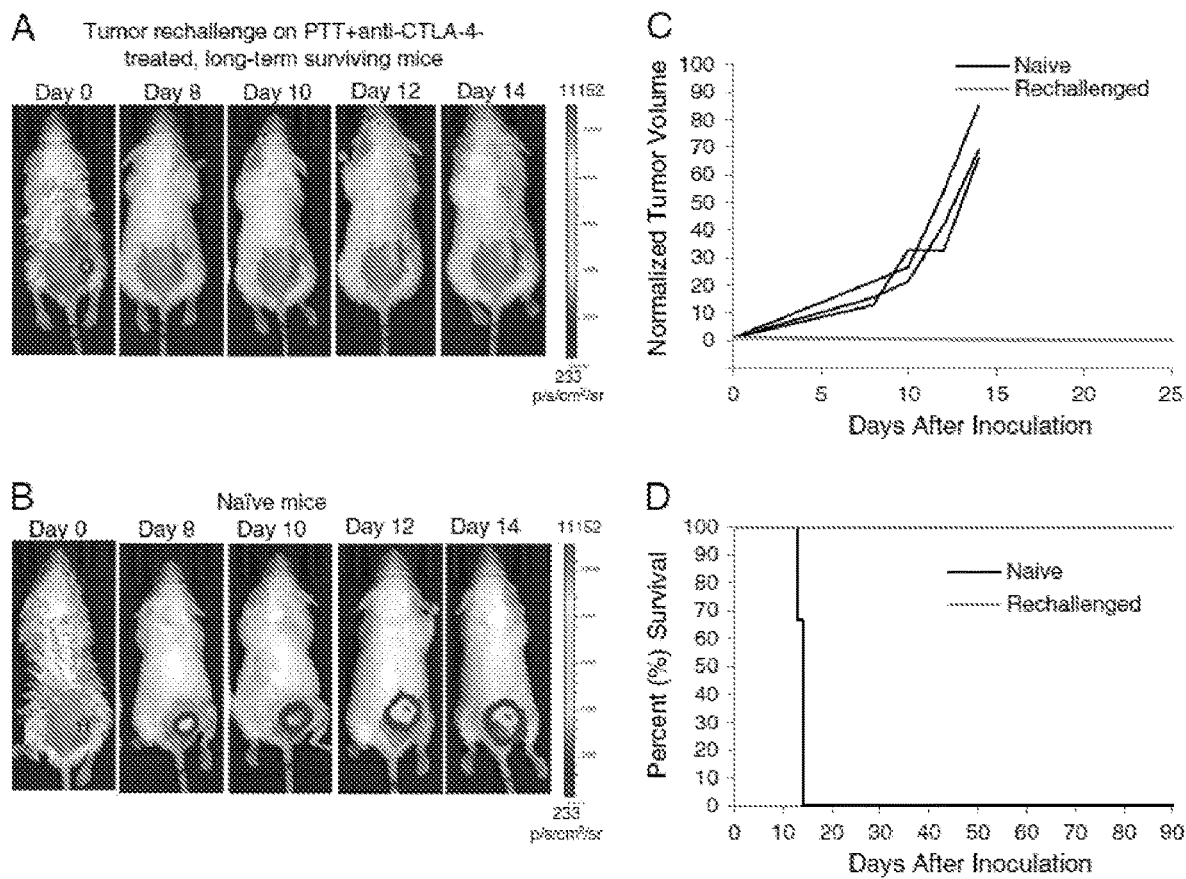

FIG. 15: Effect of tumor rechallenge in photothermal immunotherapy-treated, long-term surviving mice. (FIGS. 15A and 15B) Representative images showing protection against tumor rechallenge in (FIG. 15A) photothermal immunotherapy-treated mice and (FIG. 15B) tumor growth in naïve, untreated mice (scale bars=tumor bioluminescence intensity; p/s/cm$^2$/sr). (FIG. 15C) Tumor growth curves after challenge with 10$^6$ Neuro2a cells in untreated mice (naïve, black) and long-term surviving photothermal immunotherapy-treated mice (rechallenged, orange) showing protection in the rechallenged group compared to progression in the naïve group. (FIG. 15D) Kaplan-Meier survival plots showing significantly higher long-term survival in the rechallenged group compared to naïve mice (log-rank test, p b 0.05); (n≥3/group). (For interpretation of the references to color in this figure legend, the reader is referred to the web version of Cano-Mejia, et al., Nanomedicine: Nanotechnology, Biology, and Medicine 13 (2017) 771-781, which is incorporated by reference.)

Figure 16:
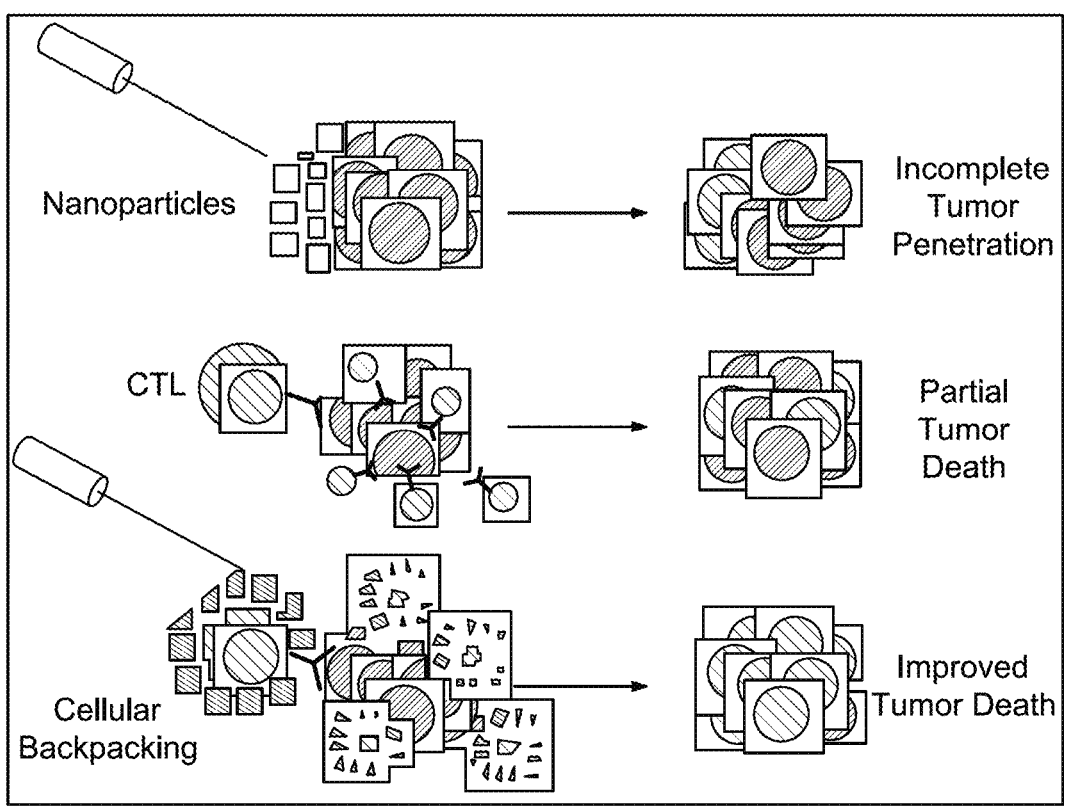

FIG. 16. Graphical abstract illustrating the advantages of combined therapy.

Figure 17:
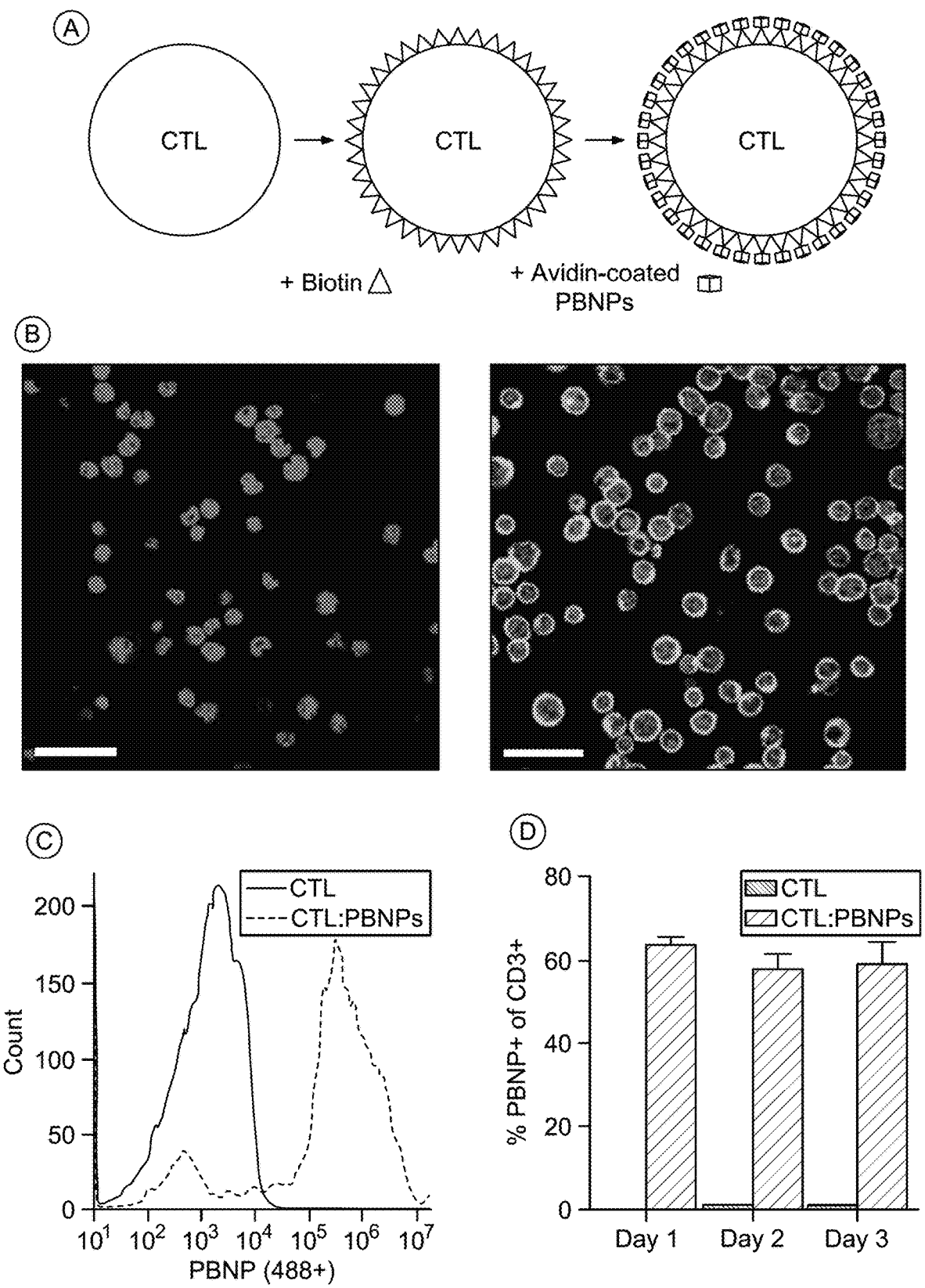

FIG. 17. Developing a schema for successful attachment of Prussian blue nanoparticles onto cytotoxic T lymphocytes. (A) The inventors propose a schema by which fluorescent avidin-coated PBNPs are conjugated to the surface of biotinylated CTL. (B) Confocal microscopy images (20×) demonstrating successful conjugation of PBNPs (Alexafluor488+) onto Jurkat cells (DAPI+) taken immediately after cell-nanoparticle conjugation (Day 1); scale bar=10 μm. (C & D) Flow cytometry was used to evaluate the persistence of the PBNP coating, as indicated by the AlexaFluor488+ population; cells were pre-gated as CD3+, n=3. PBNP: Prussian blue nanoparticle.

Figure 18:
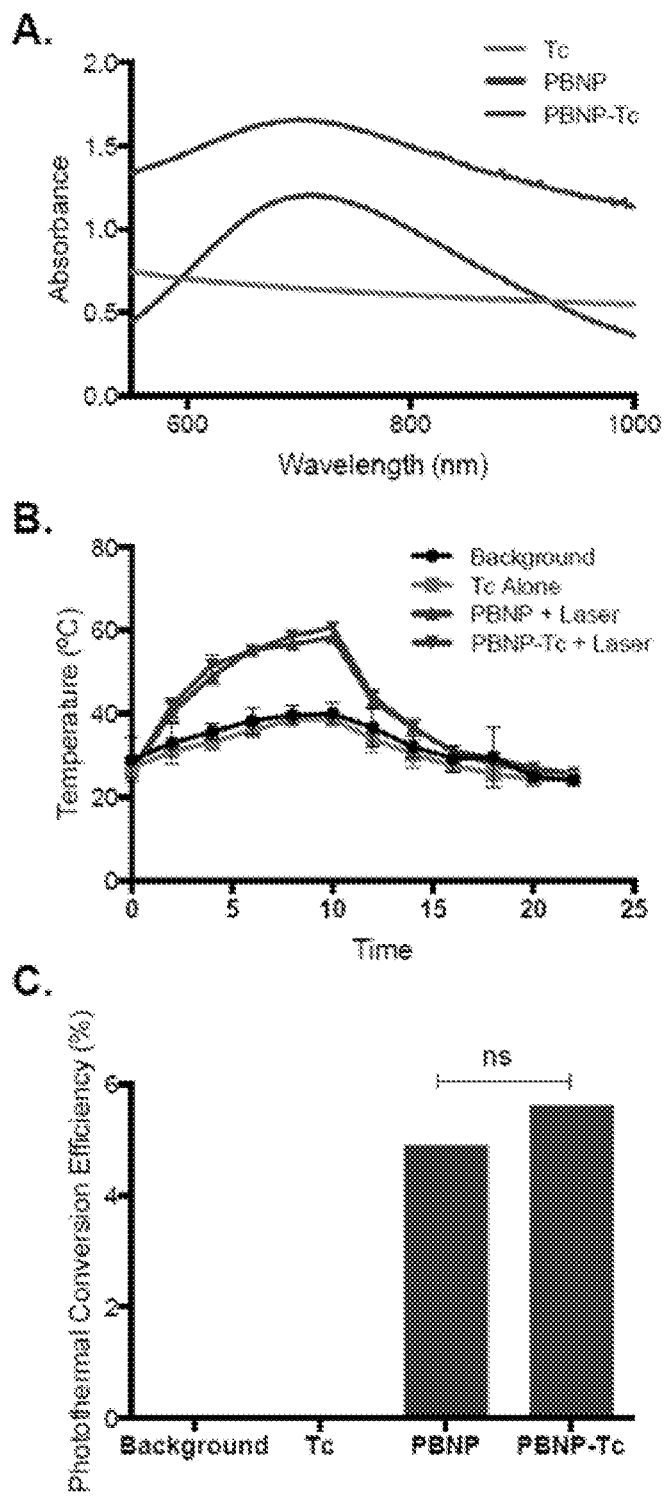

FIG. 18: Prussian blue nanoparticle backpacked T cells are functional as agents of PTT. (FIG. 18A) UV Visible spectra of PBNP alone, Tc alone, and backpacked PBNP-Tc; a peak in the range of 680-720 nm indicates light absorption in the near infrared range, highlighting potential performance as an agent of photothermal therapy. (FIG. 18B) Temperature profile of culture wells in response to ten minutes exposure to the near infrared laser (0.98 W) alone, wells with T cells alone, wells with PBNP alone, and wells with backpacked PBNP-Tc, followed by 10 minutes at room temperature to allow for cooling. (FIG. 18C) Heating and cooling temperatures in the aforementioned were monitored and used to calculate the photothermal conversion efficiency of our nanoparticles as compared to nanoparticle-backpacked T cells. N=3.

Figure 19:
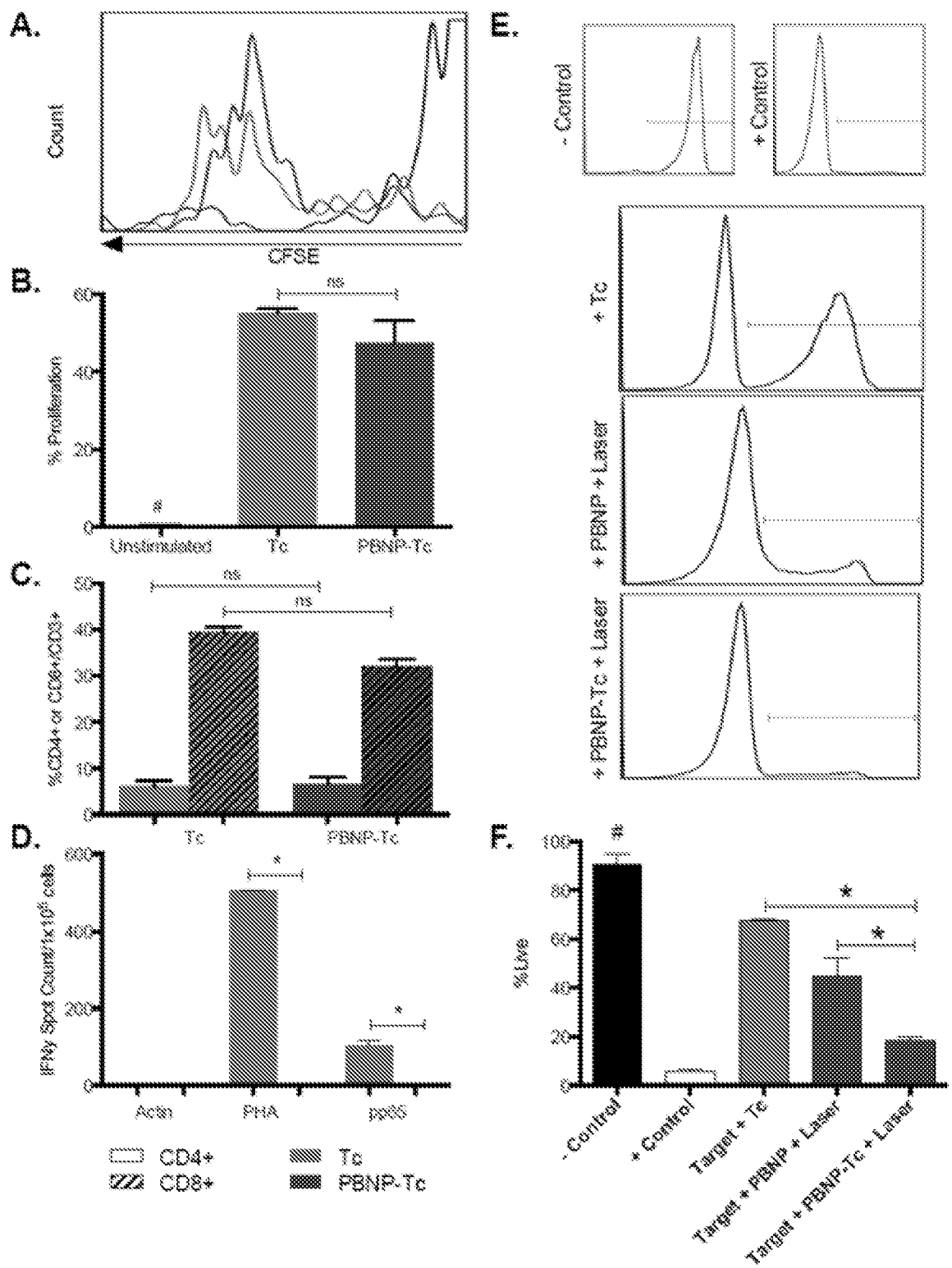

FIG. 19: Cellular backpacking for combined photothermal immunotherapy with CMV specific T cells. It was essential to determine that CMV peptide-specific T cell functionality was not impaired by cellular backpacking. (FIG. 19A) Representative histograms depicting CFSE-labeled T cells alone or in PBNP-Tc constructs either left unstimulated or co-cultured with pp65 peptide-pulsed target cells, and allowed to proliferate for 24 hours. (FIG. 19B) Aggregate results of cell proliferation, n=3, with results indicative of experiments conducted with 3 separate donors. (FIG. 19C) T cells and backpacked PBNP-Tc the inventors assayed by flow cytometry to determine their phenotype, with aggregate results of CD4+ T cells and CD8+ T cells subsets shown; n=3, with results indicative of experiments conducted with 3 separate donors. (FIG. 19D) Aggregate results of IFN gamma producing T cells from ELISpot performed on T cells and PBNP-Tc in response to nonspecific (actin), panspecific (PHA) or specific (pp65 peptide) stimulation; n=3, with results indicative of experiments conducted with 3 separate donors. (FIG. 19E) In vitro experiments were conducted to examine the viability of labeled target cells (pp65 peptide presenting PHA blasts) in response to co-culture with T cells alone, PBNP alone plus ten minutes with the near infrared laser, or co-culture with PBNP-Tc followed by ten minutes with the near infrared laser. Negative control was target cells cultured alone (top left), and positive control was target cells cultured with DMSO (top right). Representative histograms depicting target cell viability with co-culture with CMV-specific T cells (top), PBNP alone plus laser (middle), with PBNP-Tc construct plus laser (bottom). (FIG. 19F) Aggregate results from above indicating significant reduction in target cell viability with either modality alone as well as the combined PBNP-Tc construct plus laser; n=3, with results indicative of experiments conducted with 3 separate donors.

Figure 20:
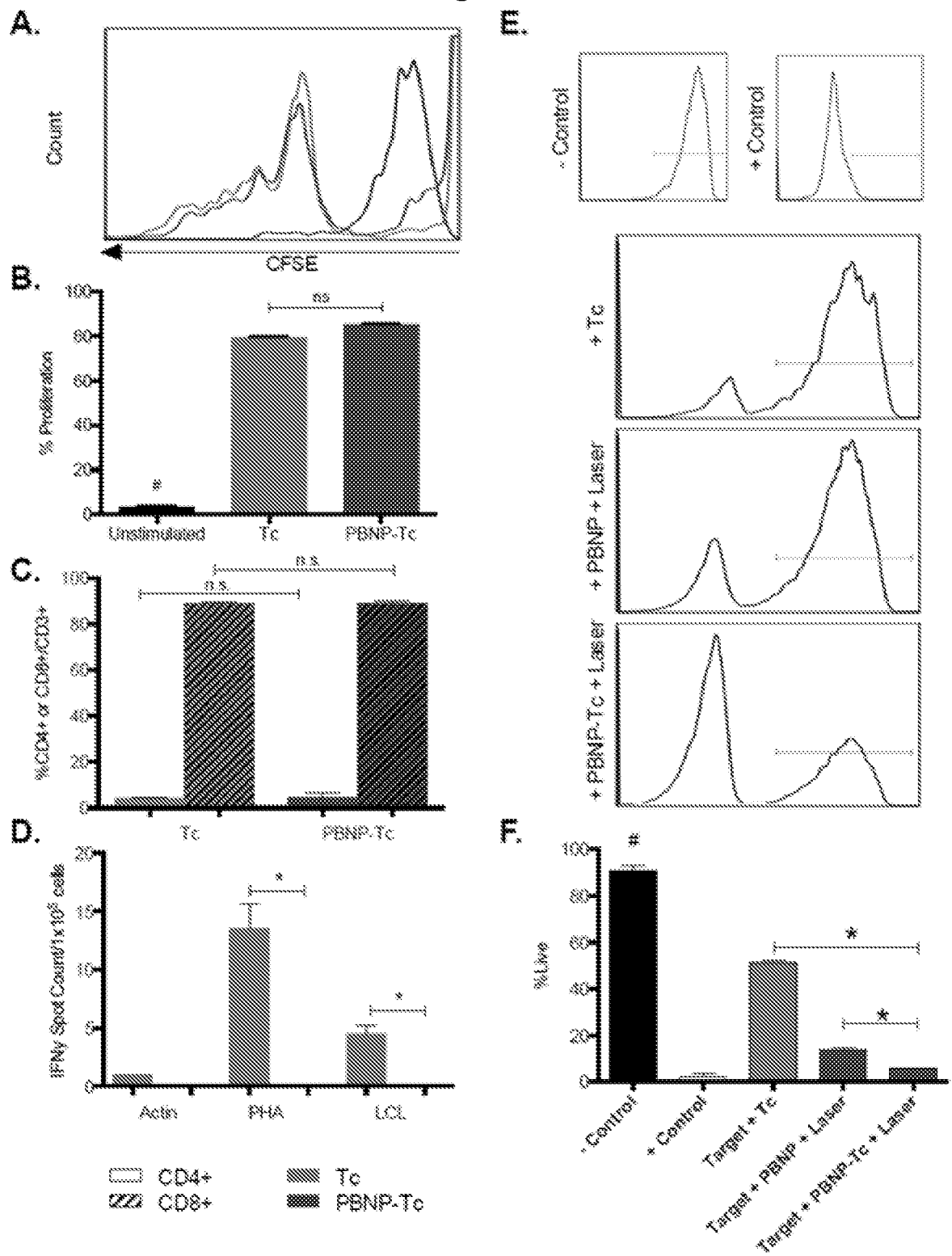

FIG. 20. Cellular backpacking for combined photothermal immunotherapy with EBV Specific CTL. It was essential to determine that EBV-specific T cells functionality was not impaired by cellular backpacking. (FIG. 20A) Representative histograms depicting CFSE-labeled T cells alone or in PBNP-Tc constructs either left unstimulated or co-cultured with irradiate LCL target cells (naturally EBV expressing), and allowed to proliferate for 24 hours. (FIG. 20B) Aggregate results of cell proliferation, n=3, with results indicative of experiments conducted with 2 separate donors. (FIG. 20C) T cells and backpacked PBNP-Tc the inventors assayed by flow cytometry to determine their phenotype, with aggregate results of CD4+ T cells and CD8+ T cells subsets shown; n=3, with results indicative of experiments conducted with 2 separate donors. (FIG. 20D) Aggregate results of IFN-gamma producing T cells from ELISpot performed on T cells and PBNP-Tc in response to nonspecific (actin), panspecific (PHA) or specific (irradiated LCL) stimulation; n=3, with results indicative of experiments conducted with 2 separate donors. (FIG. 20E) In vitro experiments were conducted to examine the viability of labeled target cells (LCL cells) in response to co-culture with T cells alone, PBNP alone plus ten minutes with the near infrared laser, or co-culture with PBNP-Tc followed by ten minutes with the near infrared laser. Negative control was target cells cultured alone (top left), and positive control was target cells cultured with DMSO (top right). Representative histograms depicting target cell viability with co-culture with EBV-specific T cells (top), PBNP alone plus laser (middle), with PBNP-Tc construct plus laser (bottom). (FIG. 20F) Aggregate results from above indicating significant reduction in target cell viability with either modality alone as well as the combined PBNP-Tc construct plus laser; n=3, with results indicative of experiments conducted with 2 separate donors.

Figure 21:
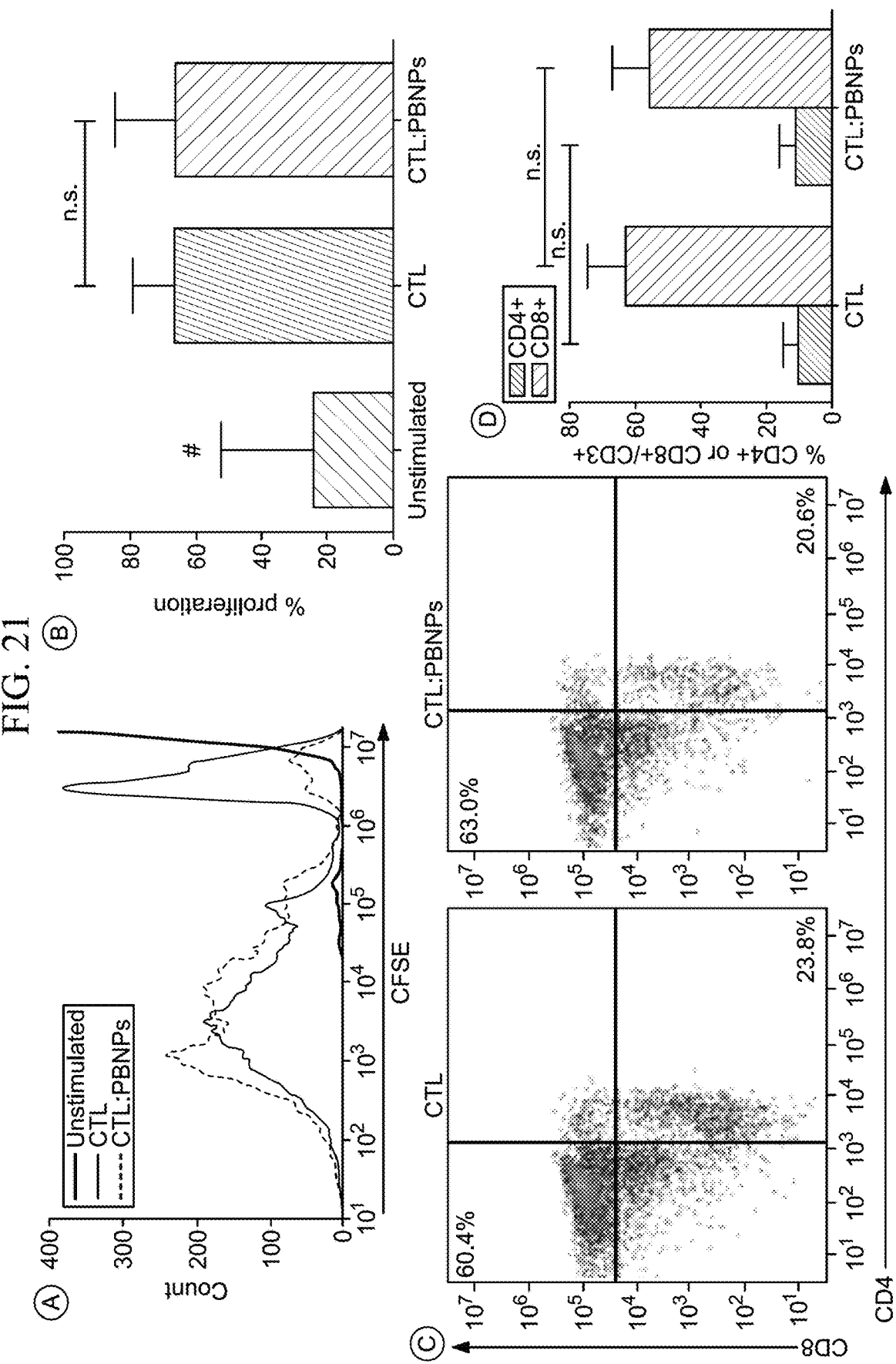
Figure 21:
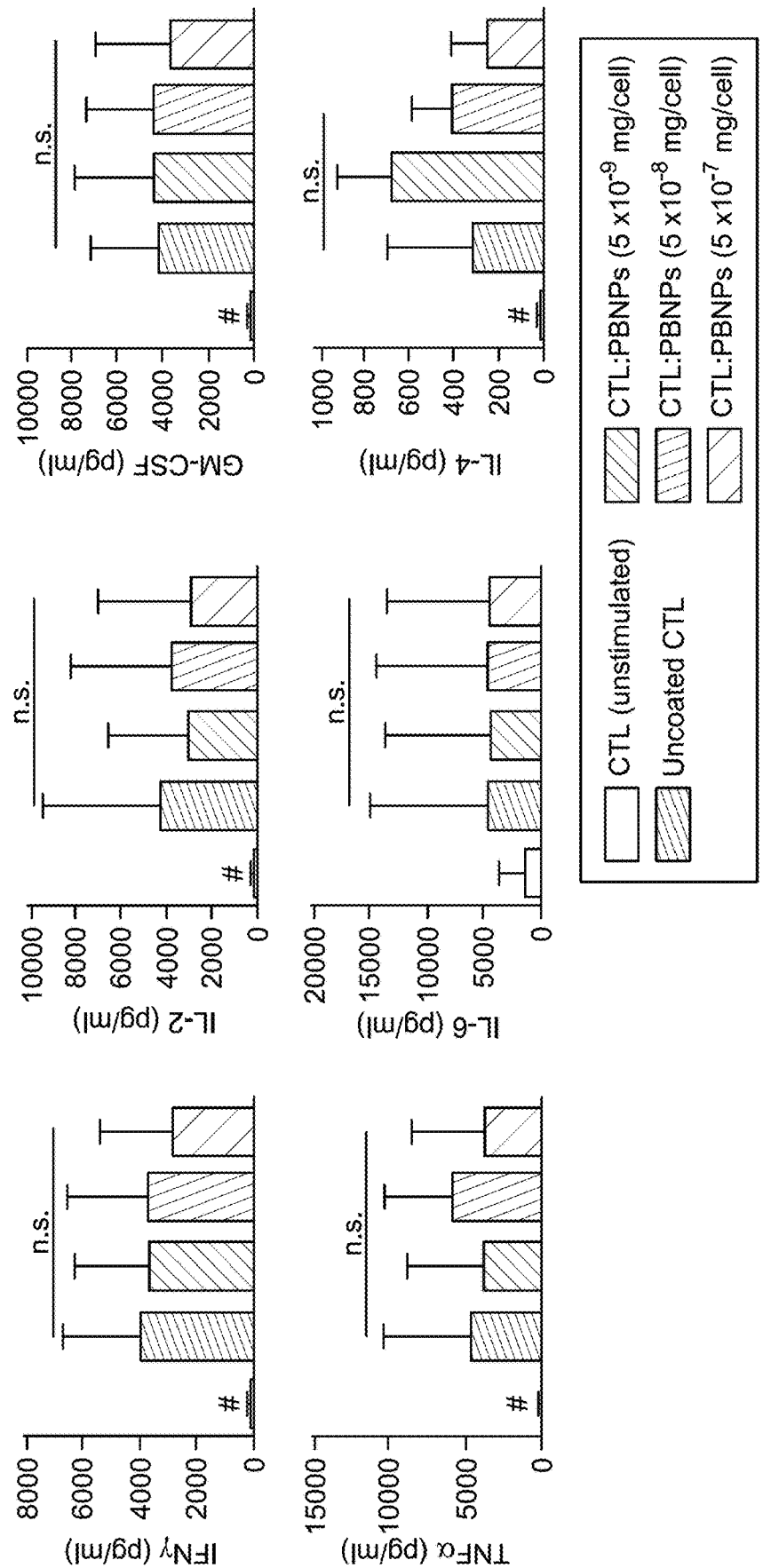
Figure 21:
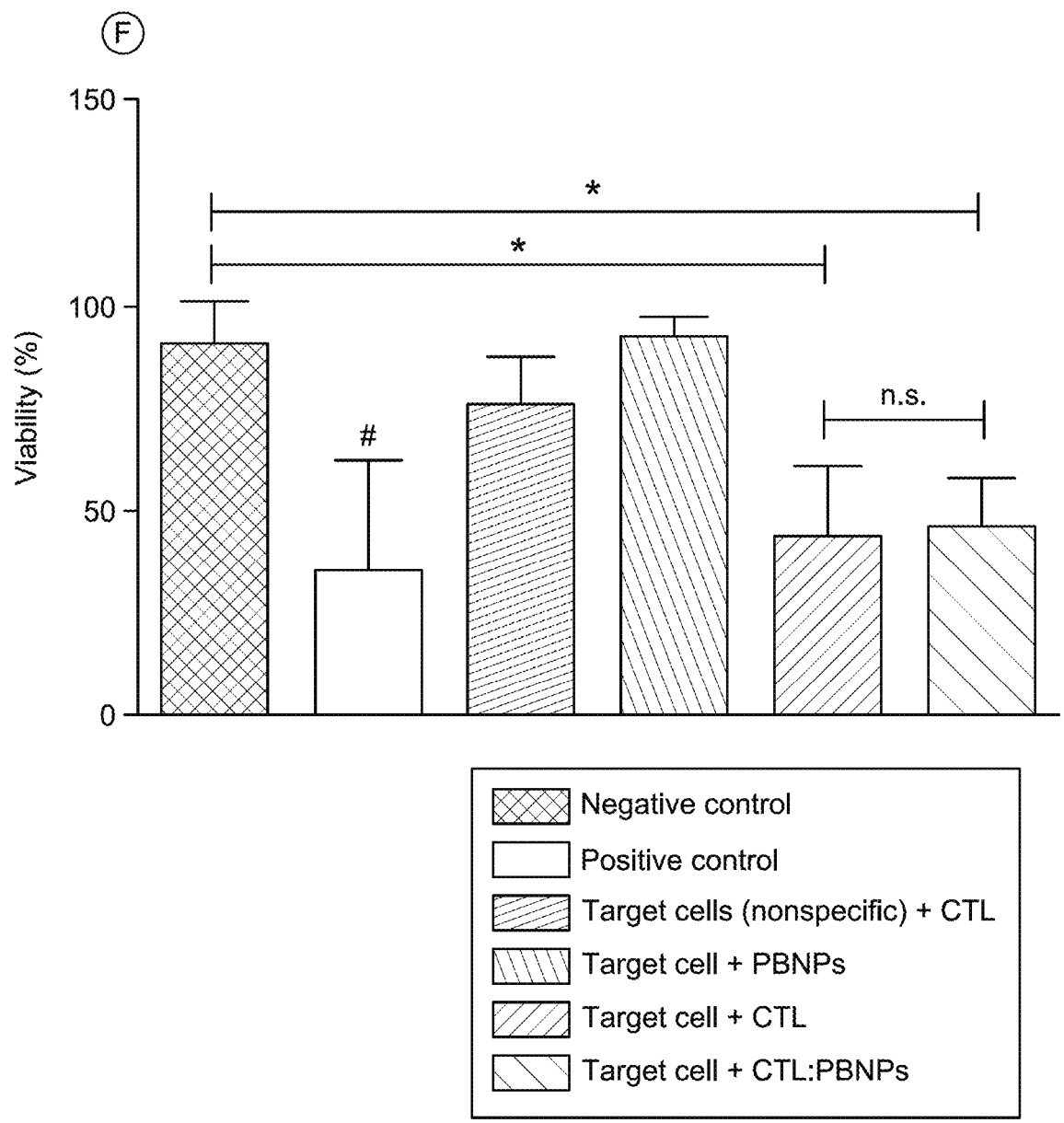

FIG. 21. Prussian blue nanoparticle conjugation does not impact cytotoxic T lymphocyte phenotype or function. (FIGS. 21A & 21B) Representative histograms and aggregate data depicting proliferation of CFSE-labeled T cells following 24 h of antigen-specific stimulation. (FIGS. 21C & 21D) Representative dot plots and aggregate data of CTL phenotype assayed by flow cytometry. PBNP: Prussian blue nanoparticle. (FIG. 21E) Aggregate results of cytokine production by stimulated CTL±PBNP-coating at varying surface nanoparticle concentrations. (FIG. 21F) Viability of EBV+ target cells in response to cytotoxicity mediated by CTL±PBNP coating; n=7. PBNP: Prussian blue nanoparticle.

Figure 22:
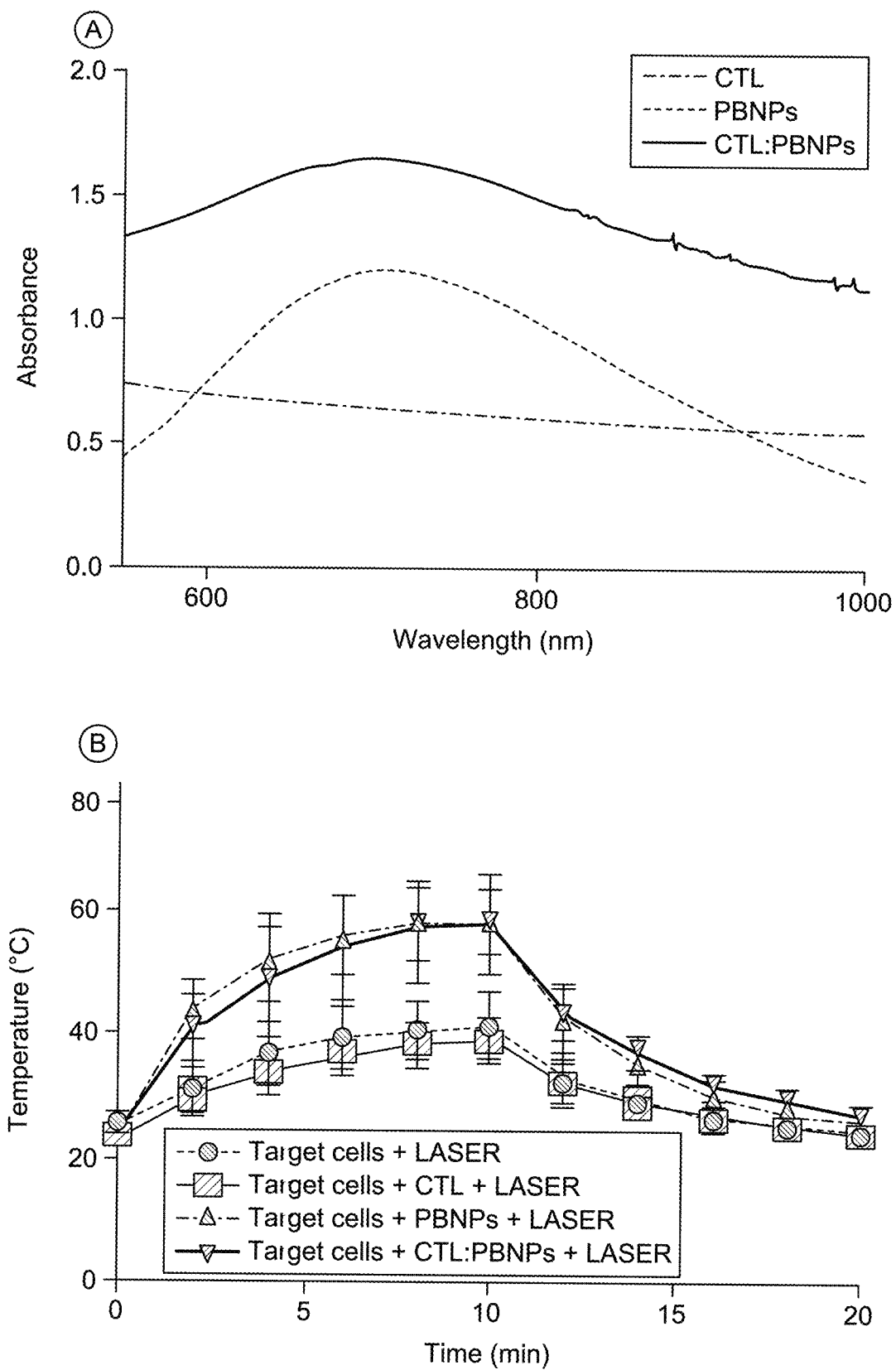
Figure 22:
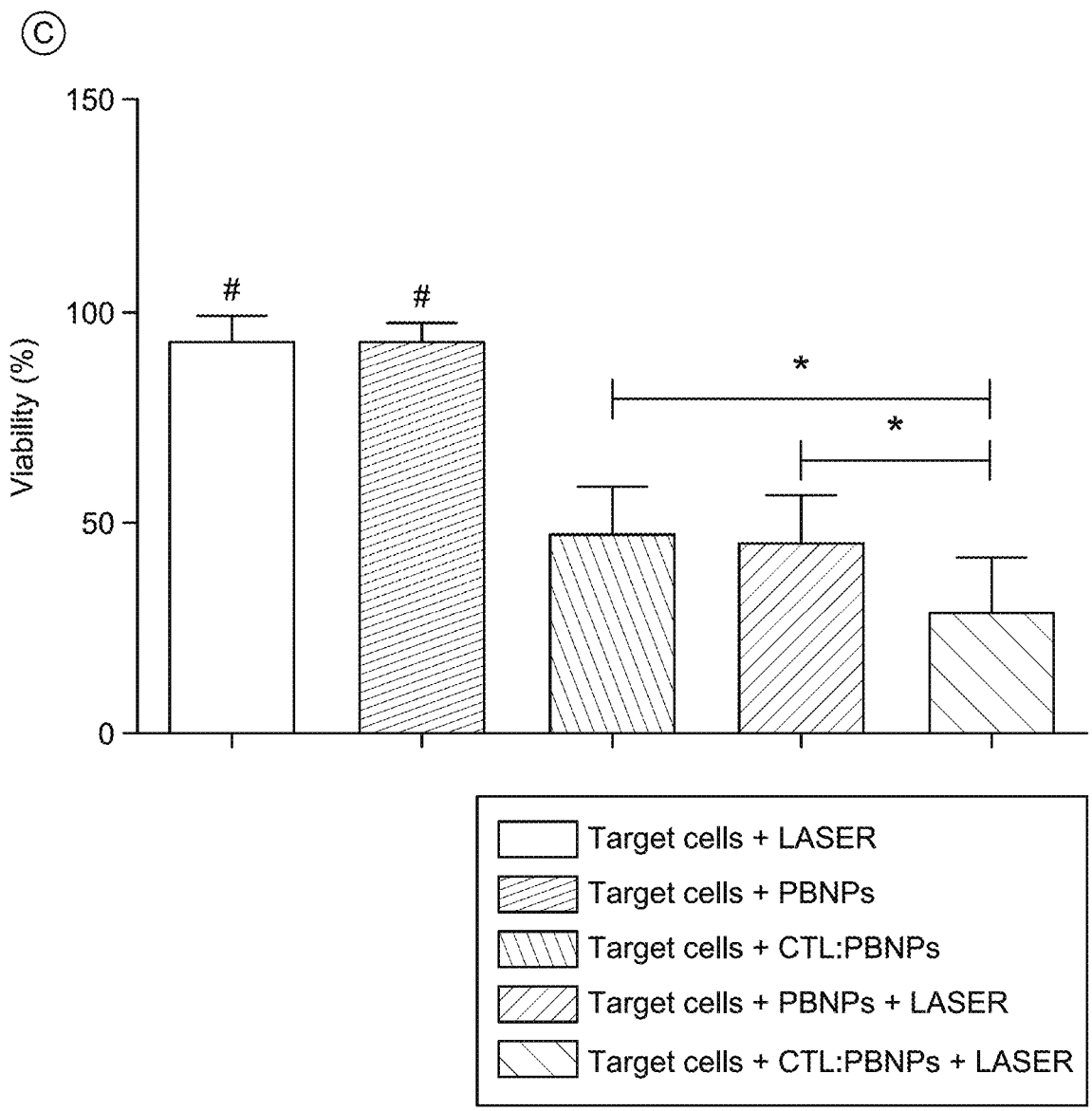
Figure 22:
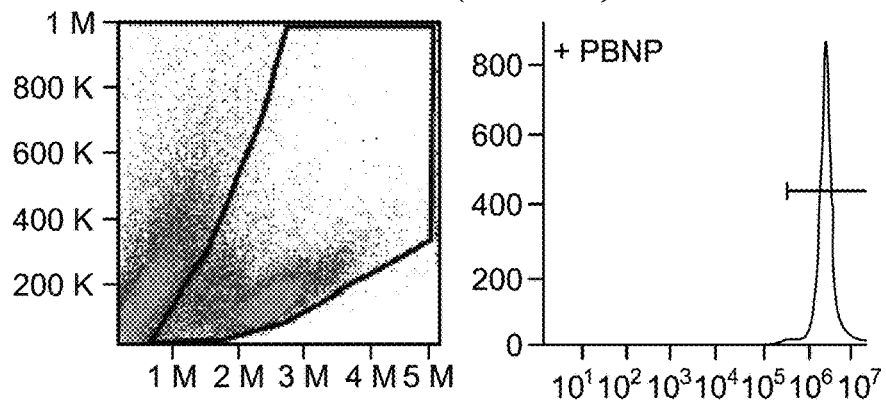
Figure 22:
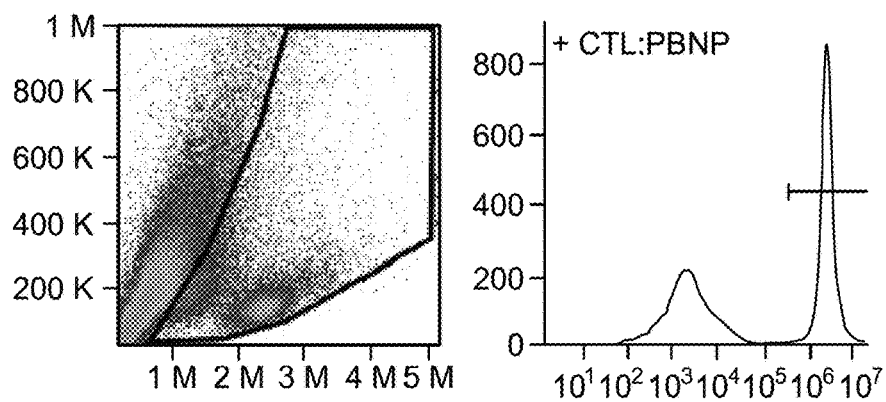
Figure 22:
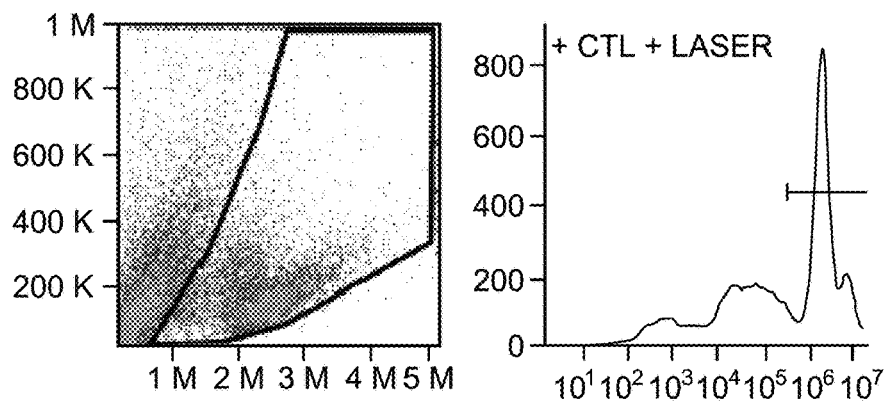
Figure 22:
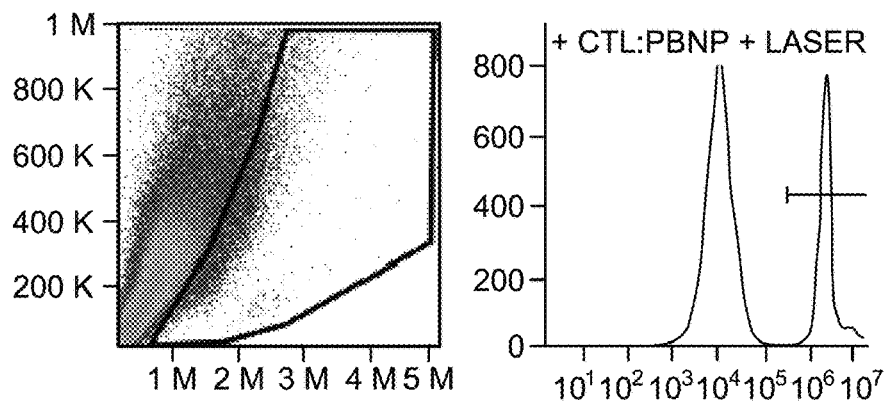

FIG. 22. Prussian blue nanoparticles stably conjugated to cytotoxic T lymphocytes are functional as agents of photothermal therapy. (FIG. 22A) Vis-NIR spectra of CTL, PBNPs and the CTL:PBNPs construct: a peak in 680-720 nm indicates light absorption in the NIR range. (FIG. 22B) Temperature profile of the various groups in response to 10-min exposure to the NIR laser followed by cooling at room temperature. (FIGS. 22C & 22D) Aggregate data depicting target cell viability and representative histograms (with live cell pregating) of labeled target cells in response to co-culture with CTL±PBNPs±laser; n=7. CTL: Cytotoxic T lymphocyte; NIR: Near infrared; PBNP: Prussian blue nanoparticle.

Figure 23:
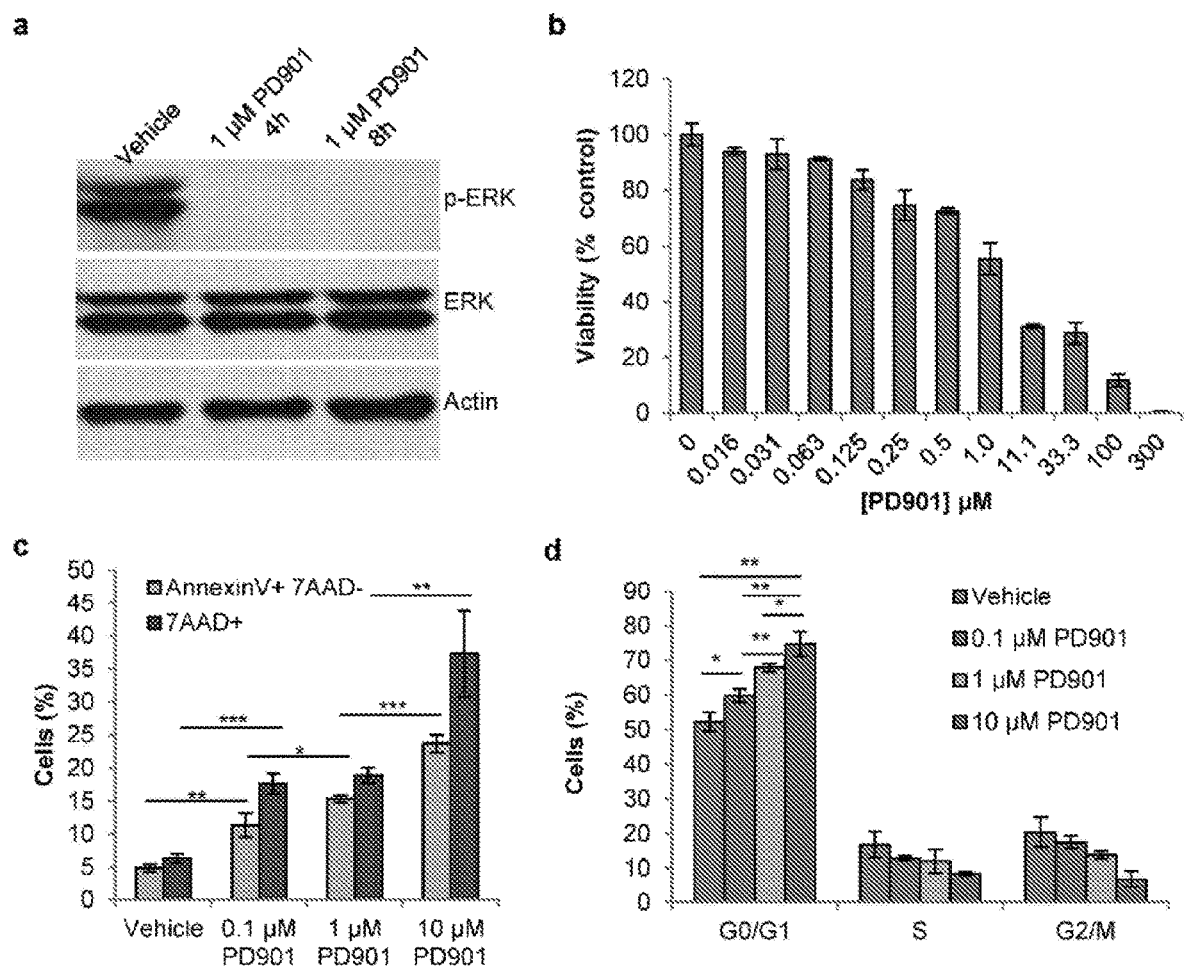

FIG. 23. PD901 effectively treats MPNSTs in vitro by blocking ERK activation. (FIG. 23a) Mouse MPNST (M2) cells exhibit markedly decreased p-ERK protein expression when treated with 1 $\mu$M PD901 for 4 h or 8 h compared to vehicle (DMSO)-treated M2 cells when visualized by a Western blot. (FIG. 23b) M2 cells exhibit decreased viability when treated for 48 h with increasing concentrations of PD901 (IC50=1 $\mu$M). (FIG. 23c) M2 cells treated with 0.1, 1, and 10 $\mu$M PD901 for 24 h undergo cell death via both apoptosis (light blue, Annexin V+7AAD population) and late apoptosis/necrosis (dark blue, 7AAD+population), measured by flow cytometry. (FIG. 23d) M2 cells treated with 0.1, 1, and 10 $\mu$M PD901 for 24 h undergo cell cycle arrest in the G0/G1 phase in a concentration-dependent manner, measured by flow cytometry. Data in all plots expressed as mean±standard deviation (n≥3/group); $*p<0.05$; $p<0.01$; $*p<0.001$. (For interpretation of the references to color in this figure legend, the reader is referred to the web version of Sweeny, et al., Sci. Rep. 6, 37035; doi:10.1038/srep37035 (2016), which is incorporated by reference.)

Figure 24:
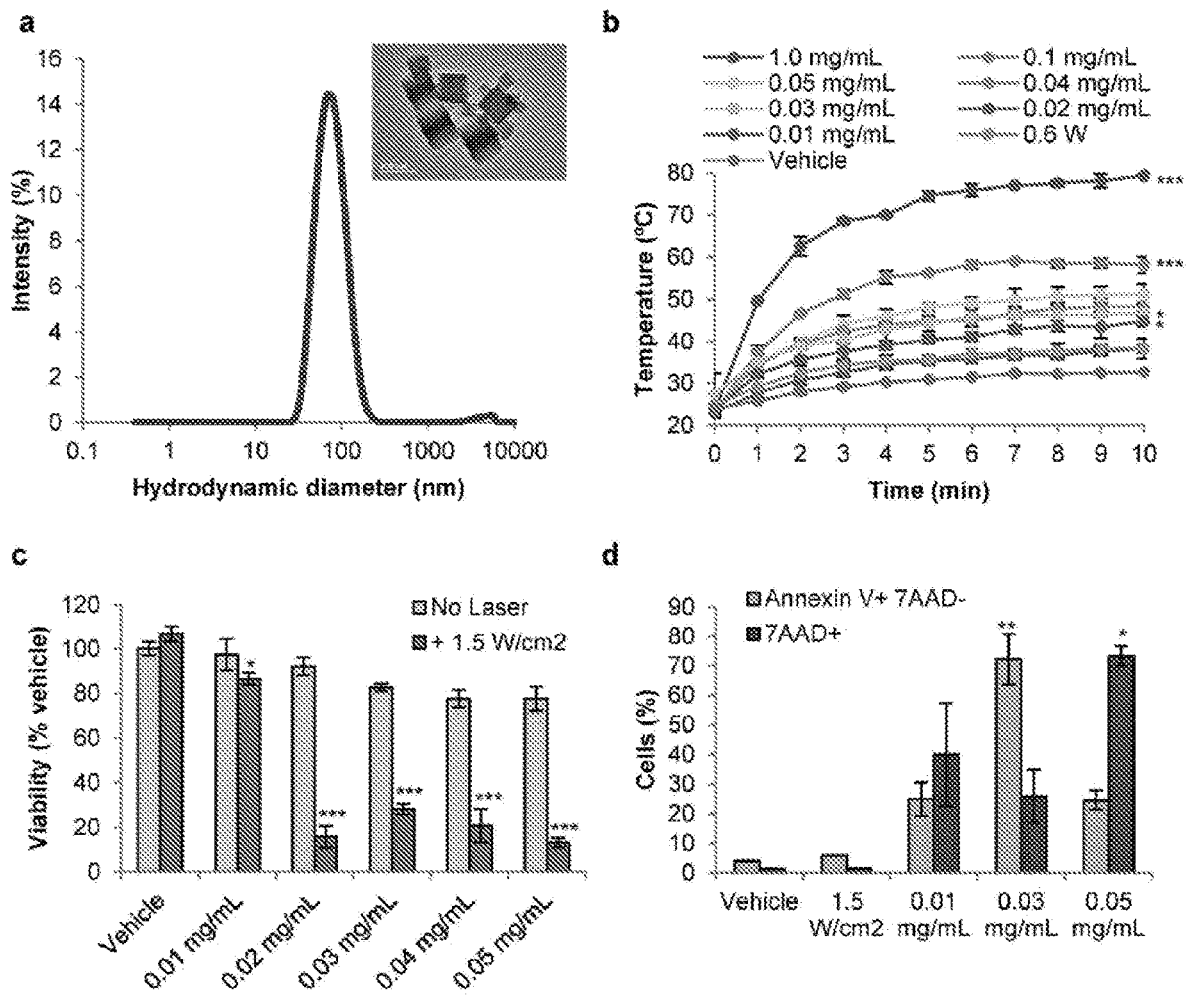

FIG. 24. PBNPs function as effective agents for PTT of MPNSTs in vitro. (FIG. 24a) PBNPs exhibit monodisperse size distributions as measured by dynamic light scattering (mean hydrodynamic diameter=68.1 nm). Inset: PBNPs exhibit their characteristic cubic morphology when visualized using transmission electron microscopy (scale bar=100 nm). (FIG. 24b) PBNPs heat to higher temperatures with increasing concentrations of PBNPs when irradiated with an 808 nm NIR laser at 1.5 W/cm$^2$ for ten minutes; measured at one-minute intervals using a thermocouple. $*p<0.05$; $***p<0.001$; compared to adjacent lower concentration's temperature at 10 minutes. (FIG. 24c) The viability of M2 cells decrease when subject to varying doses of PTT (PBNP concentrations ranging from 0.01 mg/mL to 0.05 mg/mL, with or without 808 nm laser irradiation at 1.5 W/cm$^2$ for ten minutes), measured after 24 h. $*p<0.05$; $***p<0.001$; compared to matched controls. (FIG. 24d) M2 cells treated with various doses of PTT can trigger cell death via apoptosis (light blue, Annexin V+7AAD− population) and/or late apoptosis/necrosis (dark blue, 7AAD+population) depending on the resulting temperature range to which they are heated; quantified by flow cytometry. Data in all plots expressed as mean±standard deviation (n≥3/group). $*p<0.05$; $**p<0.01$; compared to all other samples in group. (For interpretation of the references to color in this figure legend, the reader is referred to the web version of Sweeny, et al., Sci. Rep. 6, 37035; doi:10.1038/srep37035 (2016), which is incorporated by reference.)

Figure 25:
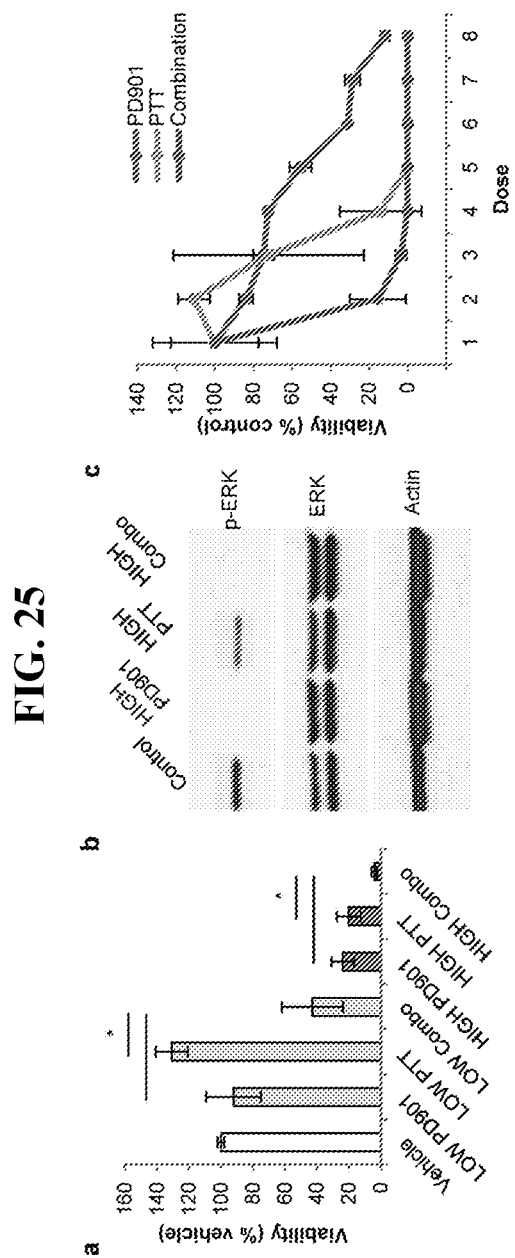

FIG. 25. PD901 and PTT synergistically combine to yield improved treatment outcomes for MPNSTs vitro. (FIG. 25a) M2 cells treated with low and high doses of PD901 and PTT show significantly decreased cell viability in combination therapy (PD901 plus PTT)-treated groups relative to either therapy administered individually under identical conditions after 24 h. LOW PD901: 0.125 $\mu$M; LOW PIT 0.005 mg/mL+1.5 W/cm$^2$ 808 nm laser for 10 minutes; LOW Combo: both LOW PD901+LOW PTT treatments; HIGH PD901: 1.0 $\mu$M; HIGH PTT 0.05 mg/mL+1.5 W/cm$^2$ 808 nm laser for 10 minutes; HIGH Combo: both HIGH PD901+ HIGH PTT treatments. Data expressed as mean±standard deviation (n≥3/group). $*p<0.05$. (FIG. 25b) M2 cells treated with vehicle, HIGH PD901, HIGH PTT, HIGH Combo for 4 h, and subsequently harvested, lysed, and probed for p-ERK, exhibit complete eradication of p-ERK expression in both the PD901 and HIGH Combo groups, and a clear decrease in the HIGH PTT-treated group. Actin was used as a loading control. (c) PD901 synergistically combines with PTT to decrease M2 cell viability in vitro over either treatment alone at equivalent doses. 50,000 M2 cells were treated with increasing doses of PD901, PTT, or combination, and viability was measured after 24 h by CellTiter-Glo viability assay (Promega). Data points represent means±standard deviation; n=3 per group. (For interpretation of the references to color in this figure legend, the reader is referred to the web version of Sweeny, et al., Sci. Rep. 6, 37035; doi:10.1038/srep37035 (2016), which is incorporated by reference.)

Figure 26:
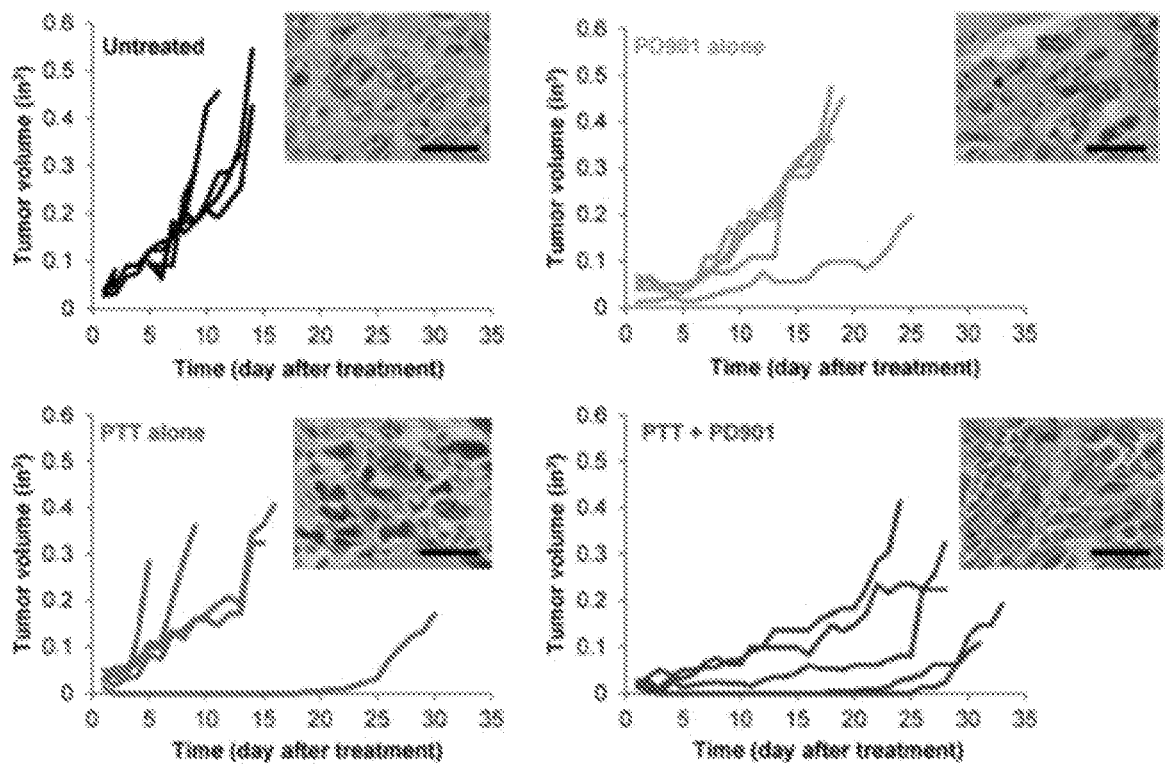
Figure 26:
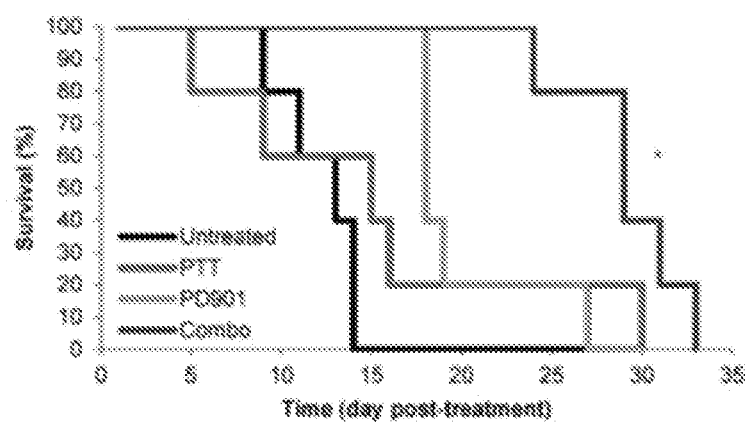

FIG. 26. PD901 and PTT combine to decrease MPNST progression and increase survival in vivo. MPNST bearing B6129SF1/J mice were treated once tumors reached 10 mm in diameter with: no treatment (n=5, black), 5 mg/kg PD901 (n=5, blue), PTT (n=5, red; 1.0 mg/mL PBNPs with 1.5 W/cm$^2$), or PD901+PTT (n=5, purple; both PD901 and PTT treatments). PD901 was administered by oral gavage daily. PBNPs were administered intratumorally and PTT was performed once for ten minutes. Animals were euthanized when tumors reached 20 mm in diameter or showed signs of distress. (FIG. 26a) Tumor progression was measured every day by calipers. Each line represents one mouse. Insets: Tumors were harvested 8 h post-treatment, processed for histology, stained with H&E, and visualized by microscopy; scale bar=20 $\mu$m. (FIG. 26b) Survival is illustrated by a Kaplan-Meier curve. $*p<0.05$ compared to all groups by log-rank test. (For interpretation of the references to color in this figure legend, the reader is referred to the web version of Sweeny, et al., Sci. Rep. 6, 37035; doi:10.1038/srep37035 (2016), which is incorporated by reference.)

DETAILED DESCRIPTION OF THE INVENTION

Definitions

"Prussian blue particle(s) or nanoparticle(s)" refer to particles containing Prussian blue, preferably in an amount and form suitable for administration to a subject during a photothermal treatment. This definition includes but is not limited to the Prussian blue compositions described by U.S. 2014/0271487 which is incorporated by reference.

These particles may contain components a chemical formula of $A_xB_yM_z[M'(CN_6]_a \cdot n(H_2O)$, where A represents at least one of VO" Ca, V, Cr, Mn, Fe, Co, Ni, Cu, In, Ga, Sr, lr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof; B represents at least one of VO" Ca, V, Cr, Mn, Fe, Co, Ni, Cu, In, Ga, Sr, lr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dyand Ho, in any oxidation state and any combination thereof; M represents at least one of VO" Ca, V, Cr, Mn, Fe, Co, Ni, Cu, In, Ga, Sr, lr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dyand Ho, in any oxidation state and any combination thereof; M' represents at least one of VO" Ca, V, Cr, Mn, Fe, Co, Ni, Cu, In, Ga, Sr, lr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof; x is from 0.1 to about 1; Y is from 0 to about 1; z is from 0.1 to about 4; a is from 0.1 to about 4; and n is from 0.1 to about 24.

These particles preferably having an average diameter ranging from about 1 nanometer to about 10 microns or any intermediate value within this range, including 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000 or 10,000 nm.

Advantageously, they exhibit a peak photonic absorbance at a wavelength ranging from about 600, 700, 800, 900, 1,000 m, 1,100 to about 1,200 nm (as well as all intermediate values within this range) by a photothermal conversion process or other mechanism. A nanoparticle preferably converts absorbed incident light having a wavelength ranging from ranging from ranging from about 600, 700, 800, 900, 1,000, 1,100 to about 1,200 nm (as well as all intermediate values within this range) to heat, wherein the amount of heat produced results in an increase in nanoparticle temperature ranging from about 0.1, 0.5, 1, 2, 3, 4, 5, 6, 7, 8, 9, 10, 20, 30, 40, 50, 60, 70, 80, 90 to about 100° C. as well as all intermediate values within this range. A Prussian blue nanoparticle may convent to heat absorbed incident light having a wavelength ranging from ranging from about 600 nm to about 1,200 nm at a photothermal conversion efficiency ranging from about 0.1% to about 90%.

In some embodiments, a Prussian blue nanoparticle is coated, compounded or combined with at least one substance that reduces or prevents degradation of the Prussian blue component, e.g., degradation caused by contact with hydroxyl ions or other reactive components) in blood, plasma or lymph compared to an otherwise identical nanoparticle that is not coated, compounded or combined. In some embodiments, a compounded or coated nanoparticle when introduced in vivo into blood, plasma, CSF, tissue fluid, lymph or other bodily fluids will resist degradation of the Prussian blue component for 1, 2, 3, 4, 5, 6, 7, 8, 9, 10, 15, 30, 60, 120, 180 minutes or other time sufficient for the nanoparticle to come into contact with a cancer, neoplastic or tumor cell or other target cell, and/or for a time sufficient for it to attach or endocytosed by said target cell, and/or for a time sufficient for it to absorb radiation applied during a photothermal treatment.

A Prussian blue nanoparticle may have at least one, two or three protective layer(s) that reduce or prevent contact between the Prussian blue component of the nanoparticle and hydroxyl ions in blood, plasma, lymph or other bodily fluids or components. It may contain or be in the form of a nanoshell, liposome, micelle, or liposome-like synthetic particle. It may comprise a coating, such as a biodegradable, bioprotective, sustained or controlled release coating, or a coating that neutralizes hydroxyl ions or other reactive species thus inhibiting degradation of the Prussian blue component of the nanoparticle. A protective layer may optionally be formulated to be stable at pH 7.0 to 8.0, and preferably stable at a pH 7.3 to 7.5 or stable in blood, plasma or lymph or in mildly alkaline physiological solutions.

Exemplary coatings include, but are not limited to, one or more coatings including ADOGEN® 464, ALKANOL® 6112, BRIJ® 52, BRIJ® 93, BRIJ® S2, BRIJ® S, BRIJ® L4, BRIJ® 010, BRIJ® S10, BRIJ® S20, Ethylenediamine tetrakis(ethoxylate-block-propoxylate) tetrol, IGEPAL® CA-210, IGEPAL® CA-520, IGEPAL® CA-720, IGEPAL® CO-630, IGEPAL® CO-890, IGEPAL® DM-970, MERPOL® DA, MERPOL® HCS, MERPOL® OJ, MERPOL® SE, MERPOL® SH, MERPOL® A, poly(ethylene glycol) sorbitan tetraoleate, poly(ethylene glycol) sorbitol hexaoleate, poly(ethylene glycol), polyethylene-block-poly(ethylene glycol), sorbitan monopalmitate, 2,4,7,9-tetramethyl-5-decyne-4,7-diol ethoxylate, 2,4,7,9-tetramethyl-5-decyne-4,7-diol, TRITON™ N-101, TRITON™ X-100, TRITON™ X-100 reduced, TRITON™ X-114, TRITON™ X-405, reduced, TWEEN® 20, TWEEN® 40, TWEEN® 60, TWEEN® 85, ZONYL® FS-300, ZONYL® FSA, ZONYL® FSN, ZONYL® FSO fluorosurfactant, acrylic acid (AA), 4,4'-azobis(4-cyanopentanoic acid); ACPA), 2,2'-azobisisobutyronitrile (AIBN), sodium bis(2-ethylhexyl) sulfosuccinate (AOT), sodium dihexyl sulfosuccinate (AMA-80), Amphi-Dex, acrylonitrile (AN), bis(2-pyridylmethyl)-octadecylamine (BPMODA), BRIJ® 30 (polyoxyethylene-4-lauryl ether), 1-butyl-3-methylimidazolium hexafluorophosphate ([C4mim]PF6), poly(oxyethylene) octyl phenyl ether (CA897),CMC-A9, carboxymethylated poly(ethylene glycol) (CMPEG), cetyltrimethylammonium bromide (CTAB), cetyltrimethylammonium chloride (CTMA-Cl), didodecyldimethylammonium bromide (DDAB), dodecanoic acid 2-(2-hydroxyethoxy)ethyl ester (DDA-HEEE), decyltrimethylammonioumbromide (DeTAB), dodecyl mercaptane (DDM), dextran ester (Dex-Est), SG1-based difunctional alkoxyamine (DIAMA-Na), dimethyl acetamide (DMAc), dodecyl methacrylate (DMA), (dimethylamino)ethyl methacrylate (DMAEMA), 3-(N,N-dimethylmyristylammonio) (DMMA-PS), dodecyl mercaptane, dodecyltrimethylammonioumbromide (DTAB), methacrylic acid copolymer (EUDRAGIT® L100-55), poly(ethylene-co-butylene)-b-poly(ethylene oxide) (KLE3729), lauryl methacrylate (LMA), monomethoxy-poly(ethylene glycol) (mPEG), monomethoxy-poly(ethylene oxide)-poly(lactic acid) (mPEO-PLA), methyl methacrylate (MMA), octyl trimethyl ammonium bromide (OTAB), polyaniline-poly(styrenesulfonic acid) (PANI-PSS), poly(γ-benzyl-1-glutamate)-b-poly(ethylene oxide) (PBG-PEO), poly(ε-caprolactum) (PCL), poly(oxyethylene)-poly(oxypropylene) copolymer (PE/F68), poly(ethylene oxide) (PEO), poly(ethyleneglycol) (PEG), poly(hydroxyl butyrate) (PHB), poly(heptadecafluorodecylacrylate) (PHDFDA), poly(hydroxyethyl methacrylate) (PHEMA), poly(lactide-fumarate) (PLAF), poly(d,l-lactic acid-co-glycolic acid) (PLGA), poly(lactide-co-glycolide fumarate) (PLGF), poly(l-lactic acid) (PLLA), Pluronic F-108, poly(α,β-1-malic acid) (PMA), poly(methyl methacrylate) (PMMA), poly(N-isopropylacrylamide-co-methacrylic acid) (P(NIPAM-MAA)), poly(ethylene oxide)-poly(propylene oxide) ethylene diamine co-polymer (Poloxamine 908), poly(styrenesulfonic acid) (PSS), poly(trimethylene carbonate) (PTMC), poly(vinyl alcohol) (PVA), sodium 4-(v-acryloyloxyalkyl) oxy benzene sulfonate (SABS), sodium dodecyl sulfate (SDS), sodium lauryl sulfate (SLS), sodiumoctylbenzene sulfonate (SOBS), stearyl methacrylate (SMA), 5-sulfoisophthalic acid dimethyl ester sodium salt modified tetracarboxylic acid-terminated polyester (SMTAPE), sorbitan monopalmitate (SPAN® 40), sorbitan monooleate (SPAN® 80), sorbitane trioleate (SPAN® 85), and sodium persulfate (SPS).

A Prussian blue nanoparticle may contain other ingredients, such as buffers, surfactants, excipients or other active (e.g., drug or biologically active agent) or inactive ingredients.

A Prussian blue nanoparticle may be conjugated or otherwise bound or associated with a targeting agent, such as a T cell or other immunocyte, or may be compounded or coated with at least one agent that targets it to a cell (e.g., to a cancer, tumor or neoplastic cell), tissue or other anatomical site. Targeting agents include antibodies or other ligands that bind to a tumor-associated or tumor-specific antigen, or agents such as biotin, (strep)avidin, or other component that binds to a complementary moiety naturally present on or placed on a target cell, tissue or anatomical site. In some embodiments, a Prussian blue nanoparticle is bi- or multifunctional and can further contain at least one moiety that binds to a cancer, neoplastic or tumor cell, or other target cell, tissue or anatomical site, or to a component of, or substance released from a target cell, tissue or site. The targeting agent may be an antibody, epitope-binding antibody fragment, aptamer, biotin, (strep)avidin, or a natural or exogenous receptor or ligand complementary to a ligand or receptor on a target cell. The Prussian blue nanoparticle may contain one or more chemical groups, substances, coatings or other agents that facilitates endocytosis of the nanoparticle into a target cell.

"Immunocytes" include but are not limited to lymphocytes, such as T and B lymphocytes gamma-delta T-cells, and NK cells, which may recognize specific antigens, such as prion, viral, bacterial, yeast, fungal, parasite, tumor-associated or tumor-specific antigens, or other antigens associated with a particular disease, disorder or condition. Other immunocytes include white blood cells, which may be granulocytes or agranulocytes. Examples of immunocytes include neutrophils, eosinophils, basophils, lymphocytes, monocytes and macrophages. Dendritic cells, microglia, and other antigen-presenting cells are also included within this definition. Immunocytes may be used in an adoptive therapy conjugated or combined with Prussian blue nanoparticles or administered before, concurrently, or after the Prussian blue nanoparticles.

"Immunotherapy" includes therapies mediated by immune system components, such as by antibodies or immunocytes, or by drugs or other agents that stimulate, inhibit or otherwise modulate the immune system. These include immunomodulators, drugs, or substances that affect the immune system; including but not limited to antibodies (e.g., anti-tumor antigen antibodies), epitope-binding portions of an antibody, antibody conjugates including cytotoxic conjugates, radiological agents, other tumor-targeted agents, cytokines, chemokines, interferons, interleukins, colony stimulating factors, drugs or other agents that modulate immune responses, immune cells or engineered cells that interact with, recognize, or bind to target cells. An immunomodulator, drug or other substance may be bound to, incorporated into, or otherwise associated with a Prussian blue nanoparticle.

Immunotherapy may involve the administration of one or more chemokines or cytokines including those described at https://en.wikipedia.org/wiki/Cytokine (last accessed Mar. 7, 2017) or https://en.wikipedia.org/wiki/Chemokine (last accessed Mar. 7, 2017) both of which are incorporated by reference. It may also involve antibody-mediated therapy, including but not limited to check point inhibitors. Such antibodies may include anti-CTLA4, anti-GD2, anti-PD1, anti-PDL1, anti-CD47, anti-CD20, and/or anti-CD52 antibodies.

"Combined Immunotherapy" refers to a combination of treatment with Prussian blue nanoparticles and at least one immunotherapy as described herein. Such a combined immunotherapy may reduce tumor burden, tumor metastasis, or tumor growth rate by 5, 10, 15, 20, 25, 30, 35, 40, 45, 50, 55, 60, 65, 70, 75, 80, 85, 90, 95, 100, 150, 200, 300, 400, 500% or more compared to a subject treated a nanoparticle-based therapy alone or with immunotherapy alone, or by more than the sum of separate treatments with the nanoparticle or immunotherapy or that increases mean survival at 1, 2, 3, 4, 5, 6, 7, 8, 9, 10, 11, 12, 18, 24, 36, 48, or 60 months compared to the survival rate of subject(s) treated with nanoparticle-based therapy alone or with immunotherapy alone, or more than the sum of separate treatments with nanoparticles or immunotherapies. Similar reductions in the progression or symptoms of other non-tumor diseases, disorders or conditions, may also result from a combined immunotherapy directed to the non-tumor disease, disorder or condition, including persistent or recurring infectious diseases. Such non-cancerous conditions include hyperplasia, wart, or other condition associated with abnormal cell proliferation or with infection by a prion, virus, bacterium, fungus, yeast, or parasite.

It may reduce tumor recurrence by 5, 10, 15, 20, 25, 30, 35, 40, 45, 50, 55, 60, 65, 70, 75, 80, 85, 90, 95, 100, 150, 200, 300, 400, 500% or more compared to a subject treated a nanoparticle-based therapy alone or with immunotherapy alone, or more than the sum of separate treatments with a nanoparticle-based therapy alone or with immunotherapy alone. Similar reductions in the recurrence or relapse of other non-tumor diseases, disorders or conditions, may also result from a combined immunotherapy directed to the non-tumor disease, disorder or condition, including persistent or recurring infectious diseases. Such non-cancerous conditions include hyperplasia, wart, or other condition associated with abnormal cell proliferation or with infection by a prion, virus, bacterium, fungus, yeast, or parasite.

A combined immunotherapy may comprise treatment with Prussian blue nanoparticles and one or more of the immunotherapies described by Galuzzi, et al., *Classification of current anticancer immunotherapies*, Oncotarget 5(24): 12472-12508 (2014) which is incorporated by reference in its entirety.

"Checkpoint inhibitors" include, but are not limited to anti-CTLA-4 checkpoint inhibition and including inhibitors of PD-1 and PD-L1. Examples of such inhibitors include ipilimuma, nivolumab, pembrolizumab and atezolizumab. Modulation of immune checkpoints affect immune system functioning and can be stimulatory or inhibitory.

"MEK inhibitor" is a chemical or drug that inhibits the mitogen-activated protein kinase enzymes MEK1 and/or MEK2. These include, but are not limited to, PD 901, Trametinib (GSK 1120212), Cobimetinib or XL518, Binimetinib (MEK 162, ARRY-162), and Selumetinib.

"Cancers, neoplasms, tumors, or malignancies" include but are not limited to adult cancer, malignancy, neoplasm, or tumor or an associated condition selected from the group consisting of Adrenocortical Carcinoma, AIDS-Related Cancer, Anal Cancer, Anemia associated with malignancy or cancer treatment, Angiosarcoma, Astrocytoma, Basal Cell Carcinoma, Biliary Cancer, Bladder Cancer, Bone Cancer, Brain Metastasis, Brain Tumor, Breast Cancer, Carcinoid, Cervical Cancer, Chondrosarcoma, Coagulation Disorders associated with malignancy or cancer treatment, Colon Cancer, Craniopharyngioma, Desmoid Tumor, Ductal Carcinoma in Situ (DCIS), Endometrial Cancer, Esophageal Cancer, Fibrosarcoma, Gastric (Stomach) Cancer, Gastrointestinal Carcinoid Tumor, Gastrointestinal Stromal Tumor (GIST), Gestational Trophoblastic Tumor, Glioblastoma, Glioma, Histiocytosis, Kidney Cancer, Langerhans Cell Histiocytosis, Laryngeal Cancer, Leiomyosarcoma, Leptomeningeal Cancer, Acute Lymphoblastic Leukemia (ALL), Acute Myeloid Leukemia (AML), Chronic Lymphocytic leukemia (CLL), Chronic Myelogenous Leukemia (CML), Liver Cancer, non-small cell lung cancer, small cell lung cancer, Burkitt Lymphoma, Hodgkin Lymphoma, Non-Hodgkin Lymphoma, Primary CNS Lymphoma, Melanoma, Meningioma, Merkel Cell Carcinoma, Mesothelioma, Molar Pregnancy, Monoclonal Gamopathy of Undetermined Significance (M-GUS), Multiple Myeloma, Myelodysplastic Syndromes, Myeloproliferative Disorder, Nasopharyngeal Cancer, Neuroblastoma, Neurofibrosarcoma, Oligodendroglioma, Oropharyngeal Cancer, Osteosarcoma, Ovarian Cancer, Pancreatic Cancer, Parathyroid Cancer, Penile Cancer, Pineal Gland Parenchymal Tumor, Pituitary Adenoma, Prostate Cancer, Rectal Cancer, Renal Cell Cancer, Salivary Gland Cancer, Epithelioid Sarcoma, Ewing Sarcoma, Kaposi's Sarcoma, Soft Tissue Sarcoma, Synovial Sarcoma, Uterine Sarcoma, Skin Cancer, Testicular Cancer, Vaginal Cancer, Vulvar Cancer, or Waldenström's Macroglobulinemia; or metastasis thereof.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−100/% of the stated value (or range of values), +/−15% of the stated value (or range of values), +/−20% of the stated value (or range of values), etc. Any numerical range recited herein is intended to include all sub-ranges subsumed therein.

The term "biocompatible" refers to a substance that is substantially non-toxic to a subject. When "biocompatible" is used in reference to a biologically compatible sample or explant, as described herein, "biocompatible" refers to an artificial or exogenous sample or explant that is implanted into a patient and is non-toxic to that patient. Most embodiments of the invention require the use of biocompatible Prussian blue and immunotherapeutic components.

"Biodegradable" is generally referred to herein as a material that will erode to soluble species or that will degrade under physiologic conditions to smaller units or chemical species that are, themselves, non-toxic (biocompatible) to the subject and capable of being metabolized, eliminated, or excreted by the subject. In some embodiments, a tissue according to the invention may be contacted with, or have incorporated on or into it a biodegradable material. Most embodiments of the invention require the use of biodegradable Prussian blue and immunotherapeutic components.

Modes of administration. A combined therapy may be administered by any suitable mode of application, e.g. intravenously, (i.v.), intraperitoneally (i.p.), intramuscularly (i.m.), intranasally, orally, subcutaneously (s.c.), intratumorally, in situ (e.g., at an open surgical site), etc. and in any suitable delivery device (O'Hagan et al., Nature Reviews, Drug Discovery 2 (9), (2003), 727-735). The Prussian blue and immunotherapeutic components may be administered by the same or different modes, for example, the Prussian blue nanoparticles may be injected into a target site and an immunotherapeutic immunocyte or antibody administered intravenously. Means and methods for obtaining respective formulations are known to the person skilled in the art (see e.g. "Handbook of Pharmaceutical Manufacturing Formulations", Sarfaraz Niazi, CRC Press Inc, 2004).

Light/Irradiation Sources/Lasers. Those of skill in the art can select an appropriate radiation source for photothermal therapy. An example of such a source is an NIR laser spanning about 700, 800, 900, 1,000, 1,100, 1,200, 1,300, 1,400, 1,500, 1,600, 1,700, 1,800, 1,900, 2000 nm wavelengths with powers ranging from about 0.01, 0.05, 0.1, 0.5, 1, 2, 3, 4-5 W/cm$^2$ or equivalents thereof. These ranges include all intermediate values and subranges.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Non-limiting embodiments of the invention include the following compositions and methods.

EMBODIMENTS

1. A combined method for treating a subject comprising.
    (i) administering a Prussian blue nanoparticle, a composition containing the nanoparticle, or a cell comprising the nanoparticle, to a subject in need thereof and
    (ii) photothermally treating the subject; and
    (iii) treating the subject with at least one other immunotherapy; wherein, optionally, said method comprises administering an antigen-specific T cell comprising Prussian blue nanoparticles.
2. The combined method of embodiment 1, wherein the Prussian blue nanoparticles comprise Prussian blue 3. The combined method of any one of embodiments 1 or 2 wherein the Prussian blue nanoparticle consists essentially of Prussian blue.

4. The combined method of any one of embodiments 1-3, wherein the Prussian blue nanoparticle comprises Prussian blue in an amount sufficient to permit it to participate in said photothermal treatment.

5. The combined method of any one of embodiments 1-4, wherein the Prussian blue comprises, consists essentially of, or consists of a compound or composition having a chemical formula of:

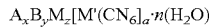

wherein:
A represents at least one of VO" Ca, V, Cr, Mn, Fe, Co, Ni, Cu, In, Ga, Sr, lr, Nb, Li, Na, K, Rb, Cs, Fr, TI, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;
B represents at least one of VO" Ca, V, Cr, Mn, Fe, Co, Ni, Cu, In, Ga, Sr, lr, Nb, Li, Na, K, Rb, Cs, Fr, TI, Mo, Ru, Rh, Pd, Ag, Cd, In, Lu, Ba, Hf, Ta, W, Os, Pt, Hg, La, Eu, Gd, Tb, Dyand Ho, in any oxidation state and any combination thereof;
M represents at least one of VO" Ca, V, Cr, Mn, Fe, Co, Ni, Cu, In, Ga, Sr, lr, Nb, Li, Na, K, Rb, Cs, Fr, TI, Mo, Ru, Rh, Pd, Ag, Cd, In, Lu, Ba, Hf, Ta, W, Os, Pt, Hg, La, Eu, Gd, Tb, Dyand Ho, in any oxidation state and any combination thereof;
M' represents at least one of VO" Ca, V, Cr, Mn, Fe, Co, Ni, Cu, In, Ga, Sr, Ir. Nb, Li, Na, K, Rb, Cs, Fr, TI, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;
x is from 0.1 to about 1;
Y is from 0 to about 1;
z is from 0.1 to about 4;
a is from 0.1 to about 4; and
n is from 0.1 to about 24.

6. The combined method of any one of embodiments 1-5, wherein the Prussian blue component comprises, consists essentially of, or consists of any one or more of the Prussian blue compounds disclosed by U.S. 2014/0271487 which is incorporated by reference.

7. The combined method of any one of embodiments 1-6, wherein the nanoparticle has an average diameter ranging from about 1 nanometer to about 10 microns.

8. The combined method of any one of embodiments 1-7, wherein the nanoparticle exhibits peak photonic absorbance at a wavelength ranging from about 600 nm to about 1,200 nm.

9. The combined method of any one of embodiments 1-8, wherein the nanoparticle converts to heat absorbed incident light having a wavelength ranging from ranging from about 600 nm to about 1,200 nm by a photothermal conversion process or other mechanism.

10. The combined method of any one of embodiments 1-9, wherein the nanoparticle converts to heat absorbed incident light having a wavelength ranging from ranging from about 600 nm to about 1,200 nm, wherein the amount of heat produced results in an increase in nanoparticle temperature ranging from 0.1 to 100° C.

11. The combined method of any one of embodiments 1-10, wherein the nanoparticle converts to heat absorbed incident light having a wavelength ranging from ranging from about 600 nm to about 1,200 nm at a photothermal conversion efficiency ranging from about 0.1% to about 90%.

12. The combined method of any one of embodiments 1-11, wherein the nanoparticle is coated, compounded or combined with at least one substance that reduces or prevents degradation of the Prussian blue component (e.g., degradation caused by contact with hydroxyl ions or other reactive components) in blood, plasma or lymph compared to an otherwise identical nanoparticle that is not coated, compounded or combined.

13. The combined method of any one of embodiments 1-12, wherein the nanoparticle when introduced in vivo into blood, plasma, CSF, tissue fluid, lymph or other bodily fluids substantially prevents degradation of the Prussian blue component for 1, 2, 3, 4, 5, 6, 7, 8, 9, 10, 15, 30, 60, 120, 180 minutes or other time sufficient for the nanoparticle to come into contact with a cancer, neoplastic or tumor cell or other target cell; and optionally for a time sufficient for it to attach or endocytosed by said target cell, and optionally for a time sufficient for it to absorb radiation applied during a photothermal treatment. The methods described herein may be practice in conjunction with surgical debulking of a tissue, surgical exposure of a tissue, or other techniques to facilitate exposure of target tissue to radiation inducing photothermal effects or to agents used in an immunotherapy.

14. The combined method of any one of embodiments 1-13, wherein the nanoparticle comprises at least one, two or three protective layer(s) that reduces or prevents contact between the Prussian blue component of the nanoparticle and hydroxyl ions in blood, plasma or lymph.

15. The combined method of any one of embodiments 1-14, wherein the nanoparticle comprises a nanoshell, liposome, micelle, or liposome-like synthetic particle.

16. The combined method of any one of embodiments 1-15, wherein the nanoparticle comprises a coating.

17. The combined method of any one of embodiments 1-16, wherein the nanoparticle comprises a coating selected from the group consisting of a polymer that comprises, consists essentially of, or consists of ADOGEN® 464, ALKANOL® 6112, BRIJ® 52, BRIJ® 93, BRIJ® S2, BRIJ® S, BRIJ® L4, BRIJ® 010, BRIJ® S10, BRIJ® S20, Ethylenediamine tetrakis(ethoxylate-block-propoxylate) tetrol, IGEPAL® CA-210, IGEPAL® CA-520, IGEPAL® CA-720, IGEPAL® CO-630, IGEPAL® CO-890, IGEPAL® DM-970, MERPOL® DA, MERPOL® HCS, MERPOL® OJ, MERPOL® SE, MERPOL® SH, MERPOL® A, poly(ethylene glycol) sorbitan tetraoleate, poly (ethylene glycol) sorbitol hexaoleate, poly(ethylene glycol), polyethylene-block-poly(ethylene glycol), sorbitan monopalmitate, 2,4,7,9-tetramethyl-5-decyne-4,7-diol ethoxylate, 2,4,7,9-tetramethyl-5-decyne-4,7-diol, TRITON™ N-101, TRITON™ X-100, TRITON™ X-100 reduced, TRITON™ X-114, TRITON™ X-405, reduced, TWEEN® 20, TWEEN® 40, TWEEN® 60, TWEEN® 85, ZONYL® FS-300, ZONYL® FSA, ZONYL® FSN, ZONYL® FSO fluorosurfactant, acrylic acid (AA), 4,4'-azobis(4-cyanopentanoic acid); ACPA), 2,2'-azobisisobutyronitrile (AIBN), sodium bis(2-ethylhexyl) sulfosuccinate (AOT), sodium dihexyl sulfosuccinate (AMA-80), Amphi-Dex, acrylonitrile (AN), bis(2-pyridylmethyl)-octadecylamine (BPMODA), BRIJ® 30 (polyoxyethylene-4-lauryl ether), 1-butyl-3-methylimidazolium hexafluorophosphate ([C4mim]PF6), poly(oxyethylene) octyl phenyl ether (CA897),CMC-A9, carboxymethylated poly(ethylene glycol) (CMPEG), cetyltrimethylammonium bromide (CTAB), cetyltrimethylammonium chloride (CTMA-Cl), didodecyldimethylammonium bromide (DDAB), dodecanoic acid 2-(2-hydroxyethoxy)ethyl ester (DDA-HEEE), decyltrimethylammonioumbromide (DeTAB), dodecyl mercaptane (DDM), dextran ester (DexEst), SG1-based difunctional alkoxyamine (DIAMA-Na), dimethyl acetamide (DMAc), dodecyl methacrylate (DMA), (dimethylamino) ethyl methacrylate (DMAEMA), 3-(N,N-dimethylmyristylammonio) (DMMA-PS), dodecyl mercaptane, dodecyltrimethylammonioumbromide (DTAB), methacrylic acid copolymer (EUDRAGIT® L100-55), poly(ethylene-co-butylene)-b-poly(ethylene oxide) (KLE3729), lauryl methacrylate (LMA), monomethoxy-poly(ethylene glycol) (mPEG), monomethoxy-poly(ethylene oxide)-poly(lactic acid) (mPEO-PLA), methyl methacrylate (MMA), octyl trimethyl ammonium bromide (OTAB), polyaniline-poly(styrenesulfonic acid) (PANI-PSS), poly(γ-benzyl-1-glutamate)-b-poly(ethylene oxide) (PBG-PEO), poly(ε-caprolactum) (PCL), poly(oxyethylene)-poly(oxypropylene) copolymer (PE/F68), poly(ethylene oxide) (PEO), poly(ethyleneglycol) (PEG), poly(hydroxyl butyrate) (PHB), poly(heptadecafluorodecylacrylate) (PHDFDA), poly(hydroxyethyl methacrylate) (PHEMA), poly(lactide-fumarate) (PLAF), poly(d,l-lactic acid-co-glycolic acid) (PLGA), poly(lactide-co-glycolide fumarate) (PLGF), poly(l-lactic acid) (PLLA), Pluronic F-108, poly(α,β-1-malic acid) (PMA), poly(methyl methacrylate) (PMMA), poly(N-isopropylacrylamide-co-methacrylic acid) (P(NIPAM-MAA)), poly(ethylene oxide)-poly(propylene oxide) ethylene diamine co-polymer (Poloxamine 908), poly(styrenesulfonic acid) (PSS), poly(trimethylene carbonate) (PTMC), poly(vinyl alcohol) (PVA), sodium 4-(v-acryloyloxyalkyl) oxy benzene sulfonate (SABS), sodium dodecyl sulfate (SDS), sodium lauryl sulfate (SLS), sodiumoctylbenzene sulfonate (SOBS), stearyl methacrylate (SMA), 5-sulfoisophthalic acid dimethyl ester sodium salt modified tetracarboxylic acid-terminated polyester (SMTAPE), sorbitan monopalmitate (SPAN® 40), sorbitan monooleate (SPAN® 80), sorbitane trioleate (SPAN® 85), and sodium persulfate (SPS).

18. The combined method of any one of embodiments 1-17, wherein the nanoparticle comprises at least one buffer, preferably in a controlled-released form or as a coating that neutralizes hydroxyl ions or other reactive species thus inhibiting degradation of the Prussian blue component of the nanoparticle.

19. The combined method of any one of embodiments 1-18, wherein the nanoparticle comprises at least one protective layer that reduces or prevents contact between the nanoparticle and hydroxyl ions in blood, plasma or lymph, wherein, optionally, said protective layer is stable at pH 7.0 to 8.0, and preferably stable at a pH 7.3 to 7.5.

20. The combined method of any one of embodiments 1-19, wherein the nanoparticle further comprises at least one natural or synthetic polymer coating that prevents substantial degradation of the Prussian blue component while in blood, plasma or lymph or mildly alkaline physiological solutions.

21. The combined method of any one of embodiments 1-20, wherein the nanoparticle further comprises at least one agent that targets it to a cell (e.g., to a cancer, tumor or neoplastic cell), such as an antibody or other ligand that binds to a tumor-associated or tumor-specific antigen, or such as biotin, (strep)avidin, or other component that binds to a complementary moiety naturally present on or placed on a target cell.

22. The combined method of any one of embodiments 1-21, wherein the nanoparticle is bifunctional or multifunctional, wherein said nanoparticle:

exhibits peak photonic absorbance at a wavelength suitable for photothermal therapy, such as at a wavelength ranging from about 600 nm to about 1,200 nm, and/or specifically attaches to or is endocytosed by a tumor, cancer, malignant, or neoplastic cell or other target cell, and/or specifically attaches to a cellular component of the immune system, such as to a T-cell or macrophage; and/or comprises at least one receptor, ligand or other moiety that interacts with at least one component of an immune system of a subject to which said nanoparticle is administered, such as with a T-cell or macrophage.

23. The combined method of any one of embodiments 1-22 wherein the nanoparticle is bi- or multifunctional and that further comprises at least one moiety that binds to a cancer, neoplastic or tumor cell, or other target cell, or to a component of, or substance released from a target cell, wherein said moiety may be an antibody, epitope-binding antibody fragment, aptamer, biotin, (strep)avidin, or a natural or exogenous receptor or ligand complementary to a ligand or receptor on a target cell.

24. The combined method of any one of embodiments 1-23, wherein the nanoparticle is bi- or multifunctional and that further comprises at least one moiety that binds to a non-malignant cell or platelet, such as a T-cell, NK-cell, B-cell, macrophage, monocyte, microglia, Mast cell, granulocyte, or dendritic cell wherein said moiety may be an antibody, epitope-binding antibody fragment, aptamer, or a receptor or ligand complementary to a ligand or receptor on a target cell, wherein said moiety may be an antibody, epitope-binding antibody fragment, aptamer, biotin, (strep)avidin, or a receptor or ligand complementary to a ligand or receptor on the non-malignant cell or platelet.

25. The combined method of any one of embodiments 1-24, wherein the Prussian blue nanoparticle further comprises one or more chemical groups, substances, coatings or other agents that interacts with a host immune system including but not limited to a chemokine, colony stimulating factor, interferon, interleukin, TNF, or other cytokine, an antibody or antibody fragment, an aptamer, a sense or antisense oligonucleotide, or an immune cell (including but not limited to a T-cell, NK-cell, B-cell, macrophage, monocyte, microglia, Mast cell, granulocyte, or dendritic cell), for example, an immunomodulator that induces or facilitates an immune response that affects the target cell, such as induction of an immunotherapeutic response that inhibits the growth of, metastasis of, or that destroys a cancer, malignant, neoplastic, or tumor cell.

26. The combined method of any one of embodiments 1-25, wherein the Prussian blue nanoparticle further comprises one or more chemical groups, substances, coatings or other agents that facilitates endocytosis of the nanoparticle into a target cell.

27. The combined method of any one of embodiments 1-26, wherein the at least one other immunotherapy comprises treating the subject with at least one immunomodulator, drug, or substance that modulates the immune system; including but not limited antibodies (e.g., anti-tumor antigen antibodies), epitope-binding portions of an antibody, antibody conjugates including cytotoxic conjugates, radiological agents, other tumor-targeted agents, cytokines, chemokines, interferons, interleukins, colony stimulating factors, drugs or other agents that modulate immune responses, immune cells or engineered cells that interact with, recognize, or bind to target cells; wherein, optionally, said at least one other immunotherapy may be mediated by an immunomodulator, drug or substance that is covalently- or non-covalently associated with the nanoparticle.

28. The combined method of any one of embodiments 1-27, wherein the at least one other immunotherapy comprises treating the subject with at least one chemokine or other cytokine.

29. The combined method of any one of embodiments 1-28, wherein the at least one other immunotherapy comprises treating the subject with at least one colony stimulating factor.

30. The combined method of any one of embodiments 1-29 wherein the at least one other immunotherapy comprises treating the subject with at least one interferon.

31. The combined method of any one of embodiments 1-30, wherein the at least one other immunotherapy comprises treating the subject with at least one interleukin.

32. The combined method of any one of embodiments 1-31, wherein the at least one other immunotherapy comprises treating the subject with at least one TNF or other apoptosis-inducing cytokine.

33. The combined method of any one of embodiments 1-32 wherein the at least one other immunotherapy comprises treating the subject with at least one an antibody or antibody fragment, such as an antibody that binds to a tumor- or cancer-associated antigen, or such as an antibody that modulates an immune response to a cancer, neoplasm or tumor.

34. The combined method of any one of embodiments 1-33, wherein the at least one other immunotherapy comprises treating the subject with at least one an aptamer, sense oligonucleotide, or antisense oligonucleotide.

35. The combined method of any one of embodiments 1-34, wherein the at least one other immunotherapy comprises treating the subject with a cell, such as an autologous or tissue-matched immunocyte.

36. The combined method of any one of embodiments 1-35, wherein the at least one other immunotherapy comprises treating the subject a T-cell, NK-cell, B-cell, macrophage, monocyte, microglia, Mast cell, granulocyte, or dendritic cell.

37. The combined method of any one of embodiments 1-37, wherein the at least one other immunotherapy comprises treating the subject with at least one or more agent(s) selected from the group consisting of a chemokine, cytokine, oligodeoxynucleotide, antibody (e.g., anti-CTLA4, anti-GD2, anti-PD1, anti-PDL1, anti-CD47, anti-CD20, anti-CD52), checkpoint inhibitor, or biological agent (e.g. antigen-specific T-cells or antigen presenting cells not necessarily conjugated to Prussian Blue nanoparticles); wherein said agent is optionally covalently or non-covalently bound or associated with said nanoparticle; wherein said chemokine may be selected from those described at https://en.wikipedia.org/wiki/Chemokine (last accessed Feb. 12, 2016) and wherein said cytokine may be selected from those described at https://en.wikipedia.org/wiki/Cytokine (last accessed Feb. 12, 2016)

38. The combined method of any one of embodiments 1-37, wherein the at least one other immunotherapy comprises treating a subject with an immunotherapy selected from the group of immunotherapies described by Galuzzi, et al., *Classification of current anticancer immunotherapies*, Oncotarget 5(24): 12472-12508 (2014) which are hereby incorporated by reference in their entireties.

39. The combined method of any one of embodiments 1-38 that reduces tumor burden, tumor metastasis, or tumor growth rate by 5, 10, 15, 20, 25, 30, 35, 40, 45, 50, 55, 60, 65, 70, 75, 80, 85, 90, 95, 100, 150, 200, 300, 400, 500% or more compared to a subject treated a nanoparticle-based therapy alone or with immunotherapy alone, or by more than the sum of separate treatments with the nanoparticle or immunotherapy or that increases mean survival at 1, 2, 3, 4, 5, 6, 7, 8, 9, 10, 11, 12, 18, 24, 36, 48, or 60 months compared to the survival rate of subject(s) treated with nanoparticle-based therapy alone or with immunotherapy alone, or more than the sum of separate treatments with nanoparticles or immunotherapies.

40. The combined method of any one of embodiments 1-39 that reduces tumor recurrence by 5, 10, 15, 20, 25, 30, 35, 40, 45, 50, 55, 60, 65, 70, 75, 80, 85, 90, 95, 100, 150, 200, 300, 400, 500% or more compared to a subject treated a nanoparticle-based therapy alone or with immunotherapy alone, or more than the sum of separate treatments with a nanoparticle-based therapy alone or with immunotherapy alone 41. The combined method of any one of embodiments 1-40, wherein said subject has a cancer, malignancy, neoplasm, or tumor, or a hyperplasia, wart, or other condition associated with abnormal cell proliferation or is infected by a virus, bacterium, fungus, yeast, or parasite.

42. The combined method of any one of embodiments 1-41, wherein said subject has a pediatric, non-pediatric, or an adult cancer, malignancy, neoplasm, or tumor or an associated condition selected from the group consisting of Adrenocortical Carcinoma, AIDS-Related Cancer, Anal Cancer, Anemia associated with malignancy or cancer treatment, Angiosarcoma, Astrocytoma, Basal Cell Carcinoma, Biliary Cancer, Bladder Cancer, Bone Cancer, Brain Metastasis, Brain Tumor, Breast Cancer, Carcinoid, Cervical Cancer, Chondrosarcoma, Coagulation Disorders associated with malignancy or cancer treatment, Colon Cancer, Craniopharyngioma, Desmoid Tumor, Ductal Carcinoma in Situ (DCIS), Endometrial Cancer, Esophageal Cancer, Fibrosarcoma, Gastric (Stomach) Cancer, Gastrointestinal Carcinoid Tumor, Gastrointestinal Stromal Tumor (GIST), Gestational Trophoblastic Tumor, Glioblastoma, Glioma, Histiocytosis, Kidney Cancer, Langerhans Cell Histiocytosis, Laryngeal Cancer, Leiomyosarcoma, Leptomeningeal Cancer, Acute Lymphoblastic Leukemia (ALL), Acute Myeloid Leukemia (AML), Chronic Lymphocytic leukemia (CLL), Chronic Myelogenous Leukemia (CML), Liver Cancer, non-small cell lung cancer, small cell lung cancer, Burkitt Lymphoma, Hodgkin Lymphoma, Non-Hodgkin Lymphoma, Primary CNS Lymphoma, Melanoma, Meningioma, Merkel Cell Carcinoma, Mesothelioma, Molar Pregnancy, Monoclonal Gamopathy of Undetermined Significance (M-GUS), Multiple Myeloma, Myelodysplastic Syndromes, Myeloproliferative Disorder, Nasopharyngeal Cancer, Neuroblastoma, Neurofibrosarcoma, Oligodendroglioma, Oropharyngeal Cancer, Osteosarcoma, Ovarian Cancer, Pancreatic Cancer, Parathyroid Cancer, Penile Cancer, Pineal Gland Parenchymal Tumor, Pituitary Adenoma, Prostate Cancer, Rectal Cancer, Renal Cell Cancer, Salivary Gland Cancer, Epithelioid Sarcoma, Ewing Sarcoma, Kaposi's Sarcoma, Soft Tissue Sarcoma, Synovial Sarcoma, Uterine Sarcoma, Skin Cancer, Testicular Cancer, Vaginal Cancer, Vulvar Cancer, or Waldenström's Macroglobulinemia; or metastasis thereof.

43. The combined method of any one of embodiments 1-42, wherein said subject has a pediatric cancer selected from the group consisting of leukemia, brain or other central nervous system tumors, neuroblastoma, Wilms tumor, lymphoma including Hodgkin and non-Hodgkin lymphoma, rhabdomyosarcoma, retinoblastoma, and bone cancer; or metastasis thereof.

44. The combined method of any one of embodiments 1-43, wherein said subject has neuroblastoma, melanoma or metastatic melanoma, or non-small cell lung cancer.

45. The combined method of any one of embodiments 1-44, wherein said subject has benign or neoplastic prostatic hyperplasia, Cushing's disease, congenital adrenal hyperplasia, endometrial hyperplasia, hemihyperplasia, hyperplasia of the breast, intimal hyperplasia, focal epithelial hyperplasia, sebaceous hyperplasia, or compensatory liver hyperplasia.

46. The combined method of any one of embodiments 1-45, wherein the subject has a viral, bacterial, yeast, fungal, or parasitic infection.

47. A composition comprising Prussian blue nanoparticles and at least one immunotherapeutic agent suitable for performing the immunotherapy according to any one of embodiments 1, wherein said immunotherapeutic agent is an immunomodulator, drug, or substance that modulates the immune system; including but not limited antibodies (e.g., anti-tumor antigen antibodies), epitope-binding portions of an antibody, antibody conjugates including cytotoxic conjugates, radiological agents, other tumor-targeted agents, cytokines, chemokines, interferons, interleukins, colony stimulating factors, drugs or other agents that modulate immune responses, immune cells or engineered cells that interact with, recognize, or bind to target cells; and wherein said immunotherapeutic agent may be covalently- or non-covalently associated with the Prussian blue nanoparticles.

48. A composition suitable for performing the method of any one of embodiments 1-46 comprising a cell or platelet in combination with Prussian blue nanoparticles, wherein said cells are optionally selected from the group consisting of a T-cell, NK-cell, B-cell, macrophage, monocyte, microglia, Mast cell, granulocyte, and dendritic cell and selectively interact, recognize, or bind to a target cell such as a cancer, malignant, neoplastic or tumor cell.

49. A kit comprising Prussian blue nanoparticles and at least one immunotherapeutic agent for performing the immunotherapy according to any one of embodiments 1-46, optionally, the kit may include printed, computer-readable, or link-addressed instructions for administering the nanoparticle and immunotherapeutic components such a dosage, route of administration, regimen, and site of administration; it may contain the nanoparticle and immunotherapeutic components in a combined form or as separate components in different container; such components may be present in dry or concentrated form and accompanied by suitable reconstitution media, buffers or physiological diluents.

50. A cell comprising and covalently- or non-covalently-associated with Prussian blue nanoparticles that exhibits, or has been engineered or treated to exhibit, at least one immunotherapeutic action on a target cell, such as on a cancer, malignant, neoplastic or tumor cell.

51. The cell to embodiment 50 that is a living cell, an inactivated, non-proliferating cell (e.g., one treated by radiation or a chemical agent) or a dead or fragmented cell.

52. The cell of any one of embodiments 50-51 that is a malignant cell or other target cell.

53 The cell of any one of embodiments 50-52 that is a non-malignant cell, such as an immune cell or a cell that specifically recognizes at least one cancer, neoplastic, or tumor epitope.

54. The cell of any one of embodiments 50-53 that is a stem cell, cord blood cell, or other immunologically naïve cell.

55. The cell of any one of embodiments 50-54 that is at least one kind of human mononuclear peripheral blood mononuclear (PBMC) cell.

56 The cell of any one of embodiments 50-55 that is at least one human mononuclear peripheral blood mononuclear (PBMC) cell that has been stimulated by exposure to autologous, allogeneic, xenogeneic or synthetic antigen-presenting cells that have been pulsed or exposed to peptide antigen(s), such as to an overlapping peptide library representing one or more antigens of a cancer, neoplasm or tumor or one or more antigens of a pathogen, or one or more autoantigens.

57. The cell of any one of embodiments 50-56 that is a T-cell (including cytotoxic, helper, delta-gamma, and NK cell types), a pre-T-cell or a T-cell precursor cell.

58. The cell of any one of embodiments 50-57 that is a macrophage or monocyte.

59. The cell of any one of embodiments 50-58 that is a B-cell.

60. The cell of any one of embodiments 50-59 that is a neutrophil, eosinophil basophil or other leukocyte.

61. The cell of any one of embodiments 50-60 that is a T-cell or other immunocyte that specifically recognizes at least one antigen or epitope from a cancer, malignancy, neoplasm, or tumor cell, or at least one antigen or epitope associated with hyperplasia, wart, or other condition associated with abnormal cell proliferation or with infection or opportunistic infection by a virus, bacterium, or parasite.

62. The cell of any one of embodiments 50-61 that is a T-cell or other immunocyte that specifically recognizes at least one antigen or epitope from a pediatric, non-pediatric, or an adult cancer, malignancy, neoplasm, or tumor or an associated condition selected from the group consisting of Adrenocortical Carcinoma, AIDS-Related Cancer, Anal Cancer, Anemia associated with malignancy or cancer treatment, Angiosarcoma, Astrocytoma, Basal Cell Carcinoma, Biliary Cancer, Bladder Cancer, Bone Cancer, Brain Metastasis, Brain Tumor, Breast Cancer, Carcinoid, Cervical Cancer, Chondrosarcoma, Coagulation Disorders associated with malignancy or cancer treatment, Colon Cancer, Craniopharyngioma, Desmoid Tumor, Ductal Carcinoma in Situ (DCIS), Endometrial Cancer, Esophageal Cancer, Fibrosarcoma, Gastric (Stomach) Cancer, Gastrointestinal Carcinoid Tumor, Gastrointestinal Stromal Tumor (GIST), Gestational Trophoblastic Tumor, Glioblastoma, Glioma, Histiocytosis, Kidney Cancer, Langerhans Cell Histiocytosis, Laryngeal Cancer, Leiomyosarcoma, Leptomeningeal Cancer, Acute Lymphoblastic Leukemia (ALL), Acute Myeloid Leukemia (AML), Chronic Lymphocytic leukemia (CLL), Chronic Myelogenous Leukemia (CML), Liver Cancer, non-small cell lung cancer, small cell lung cancer, Burkitt Lymphoma, Hodgkin Lymphoma, Non-Hodgkin Lymphoma, Primary CNS Lymphoma, Melanoma, Meningioma, Merkel Cell Carcinoma, Mesothelioma, Molar Pregnancy, Monoclonal Gamopathy of Undetermined Significance (M-GUS), Multiple Myeloma, Myelodysplastic Syndromes, Myeloproliferative Disorder, Nasopharyngeal Cancer, Neuroblastoma, Neurofibrosarcoma, Oligodendroglioma, Oropharyngeal Cancer, Osteosarcoma, Ovarian Cancer, Pancreatic Cancer, Parathyroid Cancer, Penile Cancer, Pineal Gland Parenchymal Tumor, Pituitary Adenoma, Prostate Cancer, Rectal Cancer, Renal Cell Cancer, Salivary Gland Cancer, Epithelioid Sarcoma, Ewing Sarcoma, Kaposi's Sarcoma, Soft Tissue Sarcoma, Synovial Sarcoma, Uterine Sarcoma, Skin Cancer, Testicular Cancer, Vaginal Cancer, Vulvar Cancer, or Waldenström's Macroglobulinemia; or metastasis thereof.

63. The cell of any one of embodiments 50-62 that is a T-cell or other immunocyte that specifically recognizes at least one antigen or epitope from a pediatric cancer selected from the group consisting of leukemia, brain or other central nervous system tumors, neuroblastoma, Wilms tumor, lymphoma including Hodgkin and non-Hodgkin lymphoma, rhabdomyosarcoma, retinoblastoma, and bone cancer; or metastasis thereof.

64. The cell of any one of embodiments 50-63 that is a T-cell or other immunocyte that recognizes at least one antigen or epitope from neuroblastoma, melanoma or metastatic melanoma, or non-small cell lung cancer.

65. The cell of any one of embodiments 50-64 that is a T-cell or other immunocyte that recognizes at least one antigen or epitope from benign or neoplastic prostatic hyperplasia, Cushing's disease, congenital adrenal hyperplasia, endometrial hyperplasia, hemihyperplasia, hyperplasia of the breast, intimal hyperplasia, focal epithelial hyperplasia, sebaceous hyperplasia, or compensatory liver hyperplasia.

66. The cell of any one of embodiments 50-65 that further comprises a natural or exogenous receptor, epitope, or other moiety which binds the nanoparticle to it.

67. The cell of any one of embodiments 50-66 that further comprises a moiety which binds the nanoparticle to it, wherein said moiety is biotin or (strep)avidin; and wherein the nanoparticle respectively comprises (strep)avidin or biotin.

68. The cell of any one of embodiments 50-67 that comprises at least one bifunctional or multifunctional nanoparticle comprising a moiety that binds to said cell and a moiety that binds to a target cell.

69. The cell of any one of embodiments 50-68 that further comprises at least one detectable marker or immunotherapeutic agent.

70. A conjugate comprising Prussian blue nanoparticles that are covalently- or non-covalently associated with at least one or more non-cellular agent(s);

wherein said non-cellular agent(s) optionally may comprise a molecule such as a chemokine, cytokine, enzyme, protein, carbohydrate, nucleic acid, lipid, polyethylene glycol, single chain polymes, fullerene; a higher order molecular structure such as a quaternary protein structure, virus, viroid, virus-like particle, or capsid; cross-linked polymer, aggregate, nanoparticle (including nanoparticles comprising gold, silver, nickel, iron, copper, zinc, or oxides and ceramics thereof; silica nanoparticles; magnetic nanoparticles, radioactive nanoparticles, cytotoxic nanoparticles, polymeric micelle nanoparticles, polymer coated iron oxide nanoparticles, protein filled nanoparticles, cerium oxide nanoparticles, and nanodiamonds optionally bound to protein molecules or chemotherapeutic drugs), microparticles, liposomes, micelles, or other non-cellular structure; and wherein said conjugate exhibits at least one immunotherapeutic action on a target cell, such as inhibiting the growth, metastasis, metabolism, apoptosis, or proliferation of a cancer, malignant, neoplastic or tumor cell.

71. The conjugate of embodiment 70, wherein the at least one non-cellular agent binds to at least one or more determinant(s) on a target cell.

72. The conjugate of embodiment 70 or 71, wherein the at least one non-cellular agent interacts with at least one or more receptor(s) on a target cell or on immune cells around the target cell.

73. The conjugate of embodiment 70, 71 or 72, wherein the at least one non-cellular agent is bifunctional or multifunctional and capable of binding to both the Prussian blue nanoparticle and to the target cell, or capable of binding to determinants on both a target cell and on immune cells adjacent to the target cell.

74. The conjugate of any one of embodiments 70-73, wherein the non-cellular agent comprises a chemokine, such as any of those described at https://en.wikipedia.org/wiki/Chemokine (last accessed Feb. 12, 2016).

75. The conjugate of any one of embodiments 70-74, wherein the non-cellular agent comprises a cytokine, such as any of those described at https://en.wikipedia.org/wiki/Cytokine (last accessed Feb. 12, 2016).

76. The conjugate of any one of embodiments 70-75, wherein the non-cellular agent comprises oligodeoxynucleotide, such as an aptamer that binds to a target cell or to a component thereof, a nucleic acid vector or construct, sense or antisense DNA or RNA including si-RNA.

77. The conjugate of any one of embodiments 70-76, wherein the non-cellular agent comprises an antibody (e.g., anti-CTLA4, anti-GD2, anti-PD1, anti-PDL1, anti-CD47, anti-CD20, anti-CD52), bispecific antibody, single chain antibody, antigen-binding portion of an antibody, or CDR of an antibody; especially an antibody or antibody component that specifically binds to a target cell or a target-cell specific antigen or epitope or an antibody or antibody component that specifically interacts receptors on the target cell or on cells in the vicinity of the target cell.

78. The conjugate of any one of embodiments 70-77, wherein the non-cellular agent is a checkpoint inhibitor.

79. The conjugate of any one of embodiments 70-78, wherein the non-cellular agent is an antibody, antigen binding portion of an antibody, aptamer, or other ligand that binds to at least one cancer, malignancy, neoplasm, or tumor cell, antigen or epitope.

80. The conjugate of any one of embodiments 70-79, wherein the non-cellular agent is an antibody, antigen binding portion of an antibody, aptamer, or other ligand that binds to at least one antigen or epitope from a or at least one antigen or epitope associated with hyperplasia, wart, or other condition associated with abnormal cell proliferation or with infection or opportunistic infection by a virus, bacterium, or parasite.

81. The conjugate of any one of embodiments 70-80, wherein the non-cellular agent is an antibody, antigen binding portion of an antibody, aptamer, or other ligand that specifically recognizes at least one antigen or epitope from a pediatric, non-pediatric, or an adult cancer, malignancy, neoplasm, or tumor or an associated condition selected from the group consisting of Adrenocortical Carcinoma, AIDS-Related Cancer, Anal Cancer, Anemia associated with malignancy or cancer treatment, Angiosarcoma, Astrocytoma, Basal Cell Carcinoma, Biliary Cancer, Bladder Cancer, Bone Cancer, Brain Metastasis, Brain Tumor, Breast Cancer, Carcinoid, Cervical Cancer, Chondrosarcoma, Coagulation Disorders associated with malignancy or cancer treatment, Colon Cancer, Craniopharyngioma, Desmoid Tumor, Ductal Carcinoma in Situ (DCIS), Endometrial Cancer, Esophageal Cancer, Fibrosarcoma, Gastric (Stomach) Cancer, Gastrointestinal Carcinoid Tumor, Gastrointestinal Stromal Tumor (GIST), Gestational Trophoblastic Tumor, Glioblastoma, Glioma, Histiocytosis, Kidney Cancer, Langerhans Cell Histiocytosis, Laryngeal Cancer, Leiomyosarcoma, Leptomeningeal Cancer, Acute Lymphoblastic Leukemia (ALL), Acute Myeloid Leukemia (AML), Chronic Lymphocytic leukemia (CLL), Chronic Myelogenous Leukemia (CML), Liver Cancer, non-small cell lung cancer, small cell lung cancer, Burkitt Lymphoma, Hodgkin Lymphoma, Non-Hodgkin Lymphoma, Primary CNS Lymphoma, Melanoma, Meningioma, Merkel Cell Carcinoma, Mesothelioma, Molar Pregnancy, Monoclonal Gamopathy of Undetermined Significance (M-GUS), Multiple Myeloma, Myelodysplastic Syndromes, Myeloproliferative Disorder, Nasopharyngeal Cancer, Neuroblastoma, Neurofibrosarcoma, Oligodendroglioma, Oropharyngeal Cancer, Osteosarcoma, Ovarian Cancer, Pancreatic Cancer, Parathyroid Cancer, Penile Cancer, Pineal Gland Parenchymal Tumor, Pituitary Adenoma, Prostate Cancer, Rectal Cancer, Renal Cell Cancer, Salivary Gland Cancer, Epithelioid Sarcoma, Ewing Sarcoma, Kaposi's Sarcoma, Soft Tissue Sarcoma, Synovial Sarcoma, Uterine Sarcoma, Skin Cancer, Testicular Cancer, Vaginal Cancer, Vulvar Cancer, or Waldenström's Macroglobulinemia; or metastasis thereof.

82. The conjugate of any one of embodiments 70-81, wherein the non-cellular agent is an antibody, antigen binding portion of an antibody, aptamer, or other ligand that specifically recognizes at least one antigen or epitope from a pediatric cancer selected from the group consisting of leukemia, brain or other central nervous system tumors, neuroblastoma, Wilms tumor, lymphoma including Hodgkin and non-Hodgkin lymphoma, rhabdomyosarcoma, retinoblastoma, and bone cancer; or metastasis thereof.

83. The conjugate of any one of embodiments 70-82, wherein the non-cellular agent is an antibody, antigen binding portion of an antibody, aptamer, or other ligand that recognizes at least one antigen or epitope from neuroblastoma, melanoma or metastatic melanoma, or non-small cell lung cancer.

84. The conjugate of any one of embodiments 70-83, wherein the non-cellular agent is an antibody, antigen binding portion of an antibody, aptamer, or other ligand that recognizes at least one antigen or epitope from benign or neoplastic prostatic hyperplasia, Cushing's disease, congenital adrenal hyperplasia, endometrial hyperplasia, hemihyperplasia, hyperplasia of the breast, intimal hyperplasia, focal epithelial hyperplasia, sebaceous hyperplasia, or compensatory liver hyperplasia.

85. The conjugate of any one of embodiments 70-84, that further comprises a natural or exogenous receptor, epitope, or other moiety which binds the nanoparticle to it.

86. The conjugate of any one of embodiments 70-85, wherein the Prussian blue nanoparticle and non-cellular agent are covalently-attached.

87. The conjugate of any one of embodiments 70-86, wherein the Prussian blue nanoparticle and non-cellular agent are non-covalently attached, for example, via respective binding of biotin or (strep)avidin on the nanoparticle to (strep)avidin or biotin on the non-cellular agent.

88. The conjugate of any one of embodiments 70-87, wherein the non-cellular agent is bifunctional and recognizes or interacts with that comprises at least one bifunctional or multifunctional Prussian blue nanoparticle comprising a moiety that binds to said non-cellular agent and a moiety that binds to or interacts with a target cell.

89. The conjugate of any one of embodiments 70-88, that further comprises at least one detectable marker or immunotherapeutic agent, including but not limited to an anticancer drug, toxin or radioactive agent.

90. A Prussian blue nanoparticle that is coated, compounded or combined with at least one substance that reduces or prevents degradation of the Prussian blue component (e.g., degradation caused by contact with hydroxyl ions or other reactive components) in blood, plasma or lymph compared to an otherwise identical nanoparticle that is not coated, compounded or combined.

91. The nanoparticle of embodiment 90 that when introduced in vivo into blood, plasma, CSF, tissue fluid, lymph or other bodily fluids substantially prevents degradation of the Prussian blue component for 1, 2, 3, 4, 5, 6, 7, 8, 9, 10, 15, 30, 60, 120, 180 minutes or other time sufficient for the nanoparticle to come into contact with a cancer, neoplastic or tumor cell or other target cell; and optionally for a time sufficient for it to attach to or be endocytosed by said target cell, and optionally for a time sufficient for it to absorb radiation applied during a photothermal treatment.

92. The nanoparticle of embodiment 90 or 91 that comprises at least one, two or three protective layer(s) that reduce(s) or prevents contact between the Prussian blue component of the nanoparticle and hydroxyl ions in blood, plasma or lymph.

93. The nanoparticle of embodiment 90, 91 or 92 that comprises a nanoshell, liposome, micelle, or liposome-like synthetic particle.

94. The nanoparticle of any one of embodiments 90-93 that comprises a coating.

95. The nanoparticle of any one of embodiments 90-94 that comprises a coating selected from the group consisting of a polymer that comprises, consists essentially of, or consists of ADOGEN® 464, ALKANOL® 6112, BRIJ® 52, BRIJ® 93, BRIJ® S2, BRIJ® S, BRIJ® L4, BRIJ® O10, BRIJ® S10, BRIJ® S20, Ethylenediamine tetrakis(ethoxylate-block-propoxylate) tetrol, IGEPAL® CA-210, IGEPAL® CA-520, IGEPAL® CA-720, IGEPAL® CO-630, IGEPAL® CO-890, IGEPAL® DM-990, MERPOL® DA, MERPOL® HCS, MERPOL® OJ, MERPOL® SE, MERPOL® SH, MERPOL® A, poly(ethylene glycol) sorbitan tetraoleate, poly(ethylene glycol) sorbitol hexaoleate, poly(ethylene glycol), polyethylene-block-poly (ethylene glycol), sorbitan monopalmitate, 2,4,7,9-tetramethyl-5-decyne-4,7-diol ethoxylate, 2,4,7,9-tetramethyl-5-decyne-4,7-diol, TRITON™ N-101, TRITON™ X-100, TRITON™ X-100 reduced, TRITON™ X-114, TRITON™ X-405, reduced, TWEEN® 20, TWEEN® 40, TWEEN® 60, TWEEN® 85, ZONYL® FS-300, ZONYL® FSA, ZONYL® FSN, ZONYL® FSO fluorosurfactant, acrylic acid (AA), 4,4'-azobis(4-cyanopentanoic acid); ACPA), 2,2'-azobisisobutyronitrile (AIBN), sodium bis(2-ethylhexyl) sulfosuccinate (AOT), sodium dihexyl sulfosuccinate (AMA-80), Amphi-Dex, acrylonitrile (AN), bis(2-pyridyl-methyl)-octadecylamine (BPMODA), BRIJ® 30 (polyoxyethylene-4-lauryl ether), 1-butyl-3-methylimidazolium hexafluorophosphate ([C4mim]PF6), poly(oxyethylene) octyl phenyl ether (CA897),CMC-A9, carboxymethylated poly(ethylene glycol) (CMPEG), cetyltrimethylammonium bromide (CTAB), cetyltrimethylammonium chloride (CTMA-Cl), didodecyldimethylammonium bromide (DDAB), dodecanoic acid 2-(2-hydroxyethoxy)ethyl ester (DDA-HEEE), decyltrimethylammonioumbromide (DeTAB), dodecyl mercaptane (DDM), dextran ester (Dex-Est), SG1-based bifunctional alkoxyamine (DIAMA-Na), dimethyl acetamide (DMAc), dodecyl methacrylate (DMA), (dimethylamino)ethyl methacrylate (DMAEMA), 3-(N,N-dimethylmyristylammonio) (DMMA-PS), dodecyl mercaptane, dodecyltrimethylammonioumbromide (DTAB), methacrylic acid copolymer (EUDRAGIT® L100-55), poly (ethylene-co-butylene)-b-poly(ethylene oxide) (KLE3729), lauryl methacrylate (LMA), monomethoxy-poly(ethylene glycol) (mPEG), monomethoxy-poly(ethylene oxide)-poly (lactic acid) (mPEO-PLA), methyl methacrylate (MMA), octyl trimethyl ammonium bromide (OTAB), polyaniline-poly(styrenesulfonic acid) (PANI-PSS), poly(γ-benzyl-1-glutamate)-b-poly(ethylene oxide) (PBG-PEO), poly(ε- caprolactum) (PCL), poly(oxyethylene)-poly(oxypropylene) copolymer (PE/F68), poly(ethylene oxide) (PEO), poly(ethyleneglycol) (PEG), poly(hydroxyl butyrate) (PHB), poly(heptadecafluorodecylacrylate) (PHDFDA), poly(hydroxyethyl methacrylate) (PHEMA), poly(lactide-fumarate) (PLAF), poly(d,l-lactic acid-co-glycolic acid) (PLGA), poly(lactide-co-glycolide fumarate) (PLGF), poly(l-lactic acid) (PLLA), Pluronic F-108, poly($\alpha,\beta$-1-malic acid) (PMA), poly(methyl methacrylate) (PMMA), poly(N-isopropylacrylamide-co-methacrylic acid) (P(NIPAM-MAA)), poly(ethylene oxide)-poly(propylene oxide) ethylene diamine co-polymer(Poloxamine 908), poly(styrenesulfonic acid) (PSS), poly(trimethylene carbonate) (PTMC), poly(vinyl alcohol) (PVA), sodium 4-(v-acryloyloxyalkyl) oxy benzene sulfonate (SABS), sodium dodecyl sulfate (SDS), sodium lauryl sulfate (SLS), sodiumoctylbenzene sulfonate (SOBS), stearyl methacrylate (SMA), 5-sulfoisophthalic acid dimethyl ester sodium salt modified tetracarboxylic acid-terminated polyester (SMTAPE), sorbitan monopalmitate (SPAN® 40), sorbitan monooleate (SPAN® 80), sorbitane trioleate (SPAN® 85), and sodium persulfate (SPS).

96. The nanoparticle of any one of embodiments 90-95 that comprises at least one buffer, preferably in a controlled-released form or as a coating, that neutralizes hydroxyl ions or other reactive species thus inhibiting degradation of the Prussian blue component of the nanoparticle.

97. The nanoparticle of any one of embodiments 90-96 that comprises at least one protective layer that reduces or prevents contact between the nanoparticle and hydroxyl ions in blood, plasma or lymph, wherein, optionally, said protective layer is stable at pH 7.0 to 8.0, and preferably stable at a pH 7.3 to 7.5.

98. The nanoparticle of any one of embodiments 90-97 that comprises at least one natural or synthetic polymer coating that prevents substantial degradation of the Prussian blue component while in blood, plasma or lymph or mildly alkaline physiological solutions.

99. A method for treating a subject in need of photothermal therapy or combined photothermal and immune therapy comprising administering the nanoparticle according to any one of embodiments 90-98.

EXAMPLES

Physiologically Stable Prussian Blue Nanoparticles

Prussian blue is an ancient dye composed of mixed-valence iron hexacyanoferrate nanoparticles with a face-centered cubic lattice structure consisting of $Fe^{II}$—CN—$Fe^{II}$ bonds. Prussian blue nanoparticles (PB NPs) possess imaging and therapeutic capabilities, but hydroxyl ions attack $Fe^{II}$—CN—$Fe^{III}$ bonds of the PB NP lattice causing degradation. Over the past decade, Prussian blue nanoparticles (PB NPs) have been increasingly investigated for use in imaging and therapy applications in biomedical research because of the ease of synthesizing them and tailoring their properties. The use of PB NPs in imaging and therapy applications implicitly indicates their inherent physiological stability. However, studies conducted in mildly alkaline solutions, a characteristic property of many physiological fluids such as human blood and lymph; suggest the instability of PB NPs in the presence of excess hydroxyl ions, which attack the $Fe^{II}$—CN—$Fe^{III}$ bonds of the PB NP lattice causing their rapid degradation. The inventors sought to explain these seemingly contradictory observations by elucidating the mechanisms underlying PB NP stability in physiological solutions.

First, the degradation of PB NPs in phosphate buffered saline, a mildly alkaline physiological buffer used to mimic the osmolarity/ion concentration of human blood/lymph is described. Next, improved stability and slower degradation of PB NPs when coated with albumin, a major component of blood serum, indicating a protective effect by the formation of a protein corona on the nanoparticles is demonstrated. Accordingly, a layer-by-layer strategy to coat PB NPs with biocompatible polymers to confer tunable degradation kinetics in physiological solutions is implemented. These in vitro studies permit the design of stable PB NPs with tailorable degradation properties for use in imaging and therapy applications in vivo. The inventors recognized that proteins in physiological solutions can partially shield PB NPs from degradation and implement a layer-by-layer polymer coating approach to control PB NP degradation.

Prussian blue nanoparticles (PB NPs) are mixed-valence, iron-based cyanometallate nanoparticles that have recently been investigated for use in diverse biomedical applications. PB NPs have a face-centered cubic lattice structure consisting of $Fe^{II}$—CN—$Fe^{III}$ bonds. See M. Shokouhimehr, E. S. Soehnlen, A. Khitrin, S. Basu and S. D. Huang, Inorg. Chem. Comm., 97 (2010) 58, incorporated herein by reference in its entirety. PB NPs are US Food and Drug Administration (FDA)-approved for the treatment of radioactive exposure (marketed as Radiogardase), and have been used to effectively treat radioactive cesium and thallium poisoning clinically. See J. M. Verzijl, H. C. Joore, A. van Dijk, F. C. Wierckx, T. J. Savelkoul and J. H. Glerum, J. Toxicol. Clin. Toxicol., 31 (1993) 553; P. J. Faustino, Y. Yang, J. J. Progar, C. R. Brownell, N. Sadrieh, J. C. May, E. Leutzinger, D. A. Place, E. P. Duffy, F. Houn, S. A. Loewke, V. J. Mecozzi, C. D. Ellison, M. A. Khan, A. S. Hussain and R. C. Lyon, J. Pharm. Biomed. Anal., 47 (2008) 114; Y. Yang, P. J. Faustino, J. J. Progar, C. R. Brownell, N. Sadrieh, J. C. May, E. Leutzinger, D. A. Place, E. P. Duffy, L. X. Yu, M. A. Khan and R. C. Lyon, Int. J. Pharm. 358 (2008) 187; and H. H. Kamerbeek, A. G. Rauws, M. ten Ham and A. N. van Heijst, Acta Med. Scand., 189 (1971) 321, each incorporated herein by reference in their entirety. Additionally, PB NPs have been synthesized to possess imaging capabilities, as demonstrated in published studies describing their use as imaging agents including: magnetic resonance imaging (MRI) agents, photoacoustic imaging agents, and multi-modal imaging agents, e.g. combined MRI/fluorescence imaging and combined computed tomography (CT)/photoacoustic imaging. See M. F. Dumont, S. Yadavilli, R. W. Sze, J. Nazarian and R. Fernandes, Int. J. Nanomed., 9 (2014) 2581; M. Shokouhimehr, E. S. Soehnlen, J. Hao, M. Griswold, C. Flask, X. Fan, J. P. Basilion, S. Basu and S. D. Huang, J. Mater. Chem., 20 (2010) 5251; W. Zhu, K. Liu, X. Sun, X. Wang, Y. Li, L. Cheng and Z. Liu, ACS Appl. Mater. Interfaces, 7 (2015) 11575; X. Liang, Z. Deng, L. Jing, X. Li, Z. Dai, C. Li and M. Huang, Chem. Commun., 49 (2013) 11029; M. F. Dumont, H. A. Hoffman, P. R. Yoon, L. S. Conklin, S. R. Saha, J. Paglione, R. W. Sze, and R. Fernandes, Bioconjug. Chem., 25 (2014) 129; J. M. Vojtech, J. Cano-Mejia, M. F. Dumont, R. W. Sze and R. Fernandes, J. Vis. Exp., 98 (2015) e52621; and L. Jing, X. Liang, Z. Deng, S. Feng, X. Li, M. Huang, C. Li and Z. Dai, Biomaterials, 35 (2014) 5814, each incorporated herein by reference in their entirety. PB NPs have also been used in therapeutic applications. Specifically, PB NPs have been used for photothermal therapy (PTT), which exploits PB NPs' property of exhibiting a defined absorption peak at near infrared (NIR) wavelengths (650-900 nm). See G. Fu, W. Liu, Y. Li, Y. Jin, L. Jiang, X. Liang, S. Feng, Z. Dai, Bioconjug. Chem., 25 (2014) 1655; and H. A. Hoffman, L. Chakrabarti, M. F. Dumont, A. D. Sandler and R. Fernandes R, RSC Adv., 4 (2014) 29729, each incorporated herein by reference in their entirety. Consequently, PB NPs heat up when exposed to a low power, NIR laser. PB NP-based PTT can be used to ablate (thermally destroy) tumors after intratumoral and intravenous injection of the nanoparticles. See L. Cheng, H. Gong, W. Zhu, J. Liu, X. Wang, G. Liu and Z. Liu, Biomaterials, 35 (2014) 9844, incorporated herein by reference in its entirety. Other groups have correspondingly used PB NPs for magnetic-guided chemotherapy, combined PTT/chemotherapy, photothermally enhanced gene or drug delivery, and for theranostic use wherein the PB NPs function as both therapy and diagnostic agents. See M. B. Zakaria, A. A. Belik, C. H. Liu, H. Y. Hsieh, Y. T. Liao, V. Malgras, Y. Yamauchi and K. C. Wu, Chem. Asian J., 10 (2015) 1457; P. Xue, K. K. Cheong, Y. Wu and Y. Kang, Colloids Surf. B., 125 (2015) 277; M. Wu, Q. Wang, X. Liu and J. Liu, RSC Adv., 5 (2015) 30970; X. D. Li, X. L. Liang, F. Ma, L. J. Jing, L. Lin, Y. B. Yang, S. S. Feng, G. L. Fu, X. L. Yue and Z. F. Dai, Colloids Surf B., 123 (2014) 629; and P. Xue, J. Bao, Y. Wu, Y. Zhang and Y. Kang, RSC Adv., 5 (2015) 28401, each incorporated herein by reference in their entirety.

Implicit in the utilization of the PB NPs for imaging and therapy applications is their physiological (in vivo) stability. However, studies in the field of electrochemistry, where Prussian blue films are extensively used in sensor applications, suggest their instability in the presence of excess hydroxyl ions. See F. Ricci and G. Palleschi, Biosens. Bioelectron., 21 (2005) 389; and F. Ricci, A. Amine, G. Palleschi and D. Moscone D, Biosens. Bioelectron., 18 (2003) 165, each incorporated herein by reference in their entirety. These excess hydroxyl ions attack the $Fe^{II}$—CN—$Fe^{III}$ bonds that make up the lattice structure of PB NPs, causing their rapid degradation. See K. Itaya, H. Akahoshi and S. Toshima, J. Electrochem. Soc., 129 (1982) 1498; and A. Karyakin, Electroanalysis, 13 (2001) 813, each incorporated herein by reference in their entirety. Incidentally, many physiological solutions have a mildly alkaline pH (e.g. blood pH~7.4, lymph>7.4). Therefore, one would expect PB NPs to be attacked and rapidly degraded in these mildly alkaline physiological solutions. The goal of this communication is to elucidate these seemingly contradictory observations of stability (or transient stability) of the PB NPs in mildly alkaline physiological solutions, i.e. conditions typically encountered in imaging and therapy applications in vivo. The inventors hypothesized that the stability of PB NPs observed in physiological solution arises from the formation of a protective protein coating on the nanoparticles, and that by a priori coating of the PB NPs with biocompatible polymers, the inventors can control their physiological stability and degradation.

To test this hypothesis, the inventors first determined the stability and degradation properties of the PB NPs. These studies were conducted in phosphate buffered saline (PBS), which is a mildly alkaline buffer (pH 7.4) used to mimic the osmolarity and ion concentration of physiological solutions such as human blood and lymph. Specifically, the inventors quantify the stability of the PB NPs using dynamic light scattering (DLS), visible-near infrared (Vis-NIR) spectroscopy, and PTT. DLS provides information on the sizes (hydrodynamic diameters) of the nanoparticles and can be used to provide information on colloidal stability and aggregation, as stable PB NPs would be expected to show monodisperse size distributions ranging between 20-300 nm. Vis-NIR spectroscopy provides information on the $Fe^{II}$—CN—$Fe^{III}$ bonds of the PB NP lattice. These bonds generate a peak absorbance in the range of 650-900 nm wavelengths, corresponding to the energy of the metal-to-metal charge transfer between $Fe^{II}$ and $Fe^{III}$ through the cyanide bridge of the PB NP lattice. If attacked by hydroxyl ions, one would expect to see a decrease in the characteristic absorbance peak of the PB NPs in the Vis-NIR spectrum. Additionally, the inventors sought to measure the ability of the PB NPs for use in PTT. Degraded PB NPs (after attack by hydroxyl ions) would not be expected to heat to temperatures as high as stable functional PB NPs. Hence, the inventors use this PTT capability of the PB NPs as a measure of their functionality.

Next, the inventors test the stability and degradation properties of albumin-coated PB NPs. The rationale for conducting these studies was that PB NP protection in physiological solutions may occur due to the formation of a PB NP-protective protein corona. See T. Cedervall, I. Lynch, S. Lindman, T. Berggård, E. Thulin, H. Nilsson, K. A. Dawson, and S. Linse, Proc. Nat. Acad. Sci. USA., 104 (2007) 2050; and A. S. Pitek, D. O'Connell, E. Mahon, M. P. Monopoli, F. Baldelli Bombelli and K. A. Dawson, PLoS One, 7 (2012) e40685, each incorporated herein by reference in their entirety. As proof-of-concept, the inventors used albumin as a representative protein since it is the most abundant serum protein and a major component of protein coronas generated on nanoparticles in blood. See S. Tenzer, D. Docter, S. Rosfa, A. Wlodarski, J. Kuharev, A. Rekik, S. K. Knauer, C. Bantz, T. Nawroth, C. Bier, J. Sirirattanapan, W. Mann, L. Treuel, R. Zellner, M. Maskos, H. Schild and R. H. Stauber, ACS Nano, 5 (2011) 7155, incorporated herein by reference in its entirety. The inventors determined the stability and degradation properties of the resultant albumin-coated PB NPs using DLS, Vis-NIR, and PTT. However, relying on protein coatings in physiological solutions (e.g. serum proteins) which have diverse compositions, may lead to variable and unpredictable PB NP degradation kinetics. Therefore, the inventors sought to synthesize physiologically stable PB NPs by using a previously described layer-by-layer (LbL) approach to attach biocompatible polymers onto the surface of PB NPs after synthesis to confer tunable degradation kinetics to the resultant nanoparticles. Polymer coating techniques have been well-described in the literature; they assist in increasing the biocompatibility and stability of nanoparticles, as well as aiding in their biofunctionalization. See W. G. Kreyling, A. M. Abdelmonem, Z. Ali, F. Alves, M. Geiser, N. Haberl, R. Hartmann, S. Him, D. J. de Aberasturi, K. Kantner, G. Khadem-Saba, J. M. Montenegro, J. Rejman, T. Rojo, I. R. de Larramendi, R. Ufartes, A. Wenk and W. J. Parak, Nat Nanotechnol., 10 (2015) 619; A. Quarta, A. Curcio, H. Kakwere and T. Pellegrino, Nanoscale, 4 (2012) 3319; and F. Zhang, E. Lees, F. Amin, P. Rivera Gil, F. Yang, P. Mulvaney and W. J. Parak, Small, 7 (2011) 3113, each incorporated herein by reference in their entirety. Our PB NPs are initially coated with two polymers of opposing charges, polyallylamine hydrochloride and poly(acrylic acid), and subsequently with polyethylene glycol (PEG). PEGylation is used widely in nanoparticle synthesis as it increases the blood circulation times of nanoparticles, increases water solubility of hydrophobic nanoparticle components, and shields the nanoparticles from being attacked by the immune system by decreasing their immunogenicity and antigenicity. See J. V. Jokerst, T. Lobovkina, R. N. Zare and S. S. Gambhir, Nanomedicine (Lond)., 6 (2011) 715, incorporated herein by reference in its entirety. Using DLS, Vis-NIR, and PTT, the inventors proceeded to test whether LbL-coated PB NPs exhibited slower degradation kinetics than uncoated PB NPs, and if they remained stable in physiological solutions. This approached provided a foundation for utilizing this design approach to control the stability and degradation of PB NPs in physiological solutions.

Materials.

All synthetic procedures were conducted using ultrapure water obtained from a Milli-Q system (Millipore Corporation, Billerica, MA) with resistivity of 18.2 MΩ·cm. Potassium hexacyanoferrate (II) trihydrate (MW 422.39; K4[Fe (CN)6]·3H2O), iron (III) chloride hexahydrate (MW 270.3; Fe(Cl)3·6H2O), albumin from bovine serum, polyallylamine hydrochloride (PAH; MW 15,000), poly(acrylic acid) solution (PAA; MW 2,000), and N-(3-dimethylaminopropyl)-NO-ethylcarbodiimide hydrochloride; EDC) were all purchased from Sigma-Aldrich (St. Louis, MO). Phosphate buffered saline (PBS) pH 7.4 was purchased from Life Technologies (Grand Island, NY). The 808 nm near infrared (NIR) laser was purchased from Laserglow Technologies (Toronto, ON, Canada). Neuro2a cells were purchased from ATCC (Manassas, VA). Finally, amino (m)-PEG-NH2 (MW 5,000) was purchased from Nanocs (New York, NY).

Synthesis of PB NPs.

The PB NP were synthesized at room temperature (RT) as previously described. See G. Fu, W. Liu, S. Feng and X. Yue, Chem. Commun., 48 (2012) 11567. N. W. Roehm, G. H. Rodgers, S. M. Hatfield and A. L. Glasebrook, J. Immunol. Methods, 142 (1991) 257, incorporated herein by reference in its entirety. Briefly, an aqueous solution of 6.8 mg FeCl3.6·6H2O ($2.5 \times 10^{-5}$ mol) in 5 mL of Milli-Q water was added under vigorous stirring to an aqueous solution containing 10.6 mg of $K_3Fe(CN)_6 \cdot 3H_2O$ ($2.5 \times 10^{-5}$ mol) in 5 mL of Milli-Q water. After stirring for 15 min, the resultant precipitate was collected by centrifugation (20,000×g for 5 min) and rinsed with Milli-Q water using sonication to suspend the nanoparticles (microtip sonicator probe Model Q125, QSonica, Newtown, CT). The collection and rinsing steps were repeated at least three times before the particles were finally resuspended in Milli-Q water. PB-NPs and methods for making and using them are also incorporated by reference to U.S. 20140271487 A1, entitled PRUSSIAN BLUE-INSPIRED CONSTRUCTS FOR MULTIMODAL IMAGING AND THERAPY which is hereby incorporated by reference in its entirety.

Nanoparticle Coating Methods.

To coat the PB NPs with albumin, 0.3 mg albumin from bovine serum was added to 1 mg PB NPs in 1 mL Milli-Q water, vortexed, and allowed to mix on an orbital shaker at RT for at least two hours. The optimal relative proportion of PB NPs and albumin was determined by conducting prior studies on the albumin-binding capacity of the PB NPs using methods previously described by us. After contacting PB NPs with albumin, the unbound albumin was rinsed off by collecting the albumin-coated PB NPs by centrifugation for 5 minutes at 20,000×g and discarding the supernatant. The albumin-coated PB NPs were resuspended by brief sonication in 0.5 mL of Milli-Q water and the collection and rinsing steps were repeated at least three times. After the last centrifugation, the particles were resuspended in Milli-Q water.

PB NPs were coated using an LbL approach as described by Cheng et al., with minor modifications. Briefly, 10 mL of 1 mg/mL PB NPs were added dropwise into 4 mg/mL aqueous solution of PAH under sonication for 30 minutes at RT. This solution was then stirred vigorously for at least four hours, centrifuged at 16,000×g for 10 minutes to collect the PAH-coated PB NPs (PB-PAH) and resuspended in Milli-Q water as described above. The PB-PAH nanoparticles were then added dropwise into 4 mg/mL PAA under sonication for 30 minutes at RT, stirred vigorously for at least four hours, and rinsed as stated above resulting in PAA-coated nanoparticles (PB-PAH-PAA). Next, 10 mg/mL m-PEG-NH2 was added dropwise to the solution of PB-PAH-PAA nanoparticles under sonication for 30 minutes at RT. 10 mg EDC was then added and the solution was allowed to incubate overnight while stirring. The final LbL-coated nanoparticles (PB-PAH-PAA-PEG) were rinsed and resuspended as described above. The surface charges (zeta potentials) of the nanoparticles after each step of the LbL-coating are described in the supporting information (FIG. 5).

Dynamic Light Scattering (DLS) and Zeta Potential.

The sizes and zeta potentials of all nanoparticles were measured using a Zetasizer Nano ZS (Malvern Instruments, Worcestershire, U.K.). PB NP suspensions were made in either Milli-Q water or PBS and the size and charge analyses were performed using the manufacturer's specifications.

Vis-NIR Spetroscopy.

The Vis-NIR absorbance spectra of the various nanoparticles were measured on the Genesys 10S spectrophotometer (Thermo Scientific, Waltham, MA) using the VISIONlite software. PB NPs suspensions were made in Milli-Q water or PBS and the analyses were performed as per the manufacturer's instructions.

PTT and Viability Studies.

All PTT studies were performed using an 808 nm NIR laser at a power of 1.25 W/cm$^2$. 100 uL total volume of nanoparticles and/or cells were plated in a 96-well plate and irradiated for ten minutes. Temporal temperature measurements were taken using a thermocouple (Omega, Stamford, CT). Cell viability post-PTT was measured using the XTT assay (Trevigen, Gaithersburg, MD) whereby absorbance of metabolized product is measured as a measure for viability. Mitochondria of metabolically active cells are able to cleave tetrazolium salt into formazan, which can be measured by absorbance at 490 nm.

PB NPs were Stable and Functional as PTT Agents.

Figure 1:
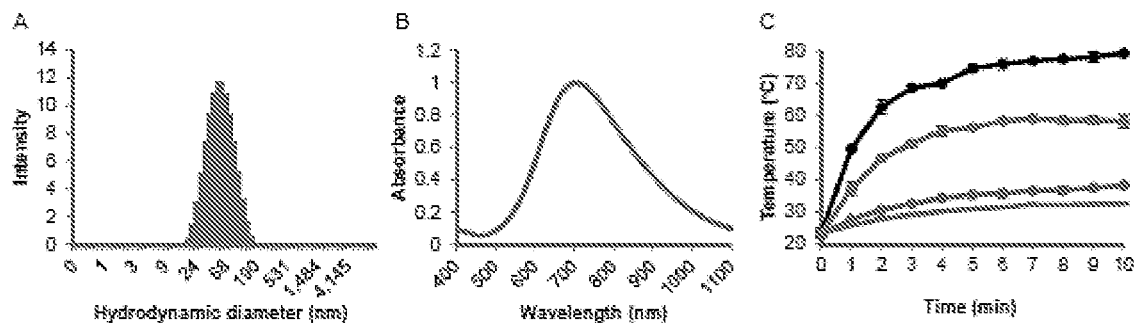
FIG. 1. Stability, Vis-NIR, and PTT properties of PB NPs in water.

The inventors measured the stability and functionality of the synthesized PB NPs (i.e. PB NP suspensions in water) using DLS, Vis-NIR, and PTT, as a baseline for subsequent comparative studies. As measured by DLS, the synthesized PB NPs exhibited an average hydrodynamic diameter of 58.77 nm (FIG. 1A). The Vis-NIR spectrum of PB NPs showed its characteristic absorption band from 650-900 nm, corresponding to the energy of the metal-to-metal charge transfer between $Fe^{II}$ and $Fe^{III}$ through the cyanide bridge of the PB NB lattice (Amax=705 nm) (FIG. 1B). The inventors performed PTT on varying concentrations of PB NPs (0.01-1.0 mg/mL) in a 96-well plate using an 808 nm laser at a power density of 1.25 W/cm$^2$ for 10 minutes. PTT resulted in the PB NPs heating in a concentration-dependent manner, with 1.0 mg/mL PB NPs exhibiting the highest heating (79.4° C.) after 10 minutes (FIG. 1C). Additionally, the inventors assessed the ability of the PB NPs to ablate cancer cells in vitro. 0.1 mg/mL PB NPs was able to photothermally ablate neuroblastoma (neuro2a) cells in vitro, generating a significant 70.6% decrease in cellular viability as measured by the XTT assay (p<0.0001, FIG. 6). Neither the NIR laser (p=0.65) nor the PB NPs (p=0.13) alone generated any cytotoxicity on neuro2a cells when compared to untreated control neuro2a cells. These data illustrate the intrinsic stability of the PB NP suspensions in water. They exhibit monodisperse size distributions and exhibit peak absorbance at NIR wavelengths, corresponding to the bonds comprising PB NPs' lattice structure. Further, they are effective agents for PTT; they are able to heat dramatically and ablate cancer cells.

PB NPs Degrade and Lose their Stability and Functionality in Phosphate Buffered Saline (PBS).

Figure 2:
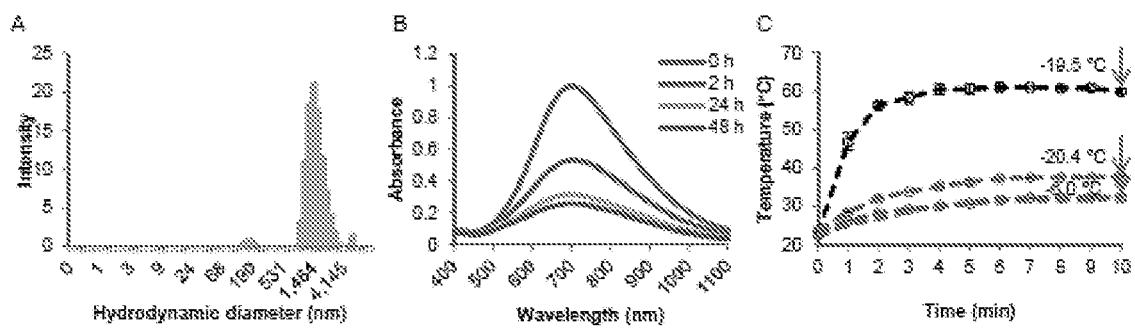
FIG. 2. The effect of PBS on the stability, Vis-NIR, and PTT properties of PB NPs.

Although PB NPs were stable and effective for use when suspended in water, they rapidly degraded when they encounter mildly alkaline physiological solutions such as PBS. PBS is made up of inorganic salts (no proteins or cellular components) at pH 7.4, mimicking the pH of blood and lymph. The inventors again utilized DLS, Vis-NIR, and PTT temporal temperature measurements to measure the stability and functionality of the PB NPs in PBS. When the PB NPs are suspended in PBS, DLS showed a marked increase in the hydrodynamic sizes of the nanoparticles (FIG. 2A), suggesting aggregation and instability of the nanoparticles in PBS. To confirm that this aggregation was not a result of colloidal instability but rather of nanoparticle degradation, the inventors assessed the stability of the constituent $Fe^{II}$—CN—$Fe^{III}$ bonds using Vis-NIR spectroscopy. As expected, a marked decrease in the PB NP characteristic NIR peak with increasing time of contact with PBS (decreasing to 25.6% of the original peak intensity after 48 hours) was observed, which can be attributed to the attack of the $Fe^{II}$—CN—$Fe^{III}$ bonds by the slight excess of hydroxyl ions in PBS (FIG. 2B). In addition, the PB NPs contacted with PBS for 24 hours are unable to generate as high temperatures reached by the PB NPs in water after 10 minutes of PTT (concentration dependent, FIG. 2C). Thus, the PB NPs quickly lose their functionality as PTT agents in a mildly alkaline physiological solution such as PBS. The effect is even more dramatic as the pH of the solution is further increased to 10 and 12; PTT for 10 minutes (1.25 W/cm$^2$) can no longer heat PB NPs over 35° C. (FIG. 7), identical to the temperature rise of water or PBS irradiated without any PB NPs. These data suggest that the hydroxyl ions present in physiological media attack the $Fe^{II}$—CN—$Fe^{III}$ bonds of the PB NPs causing their degradation, and that this effect is accelerated and more pronounced as the pH of the solution is increased. Therefore, it is imperative to consider this degradation behavior of PB NPs in alkaline solutions. Many physiological solutions encountered in vivo, such as human blood and lymph, are mildly alkaline, and would predictably degrade the PB NPs in a similar manner to that observed in PBS, resulting in inconsistent and unpredictable nanoparticle properties. Noteworthy here is that studies in literature using PB NPs do not describe this degradation phenomenon of PB NPs. The inventors therefore posit, without being bound to any particular explanation, that the stability of PB NPs observed in those studies serendipitously arose from the formation of a protective coating on the nanoparticles. This hypothesized protective coating could be generated by protein coronas formed on the uncoated PB NPs, or by the coatings used to biofunctionalize the PB NPs (including the commonly used citrate-capped PB NPs).

Albumin Coating Improves Stability and Functionality of PB NPs in PBS.

To test the hypothesis that proteins coating the PB NPs (protein corona) contribute to stabilizing PB NPs in physiological buffers, PB NPs were coated with a layer of albumin from bovine serum. The properties of the resultant albumin-coated nanoparticles were analyzed using DLS, Vis-NIR, and PTT as previously described. The albumin-coated PB NPs exhibited polydispersity with multiple size distributions: a high intensity peak at 91.28 nm and lower intensity peaks at larger size distributions (FIG. 3A), illustrating the inherent difficulty of relying on the use of serum proteins to reliably stabilize the PB NPs. It is important to mention here that it is possible to generate monodisperse albumin-coated PB NPs but this requires significant post-processing including filtering of proteins, sonication, and concentration optimizations, which does not occur in vivo. In addition, the characteristic PB NP peak on the Vis-NIR spectrum decreased to 57.1% over 48 hours (FIG. 3B), which is a modest improvement over the uncoated PB NPs' degradation kinetics (FIG. 2B). Similarly, albumin-coated PB NPs in PBS could not reach similar temperatures as those attained in water (51.7 vs. 60.3 C, respectively) after 10 minutes of PTT, but were still able to heat up (FIG. 3C). These data shed light on previously published studies that demonstrated PB NP stability and functionality in vivo. Despite the probable presence of hydroxyl ions in these environments, perhaps proteins such as albumin were incidentally protecting the PB NPs in vivo. These data illustrate a proof-of-concept explanation of how a protein corona protects PB NPs in physiological environments. Studies that have shown in vivo stability may have serendipitously relied on this method. As described earlier, this method of using proteins present in physiological solutions (e.g. albumin, the most abundant blood serum protein) to incidentally protect PB NPs in vivo, however, is unpredictable and incomplete. Therefore, the inventors implemented an LbL approach to coat the PB NPs with biopolymers to create a reliable and rationally designed stable nanoparticle.

LbL-Coated PB NPs are Stable and Functional in PBS.

The same characterization techniques were used to analyze the stability and functionality of the LbL-coated PB NPs in PBS. DLS shows LbL-coated PB NPs in PBS have a monodisperse size distribution with an average hydrodynamic diameter of 220.2 nm (FIG. 4A). Further, the peak on the Vis-NIR spectrum corresponding to PB NPs' $Fe^{II}$—CN—$Fe^{III}$ bonds illustrates only 25% loss of absorbance after 48 hours in PBS (FIG. 4B), exhibiting improved stability over uncoated and albumin-coated PB NPs. Importantly, LbL-coated PB NPs in PBS showed no decrease in temperature after PTT (reaching 76.0 C at 1 mg/mL) compared with both LbL-coated PB NPs in water, and uncoated PB NPs in water, demonstrating improved stability and functionality of the PB NPs after LbL coating (FIG. 4C). Admittedly, further studies need to be performed to improve the stability and functionality of the nanoparticles, such as optimizing the synthesis conditions to control the nanoparticle sizes, and varying the coatings with the polymers described here (or using different biocompatible polymers) to tailor the nanoparticle degradation kinetics for each application in vivo. Nonetheless, these studies serve as an initial proof-of-concept of the design considerations for synthesizing PB NPs that are stable under diverse physiological conditions.

As shown by the results of the studies described above, the physiological environments (e.g. blood, lymph) are often mildly alkaline and would likely cause the degradation of uncoated PB NPs. Proteins found in physiological solutions such as human blood serum (e.g. albumin) are sometimes adequate to shield PB NPs' $Fe^{II}$—CN—$Fe^{III}$ bonds and prevent their degradation in such environments; however, this method of protection can result in unpredictable and unreliable PB NP properties. To ensure a robust design of PB NPs for clinical applications (imaging, therapeutic, theranostic), the degradation kinetics must be well-described and consistent. Utilizing a rationally designed LbL-coating method wherein PB NPs are coated with biocompatible polymers, PB NPs can be protected against hydroxyl ion attack in physiological solutions, allowing them to remain reliably stable and functional for longer periods of time. These results illustrate the utility of using a rationally designed, LbL approach to confer stability and functionality to PB NPs with tunable degradation kinetics. These studies are an important step in designing PB NP-based nanoparticles with superior performance attributes for clinical use.

Prussian Blue Nanoparticles and Checkpoint Inhibition for Photothermal Immunotherapy of Cancer Nanoparticles have been used extensively in the treatment of cancer because of their diverse therapeutic and imaging capabilities. Recently, nanoparticles have also been explored in combination with immunotherapies for cancer therapy because these combinations have the potential to provide more durable responses and confer immunity. Here, the inventors describe Prussian blue nanoparticle (PBNP)-based photothermal therapy in combination with anti-CTLA-4 checkpoint inhibition for "photothermal immunotherapy" of neuroblastoma, a common and hard-to-treat pediatric cancer. Photothermal therapy serves as a rapid and minimally invasive method to destroy tumors using a near infrared laser and near infrared light-absorbing nanoparticles. Anti-CTLA-4 is an immune checkpoint inhibitor that reverses immunosuppression and elicits an antitumor response. The inventors' nanoparticle synthesis scheme yields PBNPs that exhibit pH-dependent stability; that is, they are stable at a mildly acidic pH representing tumor interstitia and rapidly degrade under mildly alkaline conditions mimicking blood and lymph. Photothermal therapy using intratumorally administered PBNPs in a mouse neuroblastoma model elicits a rapid reduction of tumor burden and growth rate, but the response is incomplete and the tumors recur. However, PBNP-combined with anti-CTLA-4-based photothermal immunotherapy results in 55% survival at 100 days in neuroblastoma-bearing mice. This is compared to 12.5%, 0%, and 0% survival at 100 days in animals treated with: (i) anti-CTLA-4 alone, (ii) photothermal therapy alone, and (iii) no treatment, respectively. Finally, the photothermal immunotherapy-treated mice that survived long-term exhibited protection against neuroblastoma tumor rechallenge, suggesting the development of immunity against these tumors illustrating the potential of photothermal immunotherapy as a novel combination therapy for the treatment of cancer.

Advances in the field of nanomedicine have yielded nanoparticles with multifunctional therapy and imaging ("theranostic") capabilities for treating cancer, where several nanoparticles have either received FDA approval or are currently undergoing clinical evaluation. See Schutz, C. A.; Juillerat-Jeanneret, L.; Mueller, H.; Lynch, I.; Riediker, M., Therapeutic nanoparticles in clinics and under clinical evaluation. *Nanomedicine (Lond)* 2013, 8 (3), 449-67; and Rink, J. S.; Plebanek, M. P.; Tripathy, S.; Thaxton, C. S., Update on current and potential nanoparticle cancer therapies. *Curr Opin Oncol* 2013, 25 (6), 646-51, each incorporated herein by reference in their entirety. An emerging area of interest in cancer nanomedicine is the use of nanoparticles in combination with immunotherapies, which specifically target and/or activate the immune system. See Bear, A. S.; Kennedy, L. C.; Young, J. K.; Perna, S. K.; Mattos Almeida, J. P.; Lin, A. Y.; Eckels, P. C.; Drezek, R. A.; Foster, A. E., Elimination of metastatic melanoma using gold nanoshell-enabled photothermal therapy and adoptive T cell transfer. *PLoS One* 2013, 8 (7), e69073; Guo, L.; Yan, D. D.; Yang, D.; Li, Y.; Wang, X.; Zalewski, O.; Yan, B.; Lu, W., Combinatorial photothermal and immuno cancer therapy using chitosan-coated hollow copper sulfide nanoparticles. *ACS Nano* 2014, 8 (6), 5670-81; Wang, C.; Xu, L.; Liang, C.; Xiang, J.; Peng, R.; Liu, Z., Immunological responses triggered by photothermal therapy with carbon nanotubes in combination with anti-CTLA-4 therapy to inhibit cancer metastasis. *Adv Mater* 2014, 26 (48), 8154-62; and Zhang, P.; Chiu, Y. C.; Tostanoski, L. H.; Jewell, C. M., Polyelectrolyte Multilayers Assembled Entirely from Immune Signals on Gold Nanoparticle Templates Promote Antigen-Specific T Cell Response. *ACS Nano* 2015, 9 (6), 6465-77, each incorporated herein by reference in their entirety. These combination "nano-immunotherapies" offer the potential for improved and durable responses over conventional cancer therapies (e.g. chemotherapy, surgery, radiation therapy) and the potential for conferring immunity to treated subjects, providing long-term protection against cancer recurrence. In this study, the inventors describe a combination therapy termed "photothermal immunotherapy", which combines Prussian blue nanoparticle (PBNP)-based photothermal therapy (PTT) with anti-CTLA-4 checkpoint inhibition for treating cancer.

Nanoparticle-based PTT functions as a rapid and minimally invasive method for reducing tumor burden using near infrared (NIR) light-absorbing nanoparticles and a low power NIR laser. See Huang, X.; Jain, P. K.; El-Sayed, I. H.; El-Sayed, M. A., Plasmonic photothermal therapy (PPTT) using gold nanoparticles. *Lasers Med Sci* 2008, 23 (3), 217-28; and Loo, C.; Lowery, A.; Halas, N.; West, J.; Drezek, R., Immunotargeted nanoshells for integrated cancer imaging and therapy. *Nano Lett* 2005, 5 (4), 709-11, each incorporated herein by reference in their entirety. Several reports have demonstrated the efficacy of PTT using diverse nanoparticles including gold nanoshells, gold nanorods, gold nanocages, and carbon nanotubes in animal cancer models such as breast cancer, squamous cell carcinoma, and prostate cancer. See Hirsch, L. R.; Stafford, R. J.; Bankson, J. A.; Sershen, S. R.; Rivera, B.; Price, R. E.; Hazle, J. D.; Halas, N. J.; West, J. L., Nanoshell-mediated near-infrared thermal therapy of tumors under magnetic resonance guidance. *Proc Nat Acad Sci USA* 2003, 100 (23), 13549-54; Lal, S.; Clare, S. E.; Halas, N. J., Nanoshell-enabled photothermal cancer therapy: impending clinical impact. *Acc Chem Res* 2008, 41 (12), 1842-51; Dickerson, E. B.; Dreaden, E. C.; Huang, X.; El-Sayed, I. H.; Chu, H.; Pushpanketh, S.; McDonald, J. F.; El-Sayed, M. A., Gold nanorod assisted near-infrared plasmonic photothermal therapy (PPTT) of squamous cell carcinoma in mice. *Cancer Lett* 2008, 269 (1), 57-66; Au, L.; Zheng, D.; Zhou, F.; Li, Z. Y.; Li, X.; Xia, Y., A quantitative study on the photothermal effect of immuno gold nanocages targeted to breast cancer cells. *ACS Nano* 2008, 2 (8), 1645-52; Cobley, C. M.; Au, L.; Chen, J.; Xia, Y., Targeting gold nanocages to cancer cells for photothermal destruction and drug delivery. *Expert Opin Drug Deliv* 2010, 7 (5), 577-87; Kam, N. W.; O'Connell, M.; Wisdom, J. A.; Dai, H., Carbon nanotubes as multifunctional biological transporters and near-infrared agents for selective cancer cell destruction. *Proc Nat Acad Sci USA* 2005, 102 (33), 11600-5; Yu, J. G.; Jiao, F. P.; Chen, X. Q.; Jiang, X. Y.; Peng, Z. G.; Zeng, D. M.; Huang, D. S., Irradiation-mediated carbon nanotubes' use in cancer therapy. *J Cancer Res Ther* 2012, 8 (3), 348-54; Burke, A. R.; Singh, R. N.; Carroll, D. L.; Wood, J. C.; D'Agostino, R. B., Jr.; Ajayan, P. M.; Torti, F. M.; Torti, S. V., The resistance of breast cancer stem cells to conventional hyperthermia and their sensitivity to nanoparticle-mediated photothermal therapy. *Biomaterials* 2012, 33 (10), 2961-70; Huang, N.; Wang, H.; Zhao, J.; Lui, H.; Korbelik, M.; Zeng, H., Single-wall carbon nanotubes assisted photothermal cancer therapy: animal study with a murine model of squamous cell carcinoma. *Laser Surg Med* 2010, 42 (9), 638-48; and Stern, J. M.; Stanfield, J.; Kabbani, W.; Hsieh, J. T.; Cadeddu, J. A., Selective prostate cancer thermal ablation with laser activated gold nanoshells. *J Urol* 2008, 179 (2), 748-53, each incorporated herein by reference in their entirety. Here, the inventors utilize PBNPs, whose photothermal properties have only recently been described, as PTT agents. See Fu, G.; Liu, W.; Feng, S.; Yue, X., Prussian blue nanoparticles operate as a new generation of photothermal ablation agents for cancer therapy. *Chem Commun* 2012, 48, 11567-11569; and Hoffman, H. A.; Chakarbarti, L.; Dumont, M. F.; Sandler, A. D.; Fernandes, R., Prussian blue nanoparticles for laser-induced photothermal therapy of tumors. *RSC Adv* 2014, 4 (56), 29729-29734, each incorporated herein by reference in their entirety. As compared to common alternative nanoparticles used for PTT, PBNPs offer several advantages; they are easily synthesized in a single and scalable step using a one-pot synthesis scheme, do not require costly synthesis materials, and are already FDA-approved for human oral use to treat radioactive poisoning. See Shokouhimehr, M.; Soehnlen, E. S.; Hao, J.; Griswold, M.; Flask, C.; Fan, X.; Basilion, J. P.; Basu, S.; Huang, S. D., Dual purpose Prussian blue nanoparticles for cellular imaging and drug delivery: a new generation of T1-weighted MRI contrast and small molecule delivery agents *J Mater Chem* 2010, 20, 5251-5259; Dumont, M. F.; Hoffman, H. A.; Yoon, P. R.; Conklin, L. S.; Saha, S. R.; Paglione, J.; Sze, R. W.; Fernandes, R., Biofunctionalized Gadolinium-Containing Prussian Blue Nanoparticles as Multimodal Molecular Imaging Agents. *Bioconjug Chem* 2014, 25 (1), 129-137; Dumont, M. F.; Yadavilli, S.; Sze, R. W.; Nazarian, J.; Fernandes, R., Manganese-containing Prussian blue nanoparticles for imaging of pediatric brain tumors. *Int J Nanomed* 2014, 9, 2581-95; Vojtech, J. M.; Cano-Mejia, J.; Dumont, M. F.; Sze, R. W.; Fernandes, R., Biofunctionalized prussian blue nanoparticles for multimodal molecular imaging applications. *J Vis Exp* 2015, (98), e52621; Faustino, P. J.; Yang, Y.; Progar, J. J.; Brownell, C. R.; Sadrieh, N.; May, J. C.; Leutzinger, E.; Place, D. A.; Duffy, E. P.; Houn, F., et al., Quantitative determination of cesium binding to ferric hexacyanoferrate: Prussian blue. *J Pharm Biomed Anal* 2008, 47 (1), 114-25; Yang, Y.; Faustino, P. J.; Progar, J. J.; Brownell, C. R.; Sadrieh, N.; May, J. C.; Leutzinger, E.; Place, D. A.; Duffy, E. P.; Yu, L. X., et al., Quantitative determination of thallium binding to ferric hexacyanoferrate: Prussian blue. *Int J Pharm* 2008, 353 (1-2), 187-94; and FDA: Radiogardase-ferric hexacyanoferrate(ii) capsule: http://www.accessdata.fda.gov/drugsatfda_docs/label/2008/021626s007lbl.pdf. (accessed Mar. 7, 2017), each incorporated herein by reference in their entirety.

Additionally, the inventors show that PBNPs are stable in a pH dependent manner, which allows the nanoparticles to degrade, an advantage over non-degradable nanoparticles used for PTT.

Despite the promise of nanoparticle-based PTT for cancer therapy, PTT alone can be ineffective in treating certain hard-to-treat or advanced cancers. These cancers typically require combination or multimodal approaches to achieve improved outcomes. To this end the inventors investigated PBNP-based PTT in combination with anti-CTLA-4 checkpoint inhibition immunotherapy. Checkpoint inhibition uses monoclonal antibodies to target key immune checkpoints such as CTLA-4 and PD-1 in order to reverse immune suppression, unleashing potent antitumor responses by activating endogenous immune cells (e.g. T cells). See Pardoll, D. M., The blockade of immune checkpoints in cancer immunotherapy. *Nat Rev Cancer* 2012, 12 (4), 252-64; Hodi, F. S., Cytotoxic T-lymphocyte-associated antigen-4. *Clin Cancer Res* 2007, 13 (18 Pt 1), 5238-42; and Chakrabarti, L.; Morgan, C.; Sandler, A. D., Combination of Id2 Knockdown Whole Tumor Cells and Checkpoint Blockade: A Potent Vaccine Strategy in a Mouse Neuroblastoma Model. *PLoS One* 2015, 10 (6), e0129237, each incorporated herein by reference in their entirety. Checkpoint inhibitors including anti-CTLA-4 (e.g. ipilimumab) and anti-PD-1 (e.g. nivolumab) have received FDA approval for the treatment of advanced cancers such as metastatic melanoma. See Hodi, F. S.; O'Day, S. J.; McDermott, D. F.; Weber, R. W.; Sosman, J. A.; Haanen, J. B.; Gonzalez, R.; Robert, C.; Schadendorf, D.; Hassel, J. C., et al., Improved survival with ipilimumab in patients with metastatic melanoma. *N Engl J Med* 2010, 363 (8), 711-23; and Wolchok, J. D.; Kluger, H.; Callahan, M. K.; Postow, M. A.; Rizvi, N. A.; Lesokhin, A. M.; Segal, N. H.; Ariyan, C. E.; Gordon, R. A.; Reed, K., et al., Nivolumab plus ipilimumab in advanced melanoma. *N Engl J Med* 2013, 369 (2), 122-33, each incorporated herein by reference in its entirety. Still, the responses to checkpoint inhibitors in these cancers are restricted to modest subsets of patients, which suggests a need for therapies that can elicit improved treatments outcomes in a larger group of patients. See Postow, M. A.; Chesney, J.; Pavlick, A. C.; Robert, C.; Grossmann, K.; McDermott, D.; Linette, G. P.; Meyer, N.; Giguere, J. K.; Agarwala, S. S., et al., Nivolumab and ipilimumab versus ipilimumab in untreated melanoma. *N Engl J Med* 2015, 372 (21), 2006-17, incorporated herein by reference in its entirety.

In this study, the inventors present a novel photothermal immunotherapy approach where they locally ablate tumors using PBNP-based PTT, thus disrupting the tumor mass, followed by systemic anti-CTLA-4 administration. Specifically, the inventors' combination therapy (FIG. 9) uses (1) biodegradable PBNPs for PTT where PBNPs are administered intratumorally and irradiated with an NIR laser, serving the purpose of primary tumor ablation, and (2) anti-CTLA-4 checkpoint inhibitor by intraperitoneal (i.p.) administration, which elicits a robust antitumor immune response that complements PTT. The efficacy of photothermal immunotherapy was tested in a hard-to-treat mouse model of neuroblastoma. See Chakrabarti, L.; Abou-Antoun, T.; Vukmanovic, S.; Sandler, A. D., Reversible adaptive plasticity: a mechanism for neuroblastoma cell heterogeneity and chemo-resistance. *Front Oncol* 2012, 2, 82; and Chakrabarti, L.; Wang, B. D.; Lee, N. H.; Sandler, A. D., A Mechanism Linking Id2-TGFbeta Crosstalk to Reversible Adaptive Plasticity in Neuroblastoma. *PLoS One* 2013, 8 (12), e83521, each incorporated herein by reference in their entirety. The inventors hypothesized that this novel combination of two therapies—PBNP-based PTT and anti-CTLA-4 checkpoint inhibition—would act synergistically to improve outcomes over those obtained with either modality alone. PTT using our biodegradable PBNPs resulted in slower tumor progression and decreased tumor burden in the neuroblastoma mouse model, but these tumors recurred, and none of the mice survived long-term. In contrast, PBNP-based PTT combined with anti-CTLA-4 immunotherapy resulted in complete tumor regression and long-term survival (>100 days) in a significantly higher proportion (55%) of mice relative to controls treated with anti-CTLA-4 alone (12.5%), PTT alone (0%), or left untreated (0%). In addition, long-term surviving mice treated with photothermal immunotherapy exhibited protection against neuroblastoma tumor rechallenge compared to untreated, naïve mice challenged with the neuroblastoma tumors, indicating the development of an immunity in photothermal immunotherapy-treated mice. Our findings demonstrate the efficacy of PBNP-based PTT combined with anti-CTLA-4 photothermal immunotherapy as a novel, combination therapy for the treatment of cancer.

Results

PBNPs Exhibit pH-Dependent Degradation and Stability.

To determine whether PBNPs are stable and degrade in a pH dependent manner, the inventors measured the degradation and stability of PBNPs using visible-NIR (Vis-NIR) spectroscopy and dynamic light scattering (DLS) as a function of time and at various pH levels—mimicking conditions typically encountered by intratumorally administered nanoparticles, i.e. tumor interstitia and tumor lymphatics/vasculature. Tumor interstitia exhibit a slightly acidic pH (~5.5), while blood and lymph exhibit mildly alkaline pHs (~7.4). See Meng, F.; Cheng, R.; Deng, C.; Zhong, Z., Intracellular drug release nano systems. *Mater Today* 2012, 15, 436-442; and Song, C.; Griffin, R.; Park, H. J., Influence of Tumor pH in Therapeutic Response. In *Cancer Drug Discovery and Development: Cancer Drug Resistance*, Inc., B. T. H. P., Ed. Totowa, NJ, 2006; pp 21-42, each incorporated herein by reference in their entirety. The inventors measured the Vis-NIR and DLS properties of PBNPs over seven days at three pHs—5.5 representing tumor interstitial pH, 7.0 representing neutral pH, and 7.4 representing blood/lymph pH.

The Vis-NIR spectrum of PBNPs demonstrated its characteristic absorption band from 650-900 nm, corresponding to the energy of the metal-to-metal charge transfer between $Fe^{II}$ and $Fe^{III}$ through the cyanide bridge of the PBNP lattice ($\lambda_{max}$=705 nm). This characteristic absorption band was used to quantify the degradation of the PBNPs as degraded PBNPs would be expected to exhibit an attenuated absorption band relative to intact PBNPs. PBNPs incubated at pH 5.5 (tumor interstitial pH) exhibited negligible change in their Vis-NIR spectra over seven days (FIG. 10A) indicating that the PBNPs were insignificantly degraded at pH 5.5 over the seven days. Similarly, insignificant degradation properties were observed with PBNPs incubated at neutral pH of 7.0 (FIG. 10B). However as the pH of the solution was marginally increased from 7.0 (neutral) to 7.4 (mildly alkaline, mimicking blood and lymph pH), a significant (51%) reduction in their Vis-NIR spectrum peak intensity over the course of seven days (FIG. 10C) was observed, indicating degradation of the PBNPs at pH 7.4. This was likely caused by attack of the characteristic $Fe^{II}$—CN—$Fe^{III}$ bonds of PBNP by the slight excess of hydroxyl ions potentially resulting in the formation of hydroxides and released cyanoferrate ions, as previously observed. See Itaya, K.; Akahoshi, H.; Toshima, S., Electrochemistry of Prussian Blue Modified Electrodes: An Electrochemical Preparation Method. *J Electrochem Soc* 1982, 129 (7), 1498-1500; and Karyakin, A. A., Prussian Blue and Its Analogues: Electrochemistry and Analytical Applications. *Electroanal* 2001, 13 (10), 813-819, each incorporated herein by reference in their entirety. These observations of PBNP degradation were corroborated by a study that measured PBNP concentration as a function of time and pH using optical density measurements at 680 nm and its measured mass extinction coefficient at this wavelength. Similar to the Vis-NIR observations, the PBNP concentration decreased to ~43% of its starting concentration at pH 7.4 after seven days, indicating degradation of the nanoparticles under these conditions; while remaining essentially unchanged over seven days at pH 5.5 and 7.0. As a complementary measure of nanoparticle stability, the inventors conducted a temporal DLS study, which was used to assess nanoparticle size distributions and stability. The PBNPs were observed to be stable when incubated at pH 5.5 and 7.0 (constant mean hydrodynamic diameters; FIGS. 10D and 10E).

In contrast, DLS was unable to detect a nanoparticle population of PBNPs when incubated at pH 7.4 for 7 days (FIG. 10F), indicating an attack of the nanoparticles at this blood/lymph-mimicking pH. Taken together, our findings indicate that our PBNPs are suitable for intratumoral administration as they exhibit an inherent pH-dependent degradation and stability, where they are stable under conditions mimicking the tumor interstitium (lower pH), and degrade under conditions mimicking the blood and lymph. FIGS. 10G-10I show TEM images of PBNPs on Day 7 at pH 5.5 (FIG. 10G), pH 7.0 (FIG. 10H), and pH 7.4 (FIG. 10I) showing detectable PBNPs at mildly acidic (5.5) and neutral (7.0) pHs and undetectable PBNPs at a mildly alkaline pH (7.4).

PBNPs Exhibit Improved PTT Capabilities in an Acidic Tumor pH Both In Vitro and In Vivo.

Next, studies were conducted studies to determine whether the pH-dependent stability of PBNPs had an effect on their function as PTT agents by assessing their PTT capabilities in vitro (FIG. 11A) and in vivo (FIG. 11B). The inventors measured the PTT capabilities of the PBNPs as a function of concentration (0.01-1 mg/mL) at the two pHs—5.5 and 7.4—described above. The inventors observed that the PBNPs heated to higher temperatures when they were incubated in a pH of 5.5 versus 7.4, and this occurred in a concentration-dependent manner (FIG. 11A). This is likely due to the fact that at higher pH, PBNPs exhibit a significant reduction in their PTT capabilities due to their degradation under these conditions, consistent with our earlier findings. The reduction in the PTT capabilities was also concentration-dependent; 1 mg/mL PBNPs incubated at pH 7.4 exhibited a ~16° C. decrease in temperature after PTT compared 1 mg/mL PBNPs at pH 5.5, and 0.1 mg/mL PBNPs exhibited a ~7° C. decrease in PTT capabilities between these pHs.

The PTT capabilities of the PBNPs in the syngeneic mouse model of neuroblastoma were measured. Given the degradation and stability properties of the PBNPs, the goal of this study was to determine the effective intratumoral dose of the PBNPs to achieve temperatures suitable for thermal ablation of the tumors (i.e. 50-55° C.). Using IR thermography, it was determined that mice bearing 5 mm tumors (~60 mm³ tumor volumes) intratumorally injected with 50 RL of 1 mg/mL PBNPs were able to heat up to ablative temperatures in 2-4 minutes when irradiated with an 808 nm NIR laser at 1.875 W/cm² laser power densities (FIG. 11B). These results indicate that the PBNPs exhibit pH-dependent PTT capabilities when they heat to higher temperatures at intratumoral pH compared to blood and lymph temperatures.

PTT Reduces Tumor Burden and Increases the Number of Tumor-Free Days in a Mouse Model of Neuroblastoma.

Next whether PBNP-based PTT treatment was efficacious was evaluated in a neuroblastoma tumor model. For these studies, the inventors utilized the Neuro2a syngeneic mouse model of neuroblastoma using subcutaneously injected bioluminescent Neuro2a cells, which has been shown to be an aggressive tumor model. The tumor-bearing mice were either intratumorally injected with 50 RL of 1 mg/mL PBNPs and irradiated with an 808 nm laser (1.875 W/cm² for 10 minutes) or left untreated (FIGS. 12A and 12B).

Tumor bioluminescence was measured every two days to assess tumor progression and the efficacy of the treatment (FIG. 12A-12B). Mice in the PTT-treated group exhibited near complete tumor eradication immediately after treatment (minimal measured bioluminescence; FIG. 12A) compared with mice in the untreated, control group that exhibited consistent tumor progression and growth (progressive increase in measured bioluminescence; FIG. 12B). Aggregate data from multiple tumor progression studies showed that when tumor-bearing mice were treated with PTT, their tumors rapidly shrunk, and that the mice in this group had a mean of 3 tumor-free days before the tumors recurred (FIG. 12C). Furthermore, the tumor progression was slower in these mice compared with mice in the untreated, control group, which exhibited a rapid tumor progression as evidences by a marked increase in tumor volume. Hence, these results indicate that PBNP-based PTT can rapidly reduce tumor burden and increase the number of tumor-free days with decreasing tumor growth rates in this highly aggressive neuroblastoma model.

PTT Results in an Increase in Infiltration of Lymphocytes and T Cells to the Tumor Area.

Next, the inventors sought to evaluate whether PBNP-based PTT elicited immunostimulatory effects in this neuroblastoma mouse model. To this end, studies were conducted quantifying the relative proportions of tumor infiltrating lymphocytes after PTT. For these studies, neuroblastoma-tumor bearing mice were divided into two groups: PTT-treated and untreated controls. To measure the tumor expression levels of lymphocytes and specifically T cells after PTT, mice were euthanized 24 and 96 hours post-treatment and any remain tumor tissue was isolated. Tumors were processed to obtain single cell suspensions and analyzed using flow cytometry for CD45 (lymphocyte) and CD3 (T cell) expression. After 24 h, there was no significant difference (p>0.05) in lymphocyte and T cell populations in the treated versus untreated tumors. However, 96 h post-treatment, the tumors in PTT-treated mice exhibited a significant (p>0.05) increase in lymphocyte (i.e. average values of CD45+; 9.7% PTT-treated vs. 4.1% untreated; FIGS. 13A-13C) and T cell (i.e. average values of CD3+; 6.2% PTT-treated vs. 2.2% untreated; FIGS. 13D-13F) infiltration. These results suggest that there is an increased recruitment of T cells to the tumor site after PTT given the appropriate time scale. The inventors also determined if PTT resulted in a global activation of T cells by evaluating whether splenic T cells in PTT-treated mice exhibited a recall response when co-cultured with tumor cells. IFNγ ELISpot assay showed no significant differences in recall response between the PTT and control groups, indicating that PTT alone cannot elicit a robust recall immune response important for successful tumor eradication. Taken together, these results suggest that PTT alone can stimulate an infiltration of lymphocytes and T cells to the tumor area, but that these effects are not strong to eradicate hard-to-treat cancers as shown in FIG. 12.

Photothermal Immunotherapy Results in Tumor Regression and Long-Term Survival of Mice.

In order to increase the antitumor immune response for improved therapeutic outcomes in our neuroblastoma model, the inventors used anti-CTLA-4 immunotherapy in combination with PBNP-based PTT to decrease immunosuppression and stimulate potent antitumor immune responses of endogenous immune cells. Neuroblastoma tumor-bearing mice were divided into four groups (Table 1): 1) PTT+anti-CTLA-4 group (n=9): intratumoral PTT and i.p. anti-CTLA-4, 2) PTT group (n=6): intratumoral PTT, 3) anti-CTLA-4 group (n=8): i.p. anti-CTLA-4, and 4) Untreated group (n=10): no treatment. Both the tumor progression through bioluminescent imaging, and the long-term survival of the mice were monitored.

TABLE 1

Groups and treatments used in the study.

| Group (#mice) | Treatment |
| --- | --- |
| PTT* + anti-CLTA-4# (n = 9) | PTT on Day 0; anti-CTLA-4 on Days 1, 4, 7 |
| PTT* (n = 6) | PTT on Day 0 |
| anti-CLTA-4# (n = 8) | Anti-CTLA-4 on Days 0, 3, 6 |
| Untreated | No treatment |

*PTT-treated groups receive 50 µL of 1 mg/ml PBNPs intratumorally, irradiated by an 808 nm laser at 1.875 W/cm² for 10 minutes
anti-CTLA-4-treated groups receive 150 µg of anti-CTLA-4 per dose by i.p. injection A representative temporal image measuring the tumor-specific bioluminescence indicated a gradual decrease in tumor size and the subsequent elimination of the tumor in a mouse treated with photothermal immunotherapy (FIG. 14A). Further, the tumor progression was significantly (p=0.0002) slower in the PBNP-based PTT+anti-CTLA-4 group when compared with untreated controls (FIG. 14B). Most importantly, the photothermal immunotherapy resulted in complete tumor regression and long term survival in 55.5% of the treated mice (FIG. 14C). The long-term, tumor-free survival was significantly higher (determined by a log-rank test) than that observed for mice treated with anti-CTLA-4 alone (12.5%), PTT (0%), or left untreated (0%) (p<0.0001). Depletion of CD4+ and CD8+ cells abrogated the therapeutic response (FIG. 14D). These results suggest that the PTT elicited the initial reduction in tumor burden, which was complemented by anti-CTLA-4 treatment that targeted and eliminated residual tumor cells, conferring long-term tumor-free survival in photothermal immunotherapy-treated mice. Hence, our results suggest the potential of photothermal immunotherapy in securing complete tumor remission and long-term survival in a significantly higher proportion of tumor-bearing mice.

Long-Term Surviving Mice Treated with Photothermal Immunotherapy Exhibit Protection Against Tumor Rechallenge Relative to Naive, Untreated Mice An ideal tumor therapy would be one that not only effectively eradicates tumors but prevents recurrence after successful elimination from the body. Therefore, the inventors next investigated whether photothermal immunotherapy conferred protection in long-term surviving mice that were rechallenged with the original tumor cells (Neuro2a) (FIGS. 15A-15D). Our studies consisted of two groups: 1) naive group (n=3): where mice were challenged with $10^6$ Neuro2a cells and 2) rechallenged group (n=3): where long-term surviving mice previously treated with photothermal immunotherapy were rechallenged with $10^6$ Neuro2a cells after at least 90 days of tumor-free survival. Remarkably, all of the long-term surviving mice exhibited protection against the tumor rechallenge, since these mice rapidly eliminated the rechallenged tumors (FIGS. 15A and 15C), compared with control mice where rapid tumor progression was observed (FIGS. 15B and 15D). The rechallenged mice survived for more than 90 days post tumor rechallenge compared with naive mice that had to be euthanized due to high tumor burden 12-14 days post-challenge. These data suggest the potential of photothermal immunotherapy to confer tumor immunity and protection in long-term surviving mice against tumor rechallenge/recurrence.

The results above describe the efficacy of a novel combination therapy termed photothermal immunotherapy that combines PBNP-based PTT with anti-CTLA-4 checkpoint inhibition (FIG. 9) for treating cancer. PBNPs exhibited inherent pH-dependent degradation and stability (FIG. 10) and were stable at acidic pH mimicking conditions observed in the interstitia of tumors, and exhibited incipient degradation and instability at a higher pH mimicking blood/lymph. Harnessing the pH gradient of tumor interstitia relative to surrounding tissue is an intriguing strategy to selectively trigger and/or control tumor treatment. See Madhusudhan, A.; Reddy, G. B.; Venkatesham, M.; Veerabhadram, G.; Kumar, D. A.; Natarajan, S.; Yang, M. Y.; Hu, A.; Singh, S. S., Efficient pH dependent drug delivery to target cancer cells by gold nanoparticles capped with carboxymethyl chitosan. *Int J Mol Sci* 2014, 15 (5), 8216-34; and Saboktakin, M. R.; Tabatabaie, R. M.; Maharramov, A.; Ramazanov, M. A., Synthesis and characterization of pH-dependent glycol chitosan and dextran sulfate nanoparticles for effective brain cancer treatment. *Int J Biol Macromol* 2011, 49 (4), 747-51, each incorporated herein by reference in their entirety. Tumor interstitia are typically acidic, due to the hypoxia and lactic acid accumulation that rapidly occurs in a growing tumor. See Kato, Y.; Ozawa, S.; Miyamoto, C.; Maehata, Y.; Suzuki, A.; Maeda, T.; Baba, Y., Acidic extracellular microenvironment and cancer. *Cancer Cell Int* 2013, 13 (1), 89, incorporated herein by reference in its entirety. Our in vitro data demonstrating that PBNPs exhibit properties strongly dependent on the pH of the environment suggest their potential for use in delivering tumor-specific therapies, where the PBNPs remain intact and stable intratumorally, while rapidly degrading when they enter the bloodstream or lymphatic system, thereby minimizing potential toxicities associated with the long-term persistence of the nanoparticles in vivo—an important consideration in the field of nanomedicine for eventual clinical translation. The pH-dependent properties of PBNPs had a significant effect on their PTT capabilities; PTT capabilities were decreased at blood/lymph pHs relative to intratumoral pHs (FIG. 12A). This led us to establish the concentrations of PBNPs intratumorally administered to ensure that there were sufficient nanoparticles intratumorally to effect tumor ablation (FIG. 12B). It is likely that similar optimization studies will have to be carried out should the conditions under which PTT is administered is changed, e.g. superficial versus deeper tumors may require different nanoparticle doses, laser power densities, and/or duration of irradiation. It is important to state here that should the need arise for PBNPs to exhibit longer temporal stability and significantly slower degradation kinetics than that observed (especially in applications that require intravenous administration), the PBNPs can be appropriately surface-coated with biocompatible polymers such as polyethylene glycol, as previously described. See Cheng, L.; Gong, H.; Zhu, W.; Liu, J.; Wang, X.; Liu, G.; Liu, Z., PEGylated Prussian blue nanocubes as a theranostic agent for simultaneous cancer imaging and photothermal therapy. *Biomaterials* 2014, 35 (37), 9844-52, incorporated herein by reference in its entirety.

Although growth rates were slowed, PBNP-based PTT in the mouse model for a hard-to-treat cancer (the syngeneic Neuro2a model of neuroblastoma) demonstrated an incomplete response in tumor bearing mice relative to untreated mice (FIG. 13). As described previously, PTT confers long-term, tumor-free survival in multiple animal models of cancer premised on the observation that cancer cells are more susceptible to heat than normal tissue because of their elevated metabolic rates. See Dewhirst, M. F., Jr., Roemer R B, *Hyperthermia*. Gunderson L L, Tepper J E: New York, 2000; and Kapp, D., G M Carlson, R W, *Principles of Hyperthermia*. 5th Edition ed.; Hamilton, Ontario, 2000, each incorporated herein by reference in their entirety. However, in the case of aggressive cancers, such as our neuroblastoma model, the inventors suspect that PTT does not eliminate all cancer cells even when they are undetectable by bioluminescence. The nascent cancer cells likely grow into new tumors, similar to clinical observations of latent cancer populations in neuroblastoma. See London, W. B.; Castel, V.; Monclair, T.; Ambros, P. F.; Pearson, A. D.; Cohn, S. L.; Berthold, F.; Nakagawara, A.; Ladenstein, R. L.; Iehara, T., et al., Clinical and biologic features predictive of survival after relapse of neuroblastoma: a report from the International Neuroblastoma Risk Group project. *J Clin Oncol* 2011, 29 (24), 3286-92, incorporated herein by reference in its entirety. It is possible that residual cancer cells remain even in other tumor models that show complete remission. The inventors speculate that in those cases, without being bound to any particular explanation, that the residual tumor cells may be cleared by a robust immune response.

PBNP-based PTT resulted in increased lymphocytic infiltration into the tumor regions (FIG. 13). Lymphocytes found in tumors have been shown to be effective at delaying tumor progression, suggesting their potential influence on improved patient prognosis. See Boon, T.; Coulie, P. G.; Van den Eynde, B., Tumor antigens recognized by T cells. *Immunol Today* 1997, 18 (6), 267-8; Galon, J.; Costes, A.; Sanchez-Cabo, F.; Kirilovsky, A.; Mlecnik, B.; Lagorce-Pagès, C.; Tosolini, M.; Camus, M.; Berger, A.; Wind, P., et al., Type, density, and location of immune cells within human colorectal tumors predict clinical outcome. *Science* 2006, 313 (5795), 1960-4; Lee, S.; Margolin, K., Tumor-infiltrating lymphocytes in melanoma. *Curr Oncol Rep* 2012, 14 (5), 468-74; and Zhang, L.; Conejo-Garcia, J. R.; Katsaros, D.; Gimotty, P. A.; Massobrio, M.; Regnani, G.; Makrigiannakis, A.; Gray, H.; Schlienger, K.; Liebman, M. N., et al., Intratumoral T cells, recurrence, and survival in epithelial ovarian cancer. *N Engl J Med* 2003, 348 (3), 203-13, each incorporated herein by reference in their entirety. Therefore, the increased population of CD45+ cells (FIGS. 13A-13C) in the residual tumors of PTT-treated mice presents an opportunity to recruit these cells for tumor eradication. See Chew, A.; Salama, P.; Robbshaw, A.; Klopcic, B.; Zeps, N.; Platell, C.; Lawrance, I. C., SPARC, FOXP3, CD8 and CD45 correlation with disease recurrence and long-term disease-free survival in colorectal cancer. *PLoS One* 2011, 6 (7), e22047, incorporated herein by reference in its entirety. Within this subset of lymphocytes, T cells are also present in increased numbers (CD3+ cells; FIGS. 13D-13F) and similarly present an opportunity to recruit this subset of immune effector cells to generate a T cell mediated antitumor response. See Broere, F., Sergi GSitkovsky, Michail Vvan Eden, Willem, *T cell subsets and T cell-mediated immunity*. 3rd edition ed.; 2011, incorporated herein by reference in its entirety.

PTT in combination with anti-CTLA-4 immunotherapy resulted in complete tumor regression and long-term survival in 55.5% of the tumor-bearing mice compared to only 12.5% survival observed in mice treated with anti-CTLA-4 alone and 0% survival observed in both mice treated with PTT alone or left untreated (FIG. 14). The inventors attribute this significantly higher long-term survival benefit in the photothermal immunotherapy-treated mice to the reversal of T cell exhaustion and immunosuppression by anti-CTLA-4, which is complemented by the debulking and priming of an immune response by PTT. Previous studies using the Neuro2a mouse model have demonstrated higher long-term survival using anti-CTLA-4 alone than observed in this study (~40-50% vs. 12.5% in our study). See Williams, E. L.; Dunn, S. N.; James, S.; Johnson, P. W.; Cragg, M. S.; Glennie, M. J.; Gray, J. C., Immunomodulatory monoclonal antibodies combined with peptide vaccination provide potent immunotherapy in an aggressive murine neuroblastoma model. Clin Cancer Res 2013, 19 (13), 3545-55, incorporated herein by reference in its entirety. The difference between these observations can potentially be attributed to the fact that the earlier studies commenced the anti-CTLA-4 immunotherapy when their mice reached tumor sizes of ~1 mm or after a fixed number of days (typically 5-6 days) after tumor inoculation, while the inventors commenced the therapy only after tumors reached ~5 mm, thus potentially reflecting a significantly higher tumor burden and disease progression in our studies. Finally, long-term surviving mice treated with photothermal immunotherapy exhibited protection against tumor rechallenge indicating the development of immunity against these tumors in photothermal immunotherapy-treated mice (FIG. 15). However, further studies are necessary to elucidate the underlying immunological mechanisms that elicit these protective responses. In summary, our study points to the important role that PBNPs (and other nanoparticle platforms) may play in the upcoming years in immunoengineering, where nanoparticles are used to engineer a suitable immune response to treat advanced cancers. See Goldberg, M. S., Immunoengineering: how nanotechnology can enhance cancer immunotherapy. Cell 2015, 161 (2), 201-4, incorporated herein by reference in its entirety.

The inventors disclose biodegradable PBNPs that were used in combination with anti-CTLA-4 immunotherapy for treating mice in a hard-to-treat model of neuroblastoma. These PBNPs exhibit pH dependent degradation and stability, where they are stable at lower pH mimicking the intratumoral milieu and degrade at mildly alkaline pH mimicking blood/lymph. PTT by itself was observed to confer only a marginal survival benefit in mice with neuroblastoma and resulted in a robust infiltration of lymphocytes into the tumors, but an insufficient recall response to tumor cells. Finally, mice treated with combination PTT and checkpoint inhibition exhibited significantly higher complete tumor regression and long-term tumor immunity. These results show the usefulness of a PBNP-based PTT in combination with checkpoint inhibitors in treating hard-to-treat cancers and serve as proof-of-concept preludes toward clinical translation.

The methods used to perform the studies above are described below. All synthetic procedures were conducted using ultrapure water obtained from a Milli-Q system (Millipore Corporation, Billerica, MA) with resistivity of 18.2 MV.cm. Potassium hexacyanoferrate (II) trihydrate (MW 422.39; $K_4[Fe(CN)_6] \cdot 3H_2O$) and iron (III) chloride hexahydrate (MW 270.3; $Fe(Cl)_3 \cdot 6H_2O$) were purchased from Sigma-Aldrich (St. Louis, MO).

Antibodies and Cells. Anti-CTLA-4 antibody (9D9) was purchased from BioXCell (West Lebanon, NH). Mouse CD45-FITC and CD3-FITC antibodies were purchased from eBioscience (San Diego, CA). The murine neuroblastoma cell line Neuro2a was originally obtained from American Type Culture Collections (ATCC) and cultured under recommended conditions. Cells were cultured in DMEM (Gibco, Carlsbad, CA) containing 10% fetal bovine serum (FBS, Gibco, Carlsbad, CA) and 1% penicillin/streptomycin (Sigma-Aldrich, St. Louis, MO). Luciferase-expressing Neuro2a cells were constructed by transducing the Neuro2a cells with firefly luciferase-expressing lentiviral particles (GenTarget Inc., San Diego, CA) and selecting with puromycin (Thermo Fisher, Waltham, MA). Luciferase expression was determined by measuring bioluminescence in a luminometer using the Luciferase Assay System (Promega, Madison, WI).

Animals. Four-to-six-week old female A/J mice were purchased from Jackson Laboratory (Bar Harbor, ME). The animals were acclimated for 3-4 days prior to tumor inoculation. All procedures were approved by the Institutional Animal Care and Use Committee of Children's National Health System, Washington, DC (Protocol #00030439).

PBNP synthesis. Prussian blue nanoparticles were synthesized using a scheme as described previously. Briefly, an aqueous solution of 6.8 mg $FeCl_3 \cdot 6H_2O$ ($2.5 \times 10^{-5}$ mol) in 5 mL of Milli-Q water was added under vigorous stirring to an aqueous solution containing 10.6 mg of $K_4Fe(CN)_6 \cdot 3H_2O$ ($2.5 \times 10^{-5}$ mol) in 5 mL of Milli-Q water. After stirring for 15 min, the precipitate was isolated by centrifugation (20,000×g for 5 min) and rinsed by sonication (5 s, high power) in Milli-Q water. The isolation and rinsing steps were repeated three times before the particles were resuspended by sonication in Milli-Q water.

PBNP stability and degradation studies. The sizes and zeta potentials of all particles were measured using a Zetasizer Nano ZS (Malvern Instruments, Worcestershire, U.K.). PBNP suspensions were resuspended in solutions at pH 5.5, 7.0 or 7.4. These solutions were made using appropriate amounts of mild acid and base to Milli-Q water until the desired pHs were obtained. Analyses were then performed using the manufacturer's specifications. The Vis-NIR absorbance spectra of the nanoparticles in the varied pHs were measured using the VISIONlite software on the Genesys 10S spectrophotometer (Thermo Scientific, Waltham, MA).

In vitro PTT. PTT in vitro was performed using an 808 nm NIR laser from Laserglow Technologies (Toronto, ON, Canada) at a power of 1.875 $W/cm^2$. PBNPs at concentrations of 0.01 mg/mL, 0.1 mg/mL, and 1 mg/mL were resuspended in a pH of 7.4 or 5.5, plated in a 96-well plate, and irradiated for ten minutes. Temporal temperature measurements were taken using a thermocouple (Omega, Stamford, CT).

Establishment of a mouse neuroblastoma model. For establishing primary tumors and for the rechallenge studies, $10^6$ Neuro2a cells transfected with luciferase were suspended in PBS and subcutaneously injected into the back of each previously shaved mouse. Tumor growth was monitored on alternate days following tumor inoculation by imaging the mice for tumor bioluminescence using the IVIS Lumina III (PerkinElmer). This animal imaging system allows for quantitative analysis of tumor volume over time. Tumor volumes were calculated using this imaging system as previously described. See Savoldo, B.; Rooney, C. M.; Di Stasi, A.; Abken, H.; Hombach, A.; Foster, A. E.; Zhang, L.; Heslop, H. E.; Brenner, M. K.; Dotti, G., Epstein Barr virus specific cytotoxic T lymphocytes expressing the anti-CD30zeta artificial chimeric T-cell receptor for immunotherapy of Hodgkin disease. Blood 2007, 110 (7), 2620-30, incorporated herein by reference in its entirety. A tumor size of 17 mm diameter in any dimension was designated as the endpoint and mice were euthanized at that time. Euthanasia was achieved through cervical dislocation after $CO_2$ narcosis. If the tumor impaired mobility of the animal, became ulcerated or appeared infected, or if the mice displayed signs of distress by sick mouse posture, the mice were euthanized.

In vivo PTT. For PTT in vivo, neuroblastoma-bearing mice were treated when their tumors reached a size of at least 5 mm (~60 mm$^3$ volume) measured using bioluminescence measurements. Due to the intrinsic variation in tumor engraftment, the mice were treated within a range of 3-5 days rather than on the same day. Mice were anesthetized prior to and during treatment using 2-5% isoflurane. The mice were intratumorally injected with 50 RL of PBNPs (1 mg/mL), and the tumor area was irradiated with an 808 nm NIR laser (Laserglow Technologies; Toronto, ON, Canada) at 1.875 W/cm$^2$ for 10 minutes. As an added precaution, the animals' eyes were covered with opaque black cardboard during treatment to avoid eye damage by the laser. The temperatures reached during PTT were measured using a FLIR thermal camera (Arlington, VA).

Anti-CLTA-4 injections. Anti-CTLA-4 antibody (150 Rg per mouse) was administered intra-peritoneally (i.p.) on days 1, 4, and 7 for the combination (PTT+aCTLA-4) group, and on days 0, 3, and 6 for the anti-CTLA-4 only group.

Tumor infiltration studies. Whole tumors were extracted from experimental and control tumor-bearing mice, and were minced and run through a 70Rm filter. Once single cell suspensions were obtained, the tumor cells were cultured in complete DMEM medium prior to studies. Tumor isolate was used to assess leukocyte infiltrate by flow cytometry. Cells were stained with CD45 and CD3 antibodies conjugated to FITC (BD Biosciences) and samples were run on the BD Accuri cytometer at a threshold of 80,000. Analysis of flow cytometry results was conducted in FlowJo 7.6 (TreeStar Inc.) and populations of interest and mean fluorescence intensity (MFI) were determined from ungated live samples.

IFNγ expression studies. T cells were harvested from spleens of tumor-bearing mice and isolated with CD5 immunomagnetic beads (Ly-1, Miltenyi Biotec). 200,000 murine T cells were included in an ELISpot assay (IFNγ ELISpot, Mabtech, Inc.) at 1:1 with ex vivo tumor cells, which was conducted according to the manufacturer's protocol. Splenocytes and isolated T cells were cultured in complete RPMI medium.

Statistical analysis. Statistical significance between groups was determined using a Student's t-test. Significant difference between two groups of flow cytometry data was determined using a chi-square test. To determine minimum sample sizes for each group in the animal studies, the inventors conducted a power analysis using $\alpha=0.05$ (Type I error probability associated with this test of this null hypothesis) and power=0.8. After inputting the values of $\alpha/\delta$ for each t-test (using PS power and sample size software), the inventors. These sample sizes are consistent with those in similar studies published in the literature. The log rank test was used to determine statistically significant differences in survival between the various groups, ($\alpha=0.05$, rejecting the null hypothesis of no difference in survival between independent groups if $\chi^2$ exceeds the critical value for the test). Survival results were analyzed according to a Kaplan-Meier curve. A p-value <0.05 was considered statistically significant.

Backpacking Prussian Blue Nanoparticles onto T Cells for Combined Photothermal-T Cell Therapy Nanoparticles have many promising therapeutic and imaging applications in cancer, but are often limited because they are rapidly cleared from circulation, exhibit poor biodistribution, and possess low tumor-targeting capabilities. Cellular backpacking, where nanoparticles are coupled with immune cells, may provide a strategy to overcome these limitations. This concept is illustrated by FIG. 16, a graphical abstract.

The results described herein show that backpacking of Prussian blue nanoparticles (PBNP), used for photothermal therapy of tumors, onto antigen-specific T cells, which can traffic to antigen-expressing cells. The inventors detail a scheme for robustly conjugating PBNP onto T cells and demonstrate the physical, phenotypic, and functional properties of the resultant backpacked PBNP-Tc constructs. In vitro experimentation demonstrated improved cytotoxicity with backpacked Tc constructs as compared to either PBNP or T cell treatments alone, suggesting the potential for combined photothermal immunotherapy to improve anti-tumor efficacy in vivo.

Nanoparticles are attractive as cancer therapies because they extravasate through tumor vasculature, target tumors or cells directly via attached ligands, enhance tumor visualization using imaging modalities such as MRI, CT, or fluorescence, and deliver therapeutic agents to the tumor region. See Srikanth M, Kessler J A. Nanotechnology-novel therapeutics for CNS disorders. Nat Rev Neurol. 2012 June; 8(6):307-18; Veiseh O, Gunn J W, Zhang M. Design and fabrication of magnetic nanoparticles for targeted drug delivery and imaging. Adv Drug Deliv Rev. 2010 Mar. 8; 62(3):284-304; Prabhakar U, Maeda H, Jain R K, Sevick-Muraca E M, Zamboni W, Farokhzad O C, et al. Challenges and key considerations of the enhanced permeability and retention effect for nanomedicine drug delivery in oncology. Cancer Res. 2013 Apr. 15; 73(8):2412-7; Veiseh M, Gabikian P, Bahrami S B, Veiseh O, Zhang M, Hackman R C, et al. Tumor paint: a chlorotoxin:Cy5.5 bioconjugate for intraoperative visualization of cancer foci. Cancer Res. 2007 Jul. 15; 67(14):6882-8; and Veiseh O, Sun C, Fang C, Bhattarai N, Gunn J, Kievit F, et al. Specific targeting of brain tumors with an optical/magnetic resonance imaging nanoprobe across the blood-brain barrier. Cancer Res. 2009 Aug. 1; 69(15):6200-7, each incorporated herein by reference in their entirety. Despite these advantages, the clinical translation of nanoparticles in cancer therapy is limited by their rapid clearance from the bloodstream, poor biodistributions, and limited tumor uptake. Cellular backpacking, where nanoparticles are "backpacked" onto the surface of cells, serves as a compelling approach to overcome these limitations of nanoparticles in cancer therapy because it harnesses the cells' innate ability to actively traffic to sites of disease. In addition to using the cell as a vehicle for targeting, cellular backpacking has the potential to leverage native antitumor cellular responses of the cells themselves. It is therefore critical that both nanoparticles and cells retain their native properties or provide additional features upon combination during the backpacking process.

Cellular backpacking of nanoparticles (including nanoshells, liposomes and liposome-like synthetic nanoparticles) has been used in many settings with promising results. See Choi M R, Stanton-Maxey K J, Stanley J K, Levin C S, Bardhan R, Akin D, et al. A cellular Trojan Horse for delivery of therapeutic nanoparticles into tumors. Nano Lett. 2007 December; 7(12):3759-65; and Stephan M T, Moon J J, Um S H, Bershteyn A, Irvine D J. Therapeutic cell engineering with surface-conjugated synthetic nanoparticles. Nat Med. 2010 September; 16(9): 1035-41, each incorporated herein by reference in their entirety. The platform has been exploited for use in imaging applications like MRI to track cells in vivo, coupling with macrophages and T cells, and in photothermal therapy (PTT). See Kircher M F, Allport J R, Graves E E, Love V, Josephson L, Lichtman A H, et al. In vivo high resolution three-dimensional imaging of antigen-specific cytotoxic T-lymphocyte trafficking to tumors. Cancer Res. [Research Support, Non-U.S. Gov't Research Support, U.S. Gov't, P.H.S.]. 2003 Oct. 15; 63(20):6838-46; and Flynn E R, Bryant H C, Bergemann C, Larson R S, Lovato D, Sergatskov D A. Use of a SQUID array to detect T-cells with magnetic nanoparticles in determining transplant rejection. Journal of magnetism and magnetic materials. 2007 April; 311(1):429-35, each incorporated herein by reference in their entirety. PTT, where near infrared (NIR) light-responsive nanoparticles are used to thermally ablate tumors, is an appealing approach. PTT offers the ability to locally ablate tumors in a minimally invasive manner, and potentially the stimulation of endogenous immune responses. See Hoffman H A, Chakarbarti L, Dumont M F, Sandler A D, Fernandes R. Prussian blue nanoparticles for laser-induced photothermal therapy of tumors. RSC Advances. 2014; 4(56):29729-34; Bear A S, Kennedy L C, Young J K, Perna S K, Mattos Almeida J P, Lin A Y, et al. Elimination of metastatic melanoma using gold nanoshell-enabled photothermal therapy and adoptive T cell transfer. PLoS One. 2013; 8(7):e69073; and Wang C, Xu L, Liang C, Xiang J, Peng R, Liu Z. Immunological responses triggered by photothermal therapy with carbon nanotubes in combination with anti-CTLA-4 therapy to inhibit cancer metastasis. Adv Mater. 2014 Dec. 23; 26(48): 8154-62, each incorporated herein by reference in their entirety. Therefore, the inventors hypothesized that nanoparticles backpacked onto immune cells have the potential to yield even more enhanced antitumor responses. Unfortunately, despite this promising application, few studies have systematically investigated this concept after the pioneering examples by Choi et al. See Choi M R, Bardhan R, Stanton-Maxey K J, Badve S, Nakshatri H, Stantz K M, et al. Delivery of nanoparticles to brain metastases of breast cancer using a cellular Trojan horse. Cancer nanotechnology. 2012 December; 3(1-6):47-54, incorporated herein by reference in its entirety.

Here the inventors describe a proof-of-concept study that describes the backpacking of Prussian blue nanoparticles (PBNP), nanoparticles capable of being used for PTT, onto antigen-specific T cells. See Fu G, Liu W, Feng S, Yue X. Prussian blue nanoparticles operate as a new generation of photothermal ablation agents for cancer therapy. Chem Commun 2012; 48:11567-9, incorporated herein by reference in its entirety. PBNP are mixed-valence iron cyanometallate nanoparticles that can be synthesized with theranostic properties, meaning they possess simultaneous therapeutic and diagnostic properties. Previously, the inventors demonstrated the use of PBNP for photothermal therapy (PTT) of tumors in vivo. In separate studies, the inventors demonstrated the use of PBNP as multimodal imaging agents both in vitro and in vivo settings. See Dumont M F, Hoffman H A, Yoon P R, Conklin L S, Saha S R, Paglione J, et al. Biofunctionalized gadolinium-containing Prussian blue nanoparticles as multimodal molecular imaging agents. Bioconjug Chem. 2014 Jan. 15; 25(1): 129-37; Vojtech J M, Cano-Mejia J, Dumont M F, Sze R W, Fernandes R. Biofunctionalized prussian blue nanoparticles for multimodal molecular imaging applications. J Vis Exp. 2015(98): e52621; and Dumont M F, Yadavilli S, Sze R W, Nazarian J, Fernandes R. Manganese-containing Prussian blue nanoparticles for imaging of pediatric brain tumors. Int J Nanomedicine. 2014; 9:2581-95, each incorporated herein by reference in their entirety. Several other groups have also utilized PBNP in theranostic applications for cancer, and still several others have coupled other nanoparticles with immune cells. See Swiston A J, Gilbert J B, Irvine D J, Cohen R E, Rubner M F. Freely suspended cellular "backpacks" lead to cell aggregate self-assembly. Biomacromolecules. 2010 Jul. 12; 11(7):1826-32; Fu G, Liu W, Li Y, Jin Y, Jiang L, Liang X, et al. Magnetic Prussian blue nanoparticles for targeted photothermal therapy under magnetic resonance imaging guidance. Bioconjug Chem. [Research Support, Non-U.S. Gov't]. 2014 Sep. 17; 25(9): 1655-63; Huang X, Jain P K, El-Sayed I H, El-Sayed M A. Plasmonic photothermal therapy (PPTT) using gold nanoparticles. Lasers in medical science. [Research Support, N.I.H., Extramural Review]. 2008 July; 23(3):217-28; Cho N H, Cheong T C, Min J H, Wu J H, Lee S J, Kim D, et al. A multifunctional core-shell nanoparticle for dendritic cell-based cancer immunotherapy. Nat Nanotechnol. 2011 October; 6(10):675-82; Cruz L J, Tacken P J, Fokkink R, Figdor C G. The influence of PEG chain length and targeting moiety on antibody-mediated delivery of nanoparticle vaccines to human dendritic cells. Biomaterials. 2011 October; 32(28): 6791-803; Tomuleasa C, Braicu C, Irimie A, Craciun L, Berindan-Neagoe I. Nanopharmacology in translational hematology and oncology. Int J Nanomedicine. 2014; 9:3465-79; Sheen M R, Lizotte P H, Toraya-Brown S, Fiering S. Stimulating antitumor immunity with nanoparticles. Wiley Interdiscip Rev Nanomed Nanobiotechnol. 2014 September-October; 6(5):496-505; and Berciano-Guerrero M A, Montesa-Pino A, Castaneda-Penalvo G, Munoz-Fernandez L, Rodriguez-Flores J. Nanoparticles in melanoma. Curr Med Chem. 2014; 21(32):3701-16, each incorporated herein by reference in their entirety. However, to our knowledge, none have used PBNP and the unique properties it affords in a cellular backpacking context with immune cells. As compared to other nanoparticles that have been commonly investigated for PTT, such as gold nanoshells, carbon nanotubes, gold nanorods), PBNP offer several advantages: they are FDA-approved (for internal clearance of radioactive contamination), and they are easily synthesized in a single step (a one-pot synthesis) and at low costs which facilitates scalable manufacturing of these nanoparticles—two features important for clinical translation. See FDA: Radiogardase—ferric hexacyanoferrate(ii) capsule: http://www.accessdata.fda.gov/drugsafdadocs/label/2008/021626s007lbl.pdf. [last accessed Mar. 7, 2017], incorporated herein by reference in its entirety. The second component of our constructs, T cells, serve as vehicles to transport the PBNP to the tumor environment. Equally important is the ability of these immune cells to target a specific antigen and generate antigen-specific responses. This ability has previously allowed the use of antigen-specific T cells as immunotherapy for both cancer and opportunistic infections.

In this report, the inventors pursue the PTT capabilities of PBNP backpacked onto antigen-specific T cells, while noting that additional imaging and therapy functions of both the nanoparticles and immune cells can be incorporated or harnessed in future studies. The inventors first describe the facile conjugation scheme used to robustly attach the PBNP onto the surface of the antigen-specific T cells and visualize the resultant PBNP-Tc constructs. Next the inventors measured the size, Vis-NIR light absorption properties, and calculate the photothermal conversion efficiencies of the PBNP when attached to the T cells, properties important for PTT. Subsequently, the inventors perform phenotypic and functional assessments of the antigen-specific T cells after backpacking of the PBNP. Finally the inventors measure antitumor effects of the backpacked PBNP-Tc constructs via evaluating resultant tumor viability. These PBNP-Tc constructs combine the ablative effect of the PBNP-mediated PTT with the targeted antitumor effects of the antigen-specific T cells in vitro. It is our hope that these results will provide insights into the feasibility and functionality of a tandem PBNP-Tc cell construct and pave the way for future studies improving the antitumor efficacy of this photothermal immunotherapy (PTI) for the treatment of malignancies.

The following methods and materials were employed.

Chemicals and Cell Culture Supplies. All chemicals were purchased from Sigma-Aldrich (St Louis, MO) unless otherwise specified. Ultrapure water used in the studies was obtained from a Milli-Q system (MQ; Millipore Corporation, Billerica, MA) with resistivity ≥18 MΩ cm.

Nanoparticle Synthesis and Bioconjugation. PBNP were synthesized at room temperature as previously described. See Volz H G. Pigments, Inorganic. Encyclopedia of Industrial Chemistry. Weinheim: Wiley-VCH; 2006, incorporated herein by reference in its entirety. Briefly, a solution containing 10.6 mg $K_4[Fe(CN)_6]\cdot 3H_2O$ ($2.5\times10^{-5}$ mol) in 5 mL of MQ was added to a vigorously stirred solution containing 6.8 mg $Fe(Cl)_3\cdot 6H_2O$ ($2.5\times10^{-5}$ mol) in 10 mL of MQ. The resulting blue precipitate containing PBNP was rinsed to remove unreacted components by centrifugation and sonication. PBNP were coated with filtered nonfluorescent- or AlexaFluor 488-conjugated avidin (1 mg/ml, Life Technologies, Grand Island, NY) at a ratio of 0.1 mg avidin per 1 mg PBNP via electrostatic self-assembly. See Jaiswal J K, Mattoussi H, Mauro J M, Simon S M. Long-term multiple color imaging of live cells using quantum dot bioconjugates. Nat Biotechnol. 2003 January; 21(1):47-51, incorporated herein by reference in its entirety. This mixture was protected from light and the fluorophore-conjugated avidin was allowed to coat the PBNP over a period of 3 hours an orbital shaker at 4° C.

Nanoparticle Characterization. Following fabrication, the size and zeta potential of the PBNP or avidin-coated PBNP was determined using a Zetasizer Nano ZS (Malvern Instruments, Malvern, UK). Vis-NIR spectra of PBNP and PBNP-Tc constructs in the range of 500-1100 nm were measured on a Genesys 10S spectrophotometer (ThermoFisher Scientific, Waltham, MA) using the VISIONlite software.

Cell Sources. Jurkat Cells. Human Jurkat T cells were obtained from ATCC (Jurkat Clone E6-1, ATCC TIB-152) and were used to examine feasibility of cellular backpacking with a general T cell moiety. Jurkat cells were maintained in RPMI1640 with 10% fetal bovine serum and 1% GlutaMax.

Primary Cell PBMC.

Human peripheral blood mononuclear cells (PBMC) were obtained from healthy volunteers upon informed consent or deidentified discarded blood products under Institutional Review Board-approved protocols at Children's National Health System and Baylor College of Medicine. Whole blood was washed with sterile PBS (Cellgro, Manassas, VA) and PBMC were isolated by ficoll density gradient separation. Red blood cells were lysed (ACK Lysing Buffer) and remaining PBMC were cultured in RPMI 1640 medium supplemented with 2 mmol/L GlutaMAX TM-1 and fetal bovine serum. PBMC were used to generate PHA blasts, lymphoblastoid cell lines (LCL), and antigen-specific T cell lines.

CMV T Cells.

For CMV-specific T cells, PBMC were expanded by stimulation with autologous antigen presenting cells pulsed with an overlapping peptide library spanning the CMV pp65 protein, as previously described. Prior to use in cell proliferation and co-culture, cells were restimulated from a frozen aliquot with irradiated PHA blasts (30 Gy) pulsed with the same overlapping peptide mix in the presence of IL2 (100 U/mL). PHA blasts were generated from PBMC by stimulation with phytohemagglutinin (5 µg/mL) and IL2 (100 U/mL). T cells were maintained in RPMI 1640 supplemented with 45% Click's medium (Irvine Scientific, Santa Ana, CA), 2 mmol/L GlutaMAX TM-1, and 5% human AB serum (Valley Biomedical, Winchester VA)].

EBV T Cells.

For EBV-specific T cells, PBMC were expanded by stimulation with either autologous antigen presenting cells pulsed with an overlapping peptide library spanning the EBV BZLF1, LMP2, and EBNA1 proteins, as previously described, or autologous irradiated LCL. Prior to use in cell proliferation and co-culture, cells were restimulated from a frozen aliquot with irradiated autologous lymphoblastoid cell lines. LCL were first grown by infection with EBV B95-8 virus in the presence of cyclosporine (1 µg/mL) and expanded over 4 weeks. T cells were maintained in RPMI 1640 supplemented with 45% Click's medium (Irvine Scientific, Santa Ana, CA), 2 mmol/L GlutaMAX TM-1, and 5% human AB serum (Valley Biomedical, Winchester VA)].

Backpacking of PBNP onto T cells. Jurkat Tc, EBV Tc, or CMV Tc were biotinylated by co-incubating with 1 mg/mL biotinylation reagent (EZ-Link™ Sulfo-NHS-LC-Biotin) at 4° C. on an orbital shaker, as previously described (Jaiswal 2003). The sulfo-NHS group of the biotinylation reagent covalently binds to free amines of cell surface proteins. The biotinylated T cells were then added to a solution of fluorescent avidin-coated PBNP ($10^{-7}$-$10^{-8}$ mg PBNP/T cell). The mixture was protected from light and the avidin-biotin interactions were allowed to occur for 0.5-1 h at 4° C. on an orbital shaker. The cells were then rinsed to remove unbound nanoparticles by centrifugation. Following this, the PBNP were effectively "backpacked" onto T cells and the construct identified as PBNP-Tc. The efficiency of the backpacking was evaluated using confocal microscopy, and flow cytometry.

Prior to imaging, T cells were stained with viability dyes (DAPI, CFSE, Calcein Blue AM or Calcein Red/Orange) as per the manufacturer's specifications. Images were obtained at the Children's National Medical Center/George Washington University Core Microscopy on the Olympus BX61, Zeiss Apotome, and Olympus FV100 Confocal microscopes, and scale bar is indicative of 20 µm.

Flow Cytometry. The phenotype of naked and backpacked T cells was characterized by staining with antibodies against a panel of T cell markers such as CD3 (145-2C11), CD4 (Gk1.5), CD8 (53-6.7), CD19, CD25, CD45RO, CD45RA, and PD-1 (CD279, RMP1-30, Biolegend) conjugated to FITC, PE, PerCP, APC, APC-Cy7, or PE-Cy7 (BD Biosciences). Examination of T cell backpacking was performed after T cells were stained with Calcein Blue viability dye or CD3 antibody, and coupled to Alexa Fluor 488-avidin-coated PBNP, as described above. Gates were set based on unstained cells. Samples were acquired on the FACSCalibur and BD Accuri flow cytometers, and results were analyzed using Flow Jo 7.6.5 (Tree Star Inc., Ashland, OR).

Photothermal Therapy. To evaluate PTT efficacy in vitro, PBNP or PBNP-Tc constructs were co-cultured with target cells. The co-cultures were established in a 96 well plate and individual wells were subject to PTT using an NIR laser (808 nm Collimated Diode Laser System, Laserglow Technologies) at 2.5 W/cm² for 10 minutes. The temperature of each well during PTT was monitored using a thermocouple or FLIR thermal imaging system (FLIR, Billerca, MA). The photothermal conversion efficiencies of each experimental condition was determined using previously described methodology (Roper 2007, Hoffman 2014). This formulaic determination of photothermal conversion efficiency measured the effective photothermal conversion efficiencies of PBNP or PBNP-Tc in the presence of cells and cell culture media components.

Cell Proliferation. To determine the ability of T cells to proliferate, cells were labelled with CFSE according to the manufacturer's protocol, and stimulated with their corresponding targets. Proliferation was measured after 24 hours.

IFNγ Secretion by ELISPOT. Millipore Multi Screen HTS filter plates (Millipore) were coated with IFN-g capture antibody (Mabtech) at a concentration of 10 ug/mL for 4 hours or overnight at 4 C. Plates were washed with PBS and blocked for 1 hour at 37 C. Cells were then plated at a concentration of $1 \times 10^6$/mL, and exposed to peptide targets containing actin, CMV antigens, or EBV antigens. For development, plates were washed in PBS/.05% Tween 20 (Sigma-Aldrich) and incubated with biotinylated IFN-g detection antibody (0.5 ug/mL; Mabtech) for 2 hours at 37 C, followed by incubation with streptavidin-coupled alkaline phosphatase complex (Vectastain; Vector Laboratories) for 1 hour at room temperature and spots were developed by incubation with 3-amino-9-ethylcarbazole substrate (Sigma) solution. Spot-forming-cells (SFC) were counted and evaluated by Zellnet Consulting using an automated plate reader system (Karl Zeiss).

Co-Culture Experiments. To assess their efficacy against target cells, PBNP-Tc constructs were added at a 2:1 ratio to target cells (LCL or PHA blasts), and cultured in RPMI medium for 4-8 hours after which point PTT was administered as described above. Target cells were labeled with CFSE/Cell Trace Far Red according to the manufacturer's protocol prior to inclusion into the assay. Following completion of co-culture and/or PTT, flow cytometry was used to examine CFSE/Cell Trace Far Red expression on target cells to determine cell viability. Results were compared to a negative control of target cells alone, irradiated target cells, and positive controls of target cells artificially killed by adding DMSO. Experimental groups were as follows: (i) target cells alone, (ii) irradiated target cells (30Gy), (iii) target cells with an irrelevant cell line (Eol or Phx), (iv) target cells with DMSO, (v) target cells with Tc, (vi) target cells with PBNP, (vii) target cells with PBNP-Tc constructs, (viii) target cells with laser, (ix) target cells with Tc and laser, (x) target cells with PBNP and laser, and (xi) target cells with PBNP-Tc constructs and laser. To assess specificity and activation of T cells, EBV Tc (naked or backpacked with PBNP) were stimulated with irradiated LCL cells at a 2:1 ratio, and CMV Tc (naked or backpacked with PBNP) were stimulated with antigen-loaded PHA blasts at a 2:1 ratio for 24 hours and IFNγ ELISpot assay was performed as per manufacturer's protocol (Mabtech, Cincinnati, OH).

Statistics. Statistical analysis was conducted using Prism V5.00 (GraphPad Software, San Diego, CA). Statistical significance was determined from two-tailed Student's t test and values with $p<0.05$ qualified as statistically significant and indicated with an asterisk (*) to indicate comparison between two specified groups or pound sign (#) to indicate comparison to all other groups.

PBNP can be Robustly Backpacked onto Antigen-Specific T Cells

PBNP were synthesized and were either used as synthesized (naked) or coated with AlexaFluor 488-conjugated or non-fluorescent avidin. Dynamic light scattering was used to measure the hydrodynamic diameters and surface charges (zeta potentials) of the resultant uncoated or avidin-coated PBNP. The inventors demonstrated monodisperse size distributions (0.308 vs. 0.387 with avidin; data not shown) and zeta potentials ~−40 mV for both naked and avidin-coated PBNP. Jurkat T cells were used for these experiments to ascertain feasibility of backpacking general T cells with PBNP. PBNP was backpacked onto Tc via avidin-biotin interactions ($K_d \sim 10^{-15}$) according to the scheme indicated (FIG. 17A) to create resultant PBNP-Tc constructs. Confocal fluorescence microscopy indicated successful backpacking of PBNP onto Tc using this protocol (FIG. 17B, right) as compared to naked Tc (FIG. 17B, left). PBNP-Tc constructs were also identifiable by flow cytometry—gating on CD3+ cells that were also positive for Alexa Fluor 488—which indicated stable conjugation of PBNP on to Tc for up to 3 days (FIGS. 17C, 17D).

PBNP Retain their Functional Properties while in PBNP-Tc Construct.

As previously mentioned, one of the principal goals of cellular backpacking is to take advantage of the benefits offered by both T cell therapy and nanomedicine. Thus, an important design consideration of our construct is that both the nanoparticles and cells retain their properties after backpacking. Since the inventors use PBNP primarily as an agent of photothermal therapy, the inventors assessed the properties of the PBNP that pertain to its ability to absorb near infrared light and ablate surrounding tissue. The inventors measured the Vis-NIR spectra, the photothermal heating and cooling kinetics, and the photothermal conversion efficiencies of PBNP-Tc as compared to PBNP alone. Vis-NIR spectroscopy of the PBNP-Tc constructs exhibited a peak between 650-750 nm similar to the characteristic absorption peak observed for free PBNP, while Tc by themselves exhibited no peak absorption at these wavelengths (FIG. 18A). To study the effect of backpacking on photothermal heating and cooling kinetics samples of free PBNP, PBNP-Tc, and Tc were cultured in a 96-well plate and irradiated with an 808 nm NIR laser as previous described. Following 10 minutes of irradiation followed by 10 minutes at room temperature PBNP and PBNP-Tc samples exhibited similar heating (up to ~60° C.) and cooling kinetics with no significant difference between groups (p=0.275; FIG. 18B). The maximum temperatures attained were significantly higher than the temperatures reached by the control samples of Tc alone subjected to PTT (p=0.0002), or either Tc or PBNP alone without NIR laser irradiation (p<0.0001). Temperatures were monitored during and following irradiation, and the cooling kinetics utilized to calculate the photothermal conversion efficiencies of the free and backpacked nanoparticles as previously described. The inventors saw comparable photothermal conversion efficiencies for PBNP-Tc as compared to free PBNP (5.6% vs. 4.9%, FIG. 18C). Our results indicate that PBNP retain their ability to function as an agent of PTT in the PBNP-Tc construct.

PBNP-Tc Constructs Maintain Functionality Against CMV and EBV Antigen-Expressing Targets and Perform Optimally in Combined Photothermal Immunotherapy Having demonstrated that PBNP retains its functional properties after backpacking, the inventors next sought to determine if the functionality of antigen-specific T cells would be impaired by the presence of a nanoparticle backpack. To demonstrate the applicability of the platform in primary T cells, the inventors chose two models of antigen specific T cells: CMV-specific T cells that were tested against cells pulsed with 15-amino acid peptides spanning the pp65 antigen, and EBV-specific T cells that were tested against irradiated EBV-transformed lymphoblastoid cell lines that naturally present EBV antigens to T cells.

The first approach used CMV-specific T cells, and the inventors evaluated their phenotype and function following backpacking with PBNP. CMV-specific T cell proliferation was measured by CFSE dilution over a 12 hour period after which point the cells were analyzed by flow cytometry. The inventors observed that the proliferative capabilities of T cell alone and PBNP-Tc constructs, stimulated by pp65-loaded PHA blasts, were comparable, and both groups proliferated significantly more than the unstimulated T cell control (p=0.002, n=3; FIG. 19A, 19B). Additionally, phenotypic analysis by flow cytometry demonstrated unaltered subsets of CD8+ and CD4+ T cells in T cells as compared to PBNP-Tc (FIG. 19C). Next, T cells and PBNP-Tc were stimulated with actin (nonspecific), PHA (panspecific), or pp65 (CMV specific) and an ELISpot performed to quantify interferon gamma (IFNy) secretion by the T cells after 24 hours of stimulation (FIG. 19D). The inventors identified a decreased IFNy secreting cells in the PBNP-Tc group compared to the T cells alone group, suggesting a possible effect of the PBNP backpacks on cytokine release. Despite this observation, the inventors found that T cells included in the PBNP-Tc construct were still functional since T cells exhibited cytolytic function in vitro against pp65-loaded target cells, and phenotypic analysis revealed that subsets of effector and memory T cells were maintained, with a decreased expression of T cell exhaustion markers in backpacked constructs.

The inventors next postulated that PBNP-Tc would demonstrate synergistic effects, with improved killing of specific targets as compared to either treatment modality alone. PHA blasts (pp65 pulsed targets) were stained with Cell Trace Far Red viability dye, and were co-cultured at a 1:2 ratio with T cells, PBNP, or PBNP-Tc in vitro. Following 4-8 hours of culture, half of the samples were subjected to PTT for ten minutes at a power of 0.98 W. Flow cytometric analysis of target cell fluorescence from individual wells demonstrated a marked decrease in tumor viability (FIG. 19E, 19F). Specifically, the inventors found that compared to the negative control (target cells alone), target cell viability decreased 44.9% (+/−0.45%) with T cells alone (p<0.0001), decreased 85+/−6.1% with PBNP and laser-based PTT (p<0.0001), and decreased 93.7+/−1.4% with the combination of both treatments in the PBNP-Tc group (p<0.0001). Notably, our results indicated superior decreased in tumor viability with the tandem therapy group using PBNP-backpacked T cells as compared to either therapy alone (p=0.0002, FIG. 19F).

PBNP-Tc Constructs Maintain Functionality Against EBV Antigen-Expressing Targets and Perform Optimally in Combined Photothermal Immunotherapy Having demonstrated successful maintenance of T cell functionality and improved therapeutic potential with the CMV-specific PBNP-Tc construct, the inventors sought to determine if this mechanism would hold true in a more relevant antigen processing system. The inventors generated EBV-specific T cells from healthy donors and evaluated their phenotype and function following backpacking with PBNP. As done previously, EBV-specific T cell proliferation was measured by CFSE dilution over a 12 hour period after which point cells were analyzed by flow cytometry. The inventors found that the proliferative capabilities of Tc alone and PBNP-Tc constructs, stimulated by LCL, were comparable, and both groups proliferated significantly more than the unstimulated CTL control (p<0.0001, n=3; FIG. 20A, 20B). Phenotypic analysis of PBNP-backpacked T cells revealed a notable population of CD8+ T cells, as expected, which appeared to be unaltered in PBNP-Tc construct as compared to non-backpacked controls (FIG. 20C). Next, T cells and PBNP-Tc were stimulated with actin (nonspecific), PHA (panspecific), or irradiated LCL cells (EBV specific) and ELISpot performed to determine IFNγ secretion following 24 hours of stimulation (FIG. 19D). Similarly to above in the pulsed peptide model, the inventors observed decreased IFNγ secretion in PBNP-Tc, suggesting a potentially impaired cytokine profile for these cells. Despite the decreased IFNy, EBV-specific T cells in the PBNP-Tc construct were still determined to be functional; T cells exhibited function in in vitro experimentation against LCL target cells, and further phenotypic analysis revealed maintained subsets of effector and memory T cells, and maintained or decreased markers of T cell exhaustion in backpacked constructs.

Next, the inventors sought to examine the potential for a synergistic effect of the PBNP-Tc construct in terms of killing of specific targets compared to either T cell therapy (with EBV-specific T cells) or photothermal therapy (with PBNP and laser) alone. LCL cells (target cells, EBV-specific) were stained with Cell Trace Far Red viability dye, co-cultured at 1:2 ratio with T cells, PBNP, or PBNP-Tc, and following 4-8 hours PTT was performed on designated wells and samples analyzed by flow cytometry as described above. Analysis of target cell fluorescence demonstrated successful decrease in tumor viability (FIG. 20E, 20F). Compared to the negative control of target cells alone, viability decreased 25.4+/−0.9% with T cells (p=0.007), decreased 50.5+/−0.8% with PBNP and laser-based PTT (p=0.007), and decreased 79.8+/−0.3% with the combination in the EBV-specific PBNP-Tc group (p<0.0001). These results demonstrated significantly decreased target cell viability with the combination photothermal immunotherapy using PBNP-Tc as compared to either modality alone (p=0.003, FIG. 20F).

Avidin-Biotin Conjugation Enabled Successful Attachment of PBNPs on CTL

In order to attach PBNPs to T cells, the inventors took advantage of the robust avidin-biotin interactions by contacting avidin-coated PBNPs with biotinylated T cells (FIG. 17A). Dynamic light scattering was used to measure the hydrodynamic diameters and surface charges (zeta potentials) of uncoated or avidin-coated PBNPs. Our synthesis and coating schemes yielded monodisperse size distributions of nanoparticles, in other words, mean hydrodynamic diameters ~80-90 nm, with polydispersity indices ~0.2, and zeta potentials ~−40 mV for both uncoated and avidin-coated PBNPs. The inventors utilized Jurkat T cells to ascertain the feasibility of conjugating PBNPs to T cells to create the CTL:PBNPs constructs according to the scheme indicated (FIG. 17A). Confocal fluorescence microscopy confirmed the successful attachment of PBNPs onto T cells using this protocol (FIG. 17B, right) as compared with uncoated T cells (FIG. 17B, left), assessed immediately after the conjugation (Day 1). CTL:PBNPs constructs were also identified by flow cytometry—gating on CD3+ T cells that were also positive for Alexa Fluor 488 thereby confirming the successful conjugation of PBNPs onto CTL for up to 3 days (FIGS. 17C & 17D). The mean fluorescence intensity (MFI) of PBNPs attached to CTL nonsignificantly decreased over 3 days indicating that the quantity of nanoparticles per cell likely decreased over time. These findings were corroborated with confocal microscopy conducted over 5 days, which demonstrated that the number of PBNPs per cell decreased by Day 3. This 'dilution' of surface bound nanoparticles can be potentially attributed to the expansion of the CTL and/or internalization of the PBNPs by the cells. The findings illustrated the feasibility of the cell-nanoparticle conjugation schema of PBNPs attached to CTL based on avidin-biotin affinity. CTL phenotype & function is not affected by PBNP conjugation. An important design consideration after achieving stable conjugation of nanoparticles onto cells is to ensure that both the nanoparticles and T cells retain their properties after incorporation into the biohybrid construct. As such, the inventors sought to determine if the phenotype and functionality of antigen-specific T cells would be impaired by the presence of a nanoparticle coating. The inventors observed that the proliferative capabilities of CTL alone and CTL:PBNPs constructs, stimulated by EBV peptide-loaded PHA blasts, were comparable, and both groups proliferated significantly more than the unstimulated CTL control (p=0.002, n=7; FIGS. 21A & 21B). Phenotypic analysis by flow cytometry demonstrated unaltered subsets of CD8+ and CD4+ T cells in CTL alone as compared with CTL:PBNPs (FIGS. 21C & 21D). Additional analysis of other subsets—CD45RA and CD45RO, as well as markers of exhaustion TIM3, LAG3, PD1 demonstrated no significant differences between CTL and CTL:PBNPs. In order to evaluate the functional capacity of uncoated and PBNP-coated CTL, the inventors co-cultured CTL with EBV-positive target cells and measured cytokine concentrations in the supernatant as well as the viability of the target cells. Examination of cytokine production by stimulated CTL versus CTL conjugated with varying concentrations of PBNPs demonstrated no notable effect on cytokine production (FIG. 21E). Flow cytometric analysis of target cell fluorescence within the designated conditions demonstrated a marked decrease in the viability of EBV antigen pulsed target cells following the treatment with EBV-specific CTL, which was maintained with the PBNP-coated EBV-CTL (p=0.15, FIG. 21F). Hence, our results demonstrate that EBV-specific CTL maintain their phenotype and antigen-dependent proliferative and functional ability while conjugated to nanoparticles within the CTL:PBNPs construct. PBNPs conjugated onto CTL are functional as agents of PTT. In this study, PBNPs are primarily utilized as an agent of PTT. Therefore, it was essential to ensure that the fundamental properties of the PBNPs (i.e., their ability to absorb near infrared (NIR) light and ablate surrounding tissue) would not be impaired after attachment onto CTL. The inventors first examined the Visible-NIR absorption spectra of CTL, PBNPs and CTL:PBNPs in the 500-1100 nm wavelength range to test whether the PBNPs retained their characteristic absorption peak in the range of 650-750 nm after conjugation to the CTL. The inventors found that the PBNPs retained their Visible-NIR absorption characteristics even after conjugation to CTL (FIG. 22A). Next the inventors assessed the photothermal heating and cooling kinetics to assess the photothermal conversion efficiencies of CTL:PBNPs as compared with PBNPs alone. For heating and cooling profiles, compared with target cells directly irradiated with the NIR laser and target cells co-cultured with CTL and then subjected to the NIR laser (FIG. 22B). Our findings demonstrate that PBNPs retain their photothermal conversion capabilities even after conjugation to CTL. Last, the inventors determined whether the conjugation of PBNPs onto CTL would affect their ability to ablate primary target cells. Flow cytometric analysis of cell viability (fluorescently labeled primary PHA blasts pulsed with EBV peptides) illustrated a decrease in the viability of the target cells following treatment with CTL:PBNPs plus the NIR laser (i.e. target cells+CTL:PBNPs+LASER group; FIGS. 21C & 21D). In contrast, the negative controls of target cells treated with either the NIR laser alone or PBNPs alone did not impact target cell viability. Internal controls of target cells alone and target cells+DMSO were used to ensure cytotoxicity assay accuracy. Notably, our results showed that target cell viability was significantly decreased in the 'target cells+CTL:PBNPs+LASER' group compared with both 'target cells+CTL:PBNPs' and the 'Target Cells+PBNPs+LASER' group (p<0.05 for both comparisons), which is likely attributed to the beneficial effects of combining the ablative capabilities of the PBNPs that are retained in the CTL:PBNPs constructs with the cytotoxic capabilities of the CTL themselves in the construct, compared with either killing modality by itself. Taken together, our results demonstrate that the PBNPs retain their intrinsic absorption properties, photothermal heating/cooling profiles and PTT capabilities even after conjugation to the CTL.

Nanoparticles have been of considerable interest in medicine as a method of drug encapsulation and delivery, but their applicability for immunotherapy is not yet fully explored. In this work, the inventors provide the crucial first steps toward generating a biohybrid nanoimmunotherapy using antigen-specific T cells as vehicles for PBNPs. The inventors described a robust process for conjugating PBNPs onto primary EBV antigen-specific CTL and characterized the individual components, as well as the final CTL:PBNPs construct. Importantly, the inventors demonstrated that the conjugation process maintained the individual functions of both the PBNPs and the CTL.

This Example serves as a proof-of-concept study demonstrating the feasibility of attaching of Prussian blue nanoparticles onto antigen-specific T cells. Both PBNPs and CTLs maintained their intrinsic physical, phenotypic and functional properties within the CTL:PBNPs. This study demonstrated that the new CTL:PBNPs nanoimmunotherapy was effective at treating virus-associated malignancies such as EBV+cancer. The inventors demonstrated successful conjugation of PBNPs onto donor-derived EBV antigen-specific CTL using a generalizable scheme involving biofunctionalization techniques (electrostatic self-assembly and cell surface biotinylation) and avidin-biotin interactions (FIG. 17). Importantly, both the CTL and the PBNPs retained their intrinsic properties in the cell-nanoparticle construct. Specifically, PBNP-coated CTL retained their expression of T-cell-specific markers and their ability to proliferate, express cytokines and lyse EBV antigen-expressing target cells (PHA blasts) relative to uncoated CTL (FIG. 21). The PBNPs retained their characteristic Vis-NIR absorption peak, their photothermal conversion capabilities, and their ability to be used for PTT of primary target cells (FIG. 22). These studies suggest the potential use of our biohybrid CTL:PBNPs as a therapeutic for the treatment of cancer as well as for treatment of infectious diseases.

Nanoparticles have been of considerable interest in medicine as a method of drug encapsulation and delivery, but their applicability for immunotherapy is not yet fully explored. The inventors discloses methods for using antigen specific T cells as vehicles for PBNP and enhanced the process of coupling Prussian blue nanoparticles onto T cells and characterized the individual components as well as the combined new product of the PBNP-Tc construct. The backpacking process maintains the individual functions of the PBNP and the T cells. This is valuable for the photothermal immunotherapy, as it builds upon the existing, well-established effector properties of both nanoparticles and T cells, and will not benefit from a major alteration in either.

Although the inventors demonstrated no effect of cellular backpacking on the ability of T cells to proliferate and specifically kill their targets, the cells tested did show decreased cytokine production which could be attributed to the presence of surface nanoparticles occluding the engagement of various surface receptors and ligands to the environment.

In summary, the inventors have demonstrated the feasibility of generating a PBNP-backpacked T cell construct providing a foundation for further development of a clinical platform that combines the strengths of immunotherapy with that of nanomedicine.

Photothermal Therapy Improves the Efficacy of a MEK Inhibitor in Neurofibromatosis Type 1-Associated Malignant Peripheral Nerve Sheath Tumors Malignant peripheral nerve sheath tumors (MPNSTs) are aggressive tumors with low survival rates and the leading cause of death in neurofibromatosis type 1 (NF1) patients under 40 years old. Surgical resection is the standard of care for MPNSTs, but is often incomplete and can generate loss of function, necessitating the development of novel treatment methods for this patient population. Here, the inventors describe a novel combination therapy comprising MEK inhibition and nanoparticle-based photothermal therapy (PTT) for MPNSTs. MEK inhibitors block activity driven by Ras, an oncogene constitutively activated in NF1-associated MPNSTs, while PTT serves as a minimally invasive method to ablate cancer cells. Our rationale for combining these seemingly disparate techniques for MPNSTs is based on several reports demonstrating the efficacy of systemic chemotherapy with local PTT. The inventors combined the MEK inhibitor, PD-0325901 (PD901), with Prussian blue nanoparticles (PBNPs) as PTT agents, to block MEK activity and simultaneously ablate MPNSTs. These data demonstrate the synergistic effect of combining PD901 with PBNP-based PTT, which converge through the Ras pathway to generate apoptosis, necrosis, and decreased proliferation, thereby mitigating tumor growth and increasing survival of MPNST-bearing animals. These results suggest the potential of this novel local-systemic combination "nanochemotherapy" for treating patients with MPNSTs.

Neurofibromatosis type 1 (NF1) is a disorder of the nervous system affecting 1 in ~3,500 individuals worldwide. See Riccardi, V. M. & Smirniotopoulos, J. Neurofibromatosis, Phenotype, Natural History, and Pathogenesis. *Journal of Neuropathology & Experimental Neurology* 51, 658 (1992); and Katz, D., Lazar, A. & Lev, D. Malignant peripheral nerve sheath tumour (MPNST): the clinical implications of cellular signaling pathways. *Expert Rev Mol Med* 11, e30, doi: 10.1017/S1462399409001227 (2009), each incorporated herein by reference in their entirety. This disorder is characterized by the development of benign neurofibromas, a significant portion of which progresses to malignant peripheral nerve sheath tumors (MPNSTs), aggressive tumors with low 5-year survival rates (<50%) and the leading cause of death in NF1 patients under 40 years old. See Evans, D. G. et al. Malignant peripheral nerve sheath tumours in neurofibromatosis 1. *Journal of medical genetics* 39, 311-314 (2002), incorporated herein by reference in its entirety.

Surgical resection is the standard of care for MPNSTs. See Grobmyer, S. R., Reith, J. D., Shahlaee, A., Bush, C. H. & Hochwald, S. N. Malignant peripheral nerve sheath tumor: molecular pathogenesis and current management considerations. *Journal of surgical oncology* 97, 340-349 (2008), incorporated herein by reference in its entirety. However, surgery can be invasive, debilitating, incomplete, and result in loss of function. See Ferner, R. E. & Gutmann, D. H. International consensus statement on malignant peripheral nerve sheath tumors in neurofibromatosis 1. *Cancer research* 62, 1573-1577 (2002), incorporated herein by reference in its entirety. This necessitates the development of novel methods for the management of MPNSTs.

In response to this need, the inventors describe a novel combination therapy of systemically (orally) administered MEK inhibitors with locally (intratumorally) administered nanoparticle-based photothermal therapy (PTT) for treating MPNSTs. A rationale for combining MEK inhibition with PTT is premised on precedent in the literature that has demonstrated the improved efficacy of combining chemotherapy with PTT for treating diverse cancers. See Hauck, T. S., Jennings, T. L., Yatsenko, T., Kumaradas, J. C. & Chan, W. C. W. Enhancing the toxicity of cancer chemotherapeutics with gold nanorod hyperthermia. *Advanced Materials* 20, 3832-3838 (2008); You, J., Zhang, G. & Li, C. Exceptionally high payload of doxorubicin in hollow gold nanospheres for near-infrared light-triggered drug release. *ACS Nano* 4, 1033-1041, doi: 10.1021/nn901181c (2010); Zhang, W. et al. Synergistic effect of chemo-photothermal therapy using PEGylated graphene oxide. *Biomaterials* 32, 8555-8561, doi: 10.1016/j.biomaterials.2011.07.071 (2011); Mehtala, J. G. et al. Synergistic effects of cisplatin chemotherapy and gold nanorod-mediated hyperthermia on ovarian cancer cells and tumors. *Nanomedicine (Lond)* 9, 1939-1955, doi: 10.2217/nnm.13.209 (2014); Li, X., Takashima, M., Yuba, E., Harada, A. & Kono, K. PEGylated PAMAM dendrimer-doxorubicin conjugate-hybridized gold nanorod for combined photothermal-chemotherapy. *Biomaterials* 35, 6576-6584, doi: 10.1016/j.biomaterials.2014.04.043 (2014); Tao, Y. et al. Engineered, self-assembled near-infrared photothermal agents for combined tumor immunotherapy and chemophotothermal therapy. *Biomaterials* 35, 6646-6656, doi: 10.1016/j.biomaterials.2014.04.073 (2014); Wu, M., Wang, Q., Liu, X. & Liu, J. Highly efficient loading of doxorubicin in Prussian Blue nanocages for combined photothermal/chemotherapy against hepatocellular carcinoma. *RSC Advances* 5, 30970-30980 (2015); Fay, B. L., Melamed, J. R. & Day, E. S. Nanoshell-mediated photothermal therapy can enhance chemotherapy in inflammatory breast cancer cells. *Int J Nanomedicine* 10, 6931-6941, doi: 10.2147/IJN.S93031 (2015); and Xue, P., Bao J., Wu, Y., Zhang, Y. & Kang, Y. Magnetic Prussian blue nanoparticles for combined enzyme-responsive drug release and photothermal therapy. *RSC Advances* 5, 28401-28409 (2015), each incorporated herein by reference in their entirety. Studies have successfully used graphene oxide, gold nanorods, and nanoshells as agents for PTT to improve the efficacy of chemotherapy in cancers such as inflammatory breast cancer and hepatocellular carcinoma. One mechanism by which PTT improves the efficacy of chemotherapy is by increasing the membrane permeability of targeted tumor cells causing increased uptake of the chemotherapeutic agent. Conversely, PTT also benefits from chemotherapy, which elicits systemic effects to complement its inherently local effects. Motivated by these earlier findings, the inventors sought to exploit these complementary effects in the context of NF1-associated MPNSTs. Specifically, they combined the MEK inhibitor, PD-0325901 (PD901), with Prussian blue nanoparticles (PBNPs) as PTT agents, to block MEK activity and simultaneously ablate MPNSTs when irradiated with a near infrared (NIR) laser. This study represents the first attempt at exploiting the synergy between PTT and chemotherapy for the treatment of NF1-associated MPNSTs. MEK inhibitors are small molecule inhibitors that target the Ras signaling pathway. NF and NF1-associated MPNST patients pathognomonically lack neurofibromin, a negative regulator of oncogenic Ras signaling. Without neurofibromin protein function, Ras is allowed constitutive activation. See Gottfried, O. N., Viskochil, D. H. & Couldwell, W. T. Neurofibromatosis Type 1 and tumorigenesis: molecular mechanisms and therapeutic implications. *Neurosurg Focus* 28, E8, doi: 10.3171/2009.11.FOCUS09221 (2010); and Rad, E. & Tee, A. R. Neurofibromatosis type 1: Fundamental insights into cell signaling and cancer. *Semin Cell Dev Biol* 52, 39-46, doi: 10.1016/j.semcdb.2016.02.007 (2016), each incorporated herein by reference in their entirety. The Ras signal transduction pathway generates a phosphorylation cascade through RAF, MEK, and ERK, which in its phosphorylated form (p-ERK) affects the transcription of genes associated with uncontrolled cell proliferation and increased cancer progression. See Tanoue, T., Adachi, M., Moriguchi, T. & Nishida, E. A conserved docking motif in MAP kinases common to substrates, activators and regulators. *Nat Cell Biol* 2, 110-116, doi: 10.1038/35000065 (2000); and Farassati, F. et al. Ras signaling influences permissiveness of malignant peripheral nerve sheath tumor cells to oncolytic herpes. *The American journal of pathology* 173, 1861-1872, doi: 10.2353/ajpath.2008.080376 (2008), each incorporated herein by reference in their entirety. Research suggests the potential of using MEK inhibitors to block Ras activity in MPNSTs, but these studies were conducted in either cell lines or in animal models that yielded marginal results in treating MPNSTs. See Varin, J. et al. Dual mTORC1/2 inhibition induces anti-proliferative effect in NF1-associated plexiform neurofibroma and malignant peripheral nerve sheath tumor cells. Oncotarget, doi: 10.18632/oncotarget.7099 (2016); Dodd, R. D. et al. NF1 deletion generates multiple subtypes of soft-tissue sarcoma that respond to MEK inhibition. *Molecular cancer therapeutics* 12, 1906-1917, doi: 10.1158/1535-7163.MCT-13-0189 (2013); Endo, M. et al. Prognostic significance of AKT/mTOR and MAPK pathways and antitumor effect of mTOR inhibitor in NF1-related and sporadic malignant peripheral nerve sheath tumors. *Clin Cancer Res* 19, 450-461, doi: 10.1158/1078-0432.CCR-12-1067 (2013); Ambrosini, G. et al. Sorafenib inhibits growth and mitogen-activated protein kinase signaling in malignant peripheral nerve sheath cells. *Molecular cancer therapeutics* 7, 890-896, doi: 10.1158/1535-7163.MCT-07-0518 (2008); and Jessen, W. J. et al. MEK inhibition exhibits efficacy in human and mouse neurofibromatosis tumors. *J Clin Invest* 123, 340-347, doi: 10.1172/JCI60578 (2013), each incorporated herein by reference in their entirety. Based on the improved efficacy of combining chemotherapy with PTT, the inventors hoped that the effects of the MEK inhibitor PD901 would be made more potent when combined with PBNP based PTT for treating MPNSTs. PTT is a minimally invasive method for destroying tumors using light-activated nanoparticles and a low power NIR laser. See Loo, C., Lowery, A., Halas, N., West, J. & Drezek, R. Immunotargeted nanoshells for integrated cancer imaging and therapy. *Nano letters* 5, 709-711 (2005); and Huang, X., Jain, P. K., El-Sayed, I. H. & El-Sayed, M. A. Plasmonic photothermal therapy (PPTT) using gold nanoparticles. *Lasers in medical science* 23, 217-228 (2008), each incorporated herein by reference in their entirety. In this study, the inventors use PBNPs for PTT of MPNSTs, which the inventors have previously used for ablation of subcutaneous neuroblastoma. See Dumont, M. F. et al. Biofunctionalized gadolinium-containing prussian blue nanoparticles as multimodal molecular imaging agents. *Bioconjugate chemistry* 25, 129-137, doi: 10.1021/bc4004266 (2014); Dumont, M. F., Yadavilli, S., Sze, R. W., Nazarian, J. & Fernandes, R. Manganese-containing Prussian blue nanoparticles for imaging of pediatric brain tumors. *Int J Nanomedicine* 9, 2581-2595, doi: 10.2147/IJN.S63472 (2014); Hoffman, H. A., Chakrabarti, L., Dumont, M. F., Sandler, A. D. & Fernandes, R. Prussian blue nanoparticles for laser-induced photothermal therapy of tumors. *RSC Advances* 4, 29729, doi: 10.1039/c4ra05209a (2014); and Vojtech, J. M., Cano-Mejia, J., Dumont, M. F., Sze, R. W. & Fernandes, R. Biofunctionalized prussian blue nanoparticles for multimodal molecular imaging applications. *J Vis Exp* e52621, doi: 10.3791/52621 (2015), each incorporated herein by reference in their entirety. Compared to alternative nanoparticles used for PTT, PBNPs offer several advantages: they can easily be synthesized in a single, scalable step at low costs, and are already FDA-approved for human oral consumption (to treat radioactive poisoning) suggesting their potential safety for use as PTT agents. See Faustino, P. J. et al. Quantitative determination of cesium binding to ferric hexacyanoferrate: Prussian blue. *Journal of pharmaceutical and biomedical analysis* 47, 114-125, doi: 10.1016/j.jpba.2007.11.049 (2008); and Yang, Y. et al. Quantitative determination of thallium binding to ferric hexacyanoferrate: Prussian blue. *International journal of pharmaceutics* 353, 187-194, doi: 10.1016/j.ijpharm.2007.11.031 (2008), each incorporated herein by reference in their entirety.

To determine whether PD901 combined with PBNP-based PTT results in improved treatment outcomes for MPNSTs, the inventors used the mouse M2 MPNST cells in vitro, and a syngeneic, subcutaneous mouse model of MPNST in vivo. See Antoszczyk, S. et al. Treatment of orthotopic malignant peripheral nerve sheath tumors with oncolytic herpes simplex virus. *Neurooncology* 16, 1057-1066, doi: 10.1093/neuonc/not317 (2014), incorporated herein by reference in its entirety. First, the inventors assessed the efficacy of PD901 and PBNP-based PTT individually in treating MPNST cells in vitro. Specifically, the effects of the individual therapies on MPNST cell viability and the mechanisms of cell death induced by the therapies the inventors assessed. Next, the efficacy of the PD901/PTT combination in treating MPNST cells in vitro and whether this combination of PD901 and PTT is synergistic (using dose response and drug interaction calculations) was assessed. Finally, the effects of the PD901/PTT combination on tumor progression and animal survival in vivo were determined. The findings of these studies demonstrate the feasibility of using a novel kind of nanochemotherapy for preclinically treating MPNSTs, an important prelude to eventual clinical translation.

PD901 Effectively Treats MPNSTs In Vitro by Blocking ERK Activation.

In order to validate the presumed anti-MEK mechanism of action of PD901 in M2 cells, the inventors measured its effects on the activation of ERK, which is located downstream of MEK in the Ras signaling pathway. M2 cells were treated with vehicle (DMSO) or 1 $\mu$M PD901 for four or eight hours, and then harvested, lysed, and probed for phosphorylated ERK (p-ERK) and total ERK, using actin as a loading control. 1 $\mu$M PD901 effectively blocked the activation of ERK (p-ERK) at both four and eight hours, demonstrated by no visible p-ERK bands on the Western blot in the PD901-treated lanes, compared with distinct p-ERK bands observed in the vehicle-treated lane (FIG. 23*a*). Our finding of decreased p-ERK expression in M2 cells is consistent with those in the published literature, which confirm decreased ERK activation after a few hours of PD901 treatment. See Hennig, M. et al. Targeting mitogen-activated protein kinase with the inhibitor PD0325901 decreases hepatocellular carcinoma growth in vitro and in mouse model systems. *Hepatology* 51, 1218-1225, doi: 10.1002/hep.23470 (2010), incorporated herein by reference in its entirety.

To determine the effect of MEK inhibition on MPNST viability, the inventors treated M2 cells with varying doses of PD901 and measured cell viability. PD901 decreased M2 cell viability in a concentration-dependent manner, with an IC50 of approximately 1 µM (FIG. 23b). These results are consistent with earlier studies using MEK inhibitors in other cell lines. See De Raedt, T. et al. PRC2 loss amplifies Ras-driven transcription and confers sensitivity to BRD4-based therapies. *Nature* 514, 247-251, doi: 10.1038/nature13561 (2014), incorporated herein by reference in its entirety.

To determine the mechanisms causing decreased M2 viability, the mechanisms of cell death (apoptosis versus late apoptosis/necrosis) and the effects of PD901 treatment on the M2 cell cycle were analyzed. PD901 was found to decrease M2 viability by both apoptosis (Annexin V+7AAD-) and late apoptosis/necrosis (7AAD+) at all concentrations tested (FIG. 23c). Further, PD901 caused a significant arrest of M2 cells in the G0/G1 phase in a concentration-dependent manner (FIG. 23d), indicating decreased proliferation after treatment. These results with M2 cells suggest that MEK inhibition using PD901 is a feasible modality for treating MPNST in vitro, by the blockade of ERK activation, which would otherwise increase cell proliferation and division; Katz, D., Lazar, A. & Lev, D. Malignant peripheral nerve sheath tumour (MPNST): the clinical implications of cellular signaling pathways. *Expert Rev Mol Med* 11, e30, doi: 10.1017/S1462399409001227 (2009).

PBNPs function as effective agents for PTT of MPNSTs in vitro.

To determine whether PBNPs function as effective agents for PTT of MPNSTs, studies were conducted in vitro using M2 cells. First, PBNPs were synthesized with monodisperse size distributions as measured by dynamic light scattering (mean hydrodynamic diameter of 68.1 nm), and with their characteristic cubic structures as observed by transmission electron microscopy (FIG. 24a). The synthesized PBNPs heated in a concentration-dependent manner when irradiated with an 808 nm NIR laser at 1.5 W/cm$^2$ laser power density for 10 minutes (FIG. 24b). Importantly, this incremental heating consistently resulted in decreased viability of M2 cells when the PBNPs were similarly irradiated with the NIR laser (FIG. 24c). Temperatures around 45° C. and greater appeared to decrease viability of M2 cells to a similar extent (approximately 15-25% viable). Interestingly, PBNP-based PTT triggered differing levels of apoptosis and/or late apoptosis/necrosis in M2 cells depending on the temperature ranges to which they were heated. This temperature range was, in turn, dependent on the concentration of PBNPs used for PTT since both laser power and duration of laser irradiation were kept constant in these studies. M2 cells that were heated to the 45-50° C. temperature range triggered cell death through primarily apoptosis; M2 cells treated with 0.03 mg/mL PBNPs, which attained an average temperature of 46.8° C. after ten minutes irradiation at 1.5 W/cm$^2$, resulted in apoptosis in 72.2% of cells. In contrast, M2 cells that were heated to >50° C. triggered cell death through primarily late apoptosis/necrosis; M2 cells treated with 0.05 mg/mL PBNPs, which attained an average temperature of 51.3° C. after ten minutes irradiation at 1.5 W/cm$^2$, resulted in late apoptosis/necrosis in 73.2% of cells (FIG. 24d). This finding of a temperature range preferentially triggering cell death by either apoptosis or necrosis is corroborated by an earlier study using gold nanorods to ablate tumor cells in vitro. See Pattani, V. P., Shah, J., Atalis, A., Sharma, A. & Tunnell, J. W. Role of apoptosis and necrosis in cell death induced by nanoparticle mediated photothermal therapy. *Journal of Nanoparticle Research* 17, 1-11, doi: 10.1007/s11051-014-2822-3 (2015), incorporated herein by reference in its entirety. Thus, PBNPs function as effective agents for PTT of MPNSTs resulting in decreased viability of these cells in vitro. More importantly, our data suggests a potentially tunable mechanism of inducing cell death using PBNP-based PTT (apoptosis versus necrosis), which can be leveraged in subsequent studies to improve treatment outcomes for MPNSTs in vivo.

PD901 and PTT Synergistically Combine to Yield Improved Treatment Outcomes for MPNSTs In Vitro.

After determining the individual efficacies of both PD901 and PBNP-based PTT in treating M2 cells in vitro, the inventors next sought to examine the potential benefit of combining the treatments. Cell viability studies demonstrated that combining the two treatments in vitro was able to significantly decrease the viability of M2 cells more than either treatment administered alone (FIG. 25a). At both low doses (0.125 µM PD901, "LOW PD901;" 0.005 mg/mL PBNP-based PTT, "LOW PTT") and high doses (1 µM PD901, "HIGH PD901;" 0.05 mg/mL PBNP-based PTT, "HIGH PTT"), the combination treatment resulted in significantly decreased cell viability over the individual treatments administered under identical conditions. Additionally, PD901+PTT ("HIGH Combo") functioned to effectively block p-ERK expression in M2 cells, mirroring the effects of PD901 treatment alone (FIG. 25b). It is important to note that while both PD901 alone and the HIGH Combo treatment resulted in similar Western blot readouts, further studies are needed to elucidate whether these effects are sustained in the two treatment groups over time. Earlier studies have demonstrated a rescue of p-ERK expression over time after MEK inhibition. Therefore, therapies that yield sustained decrease of p-ERK expression may be important for improved treatment outcomes in MPNSTs.

Interestingly, PTT alone was able to decrease p-ERK expression (FIG. 25b), signifying its potential impact on Ras signaling at a point along its signal transduction pathway. This finding suggests that although PD901 and PTT function differently to decrease M2 cell viability (cell cycle arrest vs. ablation, respectively), these effects converge along the Ras signaling pathway. Using PTT to alter a prominent signal transduction pathway in cancer has not been previously explored. Deeper mechanistic studies to determine the effect of PTT on Ras signaling in the context of NF1-associated MPNST are ongoing.

As another component of studies assessing the effects of the PD901/PTT combination in vitro, the sought to determine if the effects of PD901 and PTT on decreasing M2 cell viability are synergistic. Dose response curves measuring the viability of M2 cells in vitro in response to increasing concentrations of either individual treatment or the PD901/PTT combination demonstrated that PD901 and PTT synergistically combine to decrease M2 viability (FIG. 25c). The coefficients of drug interaction (CDI) for three of the doses tested (doses 2, 3, and 4) were calculated to be less than 0.7, indicating significant drug synergy between PD901 and PTT. See Xu, S. P. et al. Synergistic effect of combining paeonol and cisplatin on apoptotic induction of human hepatoma cell lines. *Acta pharmacologica Sinica* 28, 869-

878, doi: 10.1111/j.1745-7254.2007.00564.x (2007), incorporated herein by reference in its entirety.

PD901 and PTT Combine to Decrease MPNST Progression and Increase Survival In Vivo.

Motivated by our in vitro findings, the inventors generated a syngeneic mouse model of MPNST using the M2 cell line in B6129SF1/J mice based on previous literature to test the in vivo efficacy of the novel combination therapy. Mice were subcutaneously injected with M2 cells. When the mice exhibited established tumors (~10 mm in diameter), the MPNST-bearing mice were divided into four groups and were: 1) untreated (n=5), 2) treated with PD901 (n=5), 3) treated with PTT (n=5), or 4) treated with both PD901 plus PTT (n=5). Tumor progression was measured daily and mouse survival was monitored post-treatment. Tumors in the untreated group progressed at the fastest rate (FIG. 26a, black lines), and mice in this group succumbed to high tumor burden after 14 days or less (median survival=13 days; FIG. 26b). In contrast, mice treated with PD901 plus PTT exhibited slower tumor growth compared to all other groups, as demonstrated by the decreased slopes of their tumor progression curves (FIG. 26a, purple lines). This slower tumor growth translated to significantly increased survival in mice treated with both PD901 plus PTT (median survival=29 days) compared to mice in all other treatment groups, where median survivals of 18 days and 15 days were observed in PD901-treated and PTT-treated mice, respectively (FIG. 26b; $p<0.05$). Hematoxylin and eosin (H&E) stains of tumors extracted from MPNST-bearing mice 8 h after treatment confirmed these findings of increased tumor cell death post-combination treatment (FIG. 25a). It should be noted that the improved treatment outcomes were observed using a single local administration of PBNP-based PTT and daily oral dosing of PD901. Further optimization of this combination therapy that leverages the convergent biological effects of these two therapies observed in vitro may result in further improvement in treatment outcomes for MPNSTs over those currently observed, in addition to conferring potential benefits such as less frequent doses of the MEK inhibitor.

Taken together, our findings demonstrate the feasibility of using PD901 in combination with PBNP-based PTT for achieving improved treatment outcomes for MPNSTs in vivo.

In summary, the inventors disclose a new combination therapy comprising two distinct but synergistic treatments: MEK inhibition using the small molecule inhibitor PD901 and PBNP-based PTT. The inventors demonstrated a convergence of the two treatment strategies on the Ras signal transduction pathway, which resulted in decreased ERK activation. These effects, when combined with the effects of photothermal ablation via PTT, resulted in decreased growth of MPNSTs both in vitro and in vivo. Ongoing studies in our group will build upon these data to further mechanistically describe the combined effect of PD901 and PTT so as to better exploit the synergy of this combination nanochemotherapy in clinically treating NF1-associated MPNSTs.

The following methods and materials were employed.

Chemicals and PBNP synthesis. PD0325901 (#PZ0162; PD901) was purchased from Sigma-Aldrich (St. Louis, MO). PBNPs were synthesized from their constituent salts purchased from Sigma-Aldrich as previously described; Hoffman, H. A., Chakrabarti, L., Dumont, M. F., Sandler, A. D. & Fernandes, R. Prussian blue nanoparticles for laser-induced photothermal therapy of tumors. *RSC Advances* 4, 29729, doi: 10.1039/c4ra05209a (2014).

MPNST cells. The M2 mouse MPNST cell line was a gift from Dr. Samuel A. Rabkin (Massachusetts General Hospital, Harvard Medical School; Boston, MA; Antoszczyk, S. et al. Treatment of orthotopic malignant peripheral nerve sheath tumors with oncolytic herpes simplex virus. *Neurooncology* 16, 1057-1066, doi: 10.1093/neuonc/not317 (2014)), originally isolated from spontaneously arising tumors in Nf1/Trp53 heterozygous mice obtained from the LF Parada laboratory. The M2 cells were cultured in DMEM with 10% FBS and 1% Penicillin/Streptavidin (Life Technologies, Carlsbad, CA).

Western blots. Treated M2 cells were lysed in 1×RIPA buffer [50 mM Tris-HCL (pH 7.4), 150 mM NaCl, 1% Triton X-100, 1% sodium deoxycholate, 0.1% SDS, 1 mM EDTA, complete protease inhibitor (Roche, Basel, Switzerland) and phosphatase inhibitor (Roche, Basel, Switzerland)]. Samples were analyzed by SDS-PAGE and transferred onto PVDF membranes (Millipore, Billerica, MA). The blots were then blocked in 5% non-fat milk in TBST, followed by incubation of primary antibodies at 4° C. overnight. After washing, the blots were incubated in horseradish peroxidase (HRP)-conjugated secondary antibodies at room temperature for 1 hour. Signals were detected using ECL or ECL plus (GE healthcare, Little Chalfont, United Kingdom) followed by film development. The primary antibodies used are as follows: p-ERK (1:1,000, rabbit, Cell Signaling, Danvers, MA), ERK (1:2,000, rabbit, Cell Signaling, Danvers, MA), and β-actin (1:10,000, mouse, Sigma-Aldrich, St. Louis, MO).

Cell viability assays. M2 cells were seeded at 50,000 cells per well in 96-well cell culture plates overnight. After treatment, the cells were analyzed for viability using the ATP-based CellTiter-Glo Luminescent Cell Viability Assay (Promega, Madison, WI).

Luminescence was read on the EnSpire Multimode Plate Reader (PerkinElmer, Waltham, MA).

Flow cytometry. After the relevant treatments, M2 cells were stained with PE-Annexin V (BD Pharmingen, Franklin Lakes, NJ) and 7AAD (BD Pharmingen, Franklin Lakes, NJ). For cell cycle analysis, M2 cells were stained with propidium iodide (ThermoFisher Scientific, Carlsbad, CA) after treatment. Flow cytometry was performed on a BD FACSCalibur and analyzed with the FlowJo 7.6 software.

Dynamic light scattering. Hydrodynamic diameter of PBNPs (10 µg/mL) was measured by dynamic light scattering on a Zetasizer (Malvern Instruments Ltd., Malvern, United Kingdom) as per the manufacturer's specifications.

Transmission electron microscopy. PBNPs were dropped onto 100 mesh standard formvar grids (Electron Microscopy Sciences, Hatfield, PA) and visualized by transmission electron microscopy on a JEM-2100 FEG high-resolution transmission electron microscope at 200 kV.

Photothermal therapy. An 808 nm NIR laser (Laserglow Technologies, Toronto, Ontario, Canada) at 1.5 W/cm$^2$ was used for all PTT studies. PBNPs were added to 96-well plates at varied concentrations and irradiated for ten minutes. A thermocouple (Omega Engineering, Stamford, CT) was used to measure the temperature of the wells at one-minute intervals.

Analysis of PD901 and PBNP-based PTT interaction in vitro. The coefficient of drug interaction (CDI) was used to analyze the interaction between PD901 and PBNP-based PTT in treating M2 cells in vitro, as previously described36. Briefly, M2 cells were subject to varying doses of PD901, PBNP-based PTT, or combination PD901/PTT. The doses of PD901 used were 0.125-100 µM; the doses of PBNP-based PTT were 0.005-0.1 mg/mL irradiated for 10 min with the NIR laser. The doses for the PD901+PTT combination were the combined doses used for each individual treatment. The viability of the M2 cells at each dose was measured using the ATP-based CellTiter-Glo Luminescent Cell Viability Assay (Promega, Madison, WI). The CDI for a given dose of PD901, PTT, or the PD901/PTT combination was calculated using the formula: CDI=(M2 viability in response to PD901/PTT)/(M2 viability in response to PD901×M2 viability in response to PTT). A value of CDI<1 indicated drug synergy, CDI<0.7 indicated significant drug synergy, CDI=1 indicated additivity, and CDI>1 indicated drug antagonism.

Animals. All animal studies were approved by the Institutional Animal Care and Use Committee (IACUC) of Children's National Health System, Washington, DC (Protocol #00030571). The studies were conducted in accordance with the approved IACUC guidelines. 4-6 week old female B6129SF1/J mice were purchased from Jackson Laboratory (Bar Harbor, ME). Mice were monitored daily for symptoms of toxicity (e.g. sick mouse posturing, infection, impaired mobility, weight loss, self-mutilation, bleeding). No mice were euthanized due to toxicity symptoms, and no measurable weight loss was recorded. The animals were acclimated for 3-4 days prior to tumor inoculation.

In vivo studies. 1 million M2 cells were injected into the backs of B6129SF1/J mice in 100 µL 50% phosphate buffered saline (PBS, Life Technologies, Carlsbad, CA)/ 50% Matrigel (Corning, Corning, NY). Treatment commenced when tumors reached 10 mm in diameter. Animals were treated in four groups: (1) Untreated (n=5): animals received no treatment, (2) PTT-treated (n=5): animals were intratumorally injected with 50 µL of 1 mg/mL PBNPs and irradiated for 10 minutes with 1.5 W/cm² NIR laser, (3) PD901-treated (n=5): animals were given 5 mg/kg PD901 daily by oral gavage in 0.5% hydroxypropyl methylcellulose and 0.2% Tween80, and (4) PD901 plus PTT combo-treated (n=5): animals were given both PTT and PD901 treatments as listed above. Animals were euthanized if tumors reached >20 mm in diameter, if their tumors became ulcerated, or if they exhibited signs of distress. Tumors were measured daily by calipers. For histological analysis of the effects of the treatments, tumors were harvested eight hours post treatment (treatments described above; n=2-3 per group), processed, and stained with hematoxylin and eosin (H&E) for subsequent microscopy.

Statistical analysis. Statistical analysis was conducted using Prism V5.00 (GraphPad Software, San Diego, CA). Statistical significance between groups in the plots was determined using a two-tailed Student's t-test and values with p<0.05 qualified as statistically significant and were marked with an asterisk (*) to indicate comparison between two specified groups.  indicates p-values <0.01, while * indicates p-values <0.001. p-values >0.05 qualified as not statistically significant. The samples sizes (n) for each group were either ≥3/group or explicitly mentioned for each study. For the animal survival study, a log-rank test was used to determine statistically significant differences in survival between the various groups, ($\alpha$=0.05, rejecting the null hypothesis if x2>critical value for the test). Survival results were analyzed by generating Kaplan-Meier plots. A p-value <0.05 was considered statistically significant in this analysis.

The foregoing disclosure merely describes exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claims.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The invention claimed is:

1. A combined immunotherapeutic and photothermal method for treating a subject having a neoplasm, tumor, or cancer comprising:

treating the subject with an immunotherapy that comprises administering a checkpoint inhibitor which is an anti-CTLA-4 checkpoint inhibitor and/or an anti-PD-1/PD-L1 checkpoint inhibitor and wherein the checkpoint inhibitor is selected from the group consisting of ipilimumab, nivolumab, pembrolizumab and atezolizumab, administering intratumorally Prussian blue nanoparticles comprising Prussian blue nanoparticles coated with first and second polymer coatings having opposite charges to each other; and photothermally treating the subject; wherein the neoplasm, tumor or cancer is neuroblastoma; and wherein the first and second polymer coatings comprise polyallylamine hydrochloride and poly(acrylic acid).

2. The method of claim 1, wherein the Prussian blue nanoparticles comprise a compound having the chemical formula:

$$A_xB_yM_z[M'(CN)_6]_a \cdot n(H_2O)$$

wherein:

A represents at least one of VO", Ca, V, Cr, Mn, Fe, Co, Ni, Cu, In, Ga, Sr, Ir, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

B represents at least one of VO", Ca, V, Cr, Mn, Fe, Co, Ni, Cu, In, Ga, Sr, Ir, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

M represents at least one of VO", Ca, V, Cr, Mn, Fe, Co, Ni, Cu, In, Ga, Sr, Ir, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

M' represents at least one of VO", Ca, V, Cr, Mn, Fe, Co, Ni, Cu, In, Ga, Sr, Ir, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

x is from 0.1 to about 1;
Y is from 0 to about 1;
z is from 0.1 to about 4;
a is from 0.1 to about 4; and
n is from 0.1 to about 24.

3. The method of claim 2, wherein in the formula $$A_xB_yM_z[M'(CN)_6]_a \cdot n(H_2O), A=B=K.$$

4. The method of claim 2, wherein the Prussian blue nanoparticles comprise $KFe(Fe(CN)_6)$.

5. The method of claim 2, wherein in the formula $A_xB_yM_z[M'(CN_6]_a \cdot n(H_2O)$, A=K and B=Gd.

6. The method of claim 2, wherein in the formula $A_xB_yM_z[M'(CN_6]_a \cdot n(H_2O)$, A=K and B=Mn.

7. The method of claim 1, wherein the immunotherapy further comprises administering T cells.

8. The method of claim 1, wherein the immunotherapy further comprises administering T cells that recognize at least one cancer antigen.

9. The method of claim 1, where in the first and second polymer coatings comprise polyallylamine hydrochloride (PAH) and poly(acrylic acid)(PAA) further coated with polyethylene glycol (PEG) in the following order from core to surface: Prussian blue nanoparticles, PAH, PAA and PEG.

10. The method of claim 1, wherein the immunotherapy comprises administering the anti-CTLA-4 checkpoint inhibitor ipilimumab.

11. The method of claim 1, wherein the immunotherapy comprises administering an anti-PD-1/PD-L1 checkpoint inhibitor comprising nivolumab, pembrolizumab or atezolizumab.

12. The method of claim 1, wherein the T cells or the checkpoint inhibitors are conjugated to the Prussian blue nanoparticles.

13. The method of claim 1, wherein the Prussian blue nanoparticles have an average size ranging from 1 nm to 10 microns.

14. The method of claim 1, wherein the nanoparticles further comprise an antibody, aptamer, or other ligand that binds to a cancer cell antigen.

15. The method of claim 1, wherein the photothermal treatment comprises radiating the Prussian blue nanoparticles with light having a wavelength of 600 nm to 1,200 nm.

* * * * *